(12) United States Patent
Stevenson et al.

(10) Patent No.: US 8,660,645 B2
(45) Date of Patent: *Feb. 25, 2014

(54) ELECTRONIC NETWORK COMPONENTS UTILIZING BIOCOMPATIBLE CONDUCTIVE ADHESIVES FOR DIRECT BODY FLUID EXPOSURE

(75) Inventors: Robert A. Stevenson, Canyon Country, CA (US); Warren S. Dabney, Orchard Park, NY (US); Richard L. Brendel, Carson City, NV (US); John Roberts, Carson City, NV (US); Christine A. Frysz, Orchard Park, NY (US)

(73) Assignee: Greatbatch Ltd., Clarence, NY (US)

( * ) Notice: Subject to any disclaimer, the term of this patent is extended or adjusted under 35 U.S.C. 154(b) by 1271 days.

This patent is subject to a terminal disclaimer.

(21) Appl. No.: 12/472,222

(22) Filed: May 26, 2009

(65) Prior Publication Data
US 2009/0259265 A1 Oct. 15, 2009

Related U.S. Application Data

(63) Continuation-in-part of application No. 12/269,255, filed on Nov. 12, 2008, now Pat. No. 7,917,219, which is a continuation-in-part of application No. 11/535,343, filed on Sep. 26, 2006, now Pat. No. 7,535,693, which is a continuation of application No. 11/136,843, filed on May 24, 2005, now Pat. No. 7,113,387, which is a continuation of application No. 10/778,954, filed on Feb. 12, 2004, now Pat. No. 6,985,347, which is a continuation of application No. 10/377,086, filed on Feb. 27, 2003, now Pat. No. 6,765,779.

(60) Provisional application No. 60/360,642, filed on Feb. 28, 2002.

(51) Int. Cl.
*A61N 1/05* (2006.01)

(52) U.S. Cl.
USPC .............................. 607/37; 607/116; 361/302

(58) Field of Classification Search
USPC ..................................... 607/37, 116; 361/302
See application file for complete search history.

(56) References Cited

U.S. PATENT DOCUMENTS

| 4,152,540 A | 5/1979 | Duncan |
| 4,352,951 A | 10/1982 | Kyle |
| 4,424,551 A | 1/1984 | Stevenson |
| 4,847,617 A * | 7/1989 | Silvian .................... 340/870.16 |
| 5,333,095 A | 7/1994 | Stevenson |
| 5,759,197 A * | 6/1998 | Sawchuk et al. ................ 607/36 |

(Continued)

*Primary Examiner* — Christopher D Koharski
*Assistant Examiner* — Michael Carey
(74) *Attorney, Agent, or Firm* — Michael F. Scalise

(57) ABSTRACT

An implantable passive or active electronic network component or component network is provided which is suitable for prolonged direct body fluid exposure and is attachable to a conductive surface, circuit trace, lead or electrode. The electronic network component or component network includes (1) a non-conductive body of biocompatible and non-migratable material, (2) a conductive termination surface of biocompatible and non-migratable material, associated with the body, and (3) a connection material of biocompatible and non-migratable material, for conductively coupling the termination surface to the conductive surface, circuit trace, lead or electrode. The electronic network component may include a capacitor, a resistor, an inductor, a diode, a transistor, an electronic switch, a MEMs device, or a microchip. A biocompatible and non-migratable adhesive is utilized to conductively couple components of the individual components of the electronic network, such as the conductive surface, circuit trace, lead or electrode.

50 Claims, 43 Drawing Sheets

(56) References Cited

U.S. PATENT DOCUMENTS

| | | |
|---|---|---|
| 5,782,891 A * | 7/1998 | Hassler et al. .................. 607/36 |
| 5,905,627 A | 5/1999 | Brendel |
| 5,959,829 A | 9/1999 | Stevenson |
| 5,973,906 A | 10/1999 | Stevenson |
| 6,008,980 A | 12/1999 | Stevenson |
| 6,055,455 A | 4/2000 | O'Phelan |
| 6,643,903 B2 | 11/2003 | Stevenson |
| 6,708,065 B2 * | 3/2004 | Von Arx et al. .................. 607/60 |
| 6,765,779 B2 | 7/2004 | Stevenson |
| 7,363,090 B2 | 4/2008 | Halperin |
| 7,489,495 B2 | 2/2009 | Stevenson |
| 7,729,770 B2 * | 6/2010 | Cabelka et al. .................. 607/37 |
| 7,917,219 B2 * | 3/2011 | Stevenson et al. .............. 607/37 |
| 7,970,474 B2 * | 6/2011 | Starke ............................. 607/37 |
| 2005/0197677 A1 | 9/2005 | Stevenson |
| 2006/0247684 A1 | 11/2006 | Halperin |
| 2007/0112398 A1 | 5/2007 | Stevenson |
| 2008/0049376 A1 | 2/2008 | Stevenson |
| 2008/0071313 A1 | 3/2008 | Stevenson |
| 2008/0085043 A1 | 4/2008 | Watanabe |
| 2008/0116997 A1 | 5/2008 | Dabney |
| 2008/0132987 A1 | 6/2008 | Westlund |
| 2008/0161886 A1 | 7/2008 | Stevenson |

* cited by examiner

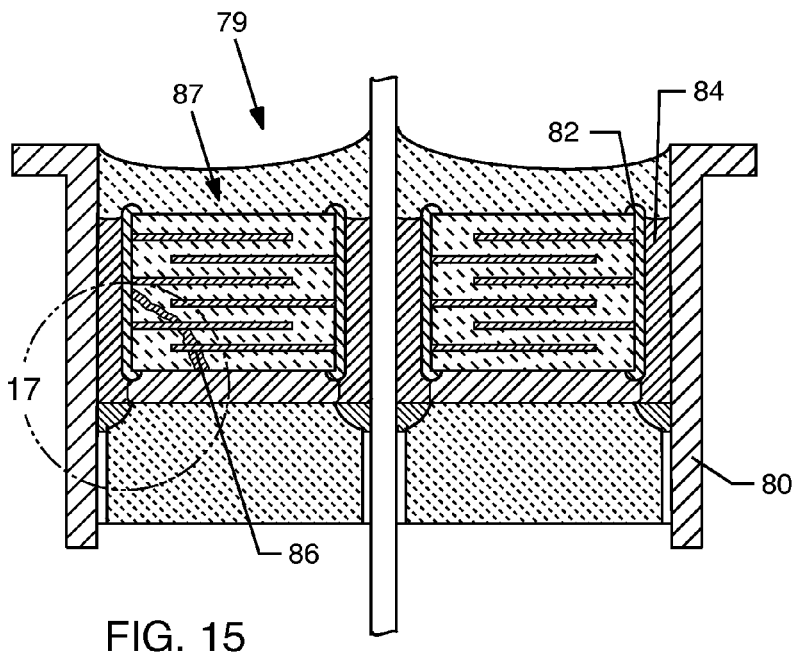
FIG. 15
PRIOR ART
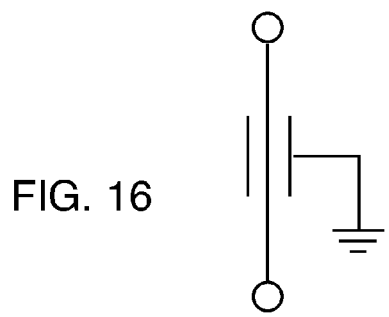
FIG. 16
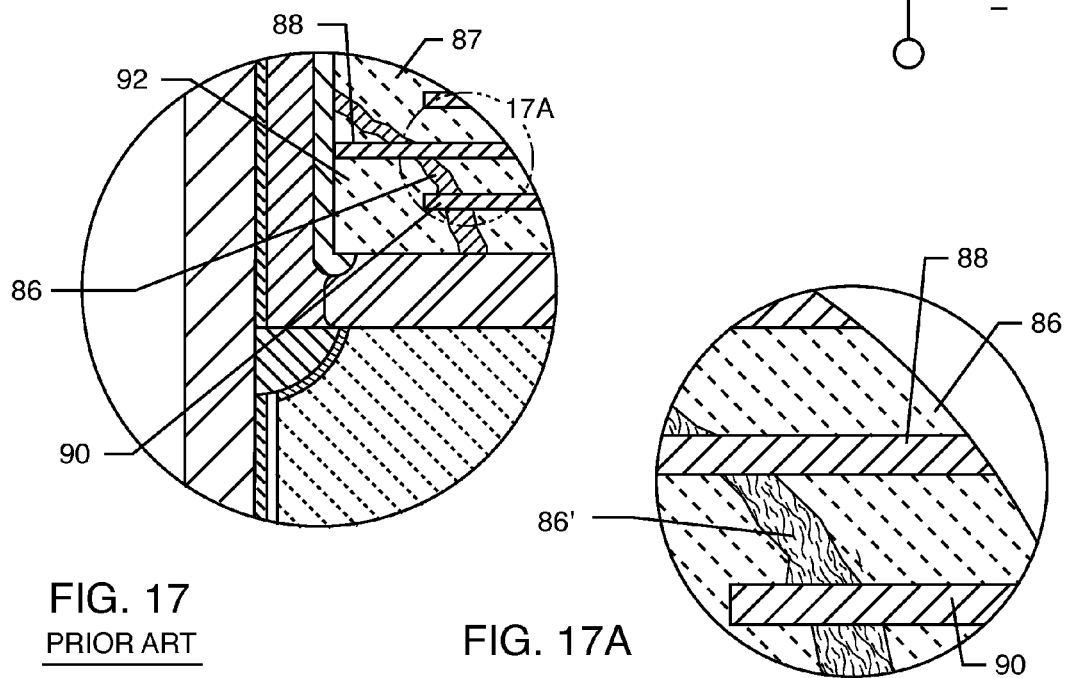
FIG. 17
PRIOR ART
FIG. 17A

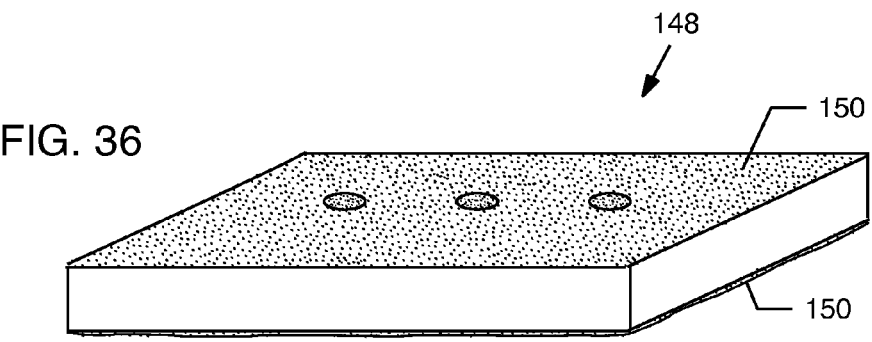
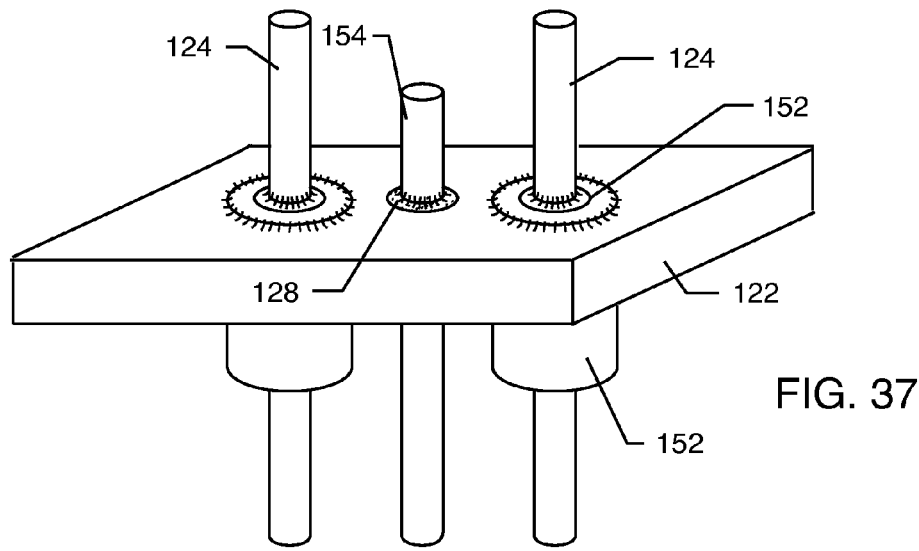
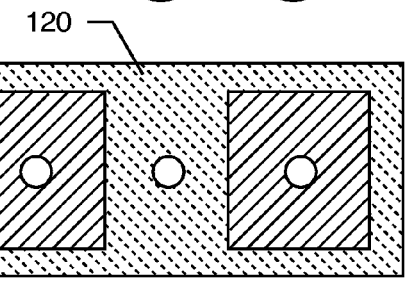
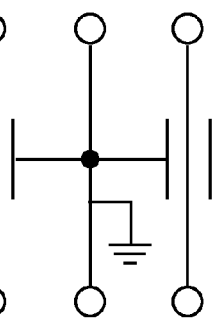
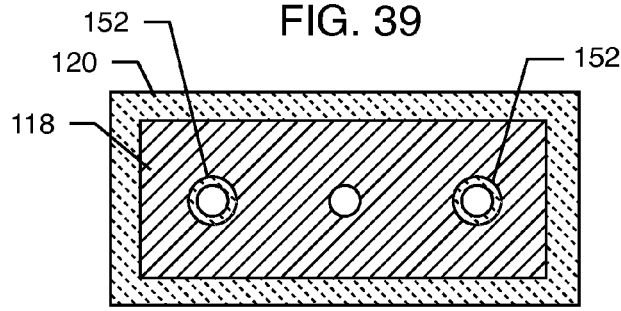

| French Guage | Diameter (mm) | Diameter (inches) |
|---|---|---|
| 3 | 1 | 0.039 |
| 4 | 1.35 | 0.053 |
| 5 | 1.67 | 0.066 |
| 6 | 2 | 0.079 |
| 7 | 2.3 | 0.092 |
| 8 | 2.7 | 0.105 |
| 9 | 3 | 0.118 |
| 10 | 3.3 | 0.131 |
| 11 | 3.7 | 0.144 |
| 12 | 4 | 0.158 |
| 13 | 4.3 | 0.170 |
| 14 | 4.7 | 0.184 |
| 15 | 5 | 0.197 |
| 16 | 5.3 | 0.210 |
| 17 | 5.7 | 0.223 |
| 18 | 6 | 0.236 |
| 19 | 6.3 | 0.249 |
| 20 | 6.7 | 0.263 |
| 22 | 7.3 | 0.288 |
| 24 | 8 | 0.315 |
| 26 | 8.7 | 0.341 |
| 28 | 9.3 | 0.367 |
| 30 | 10 | 0.393 |
| 32 | 10.7 | 0.419 |
| 34 | 11.3 | 0.455 |

FIG.66

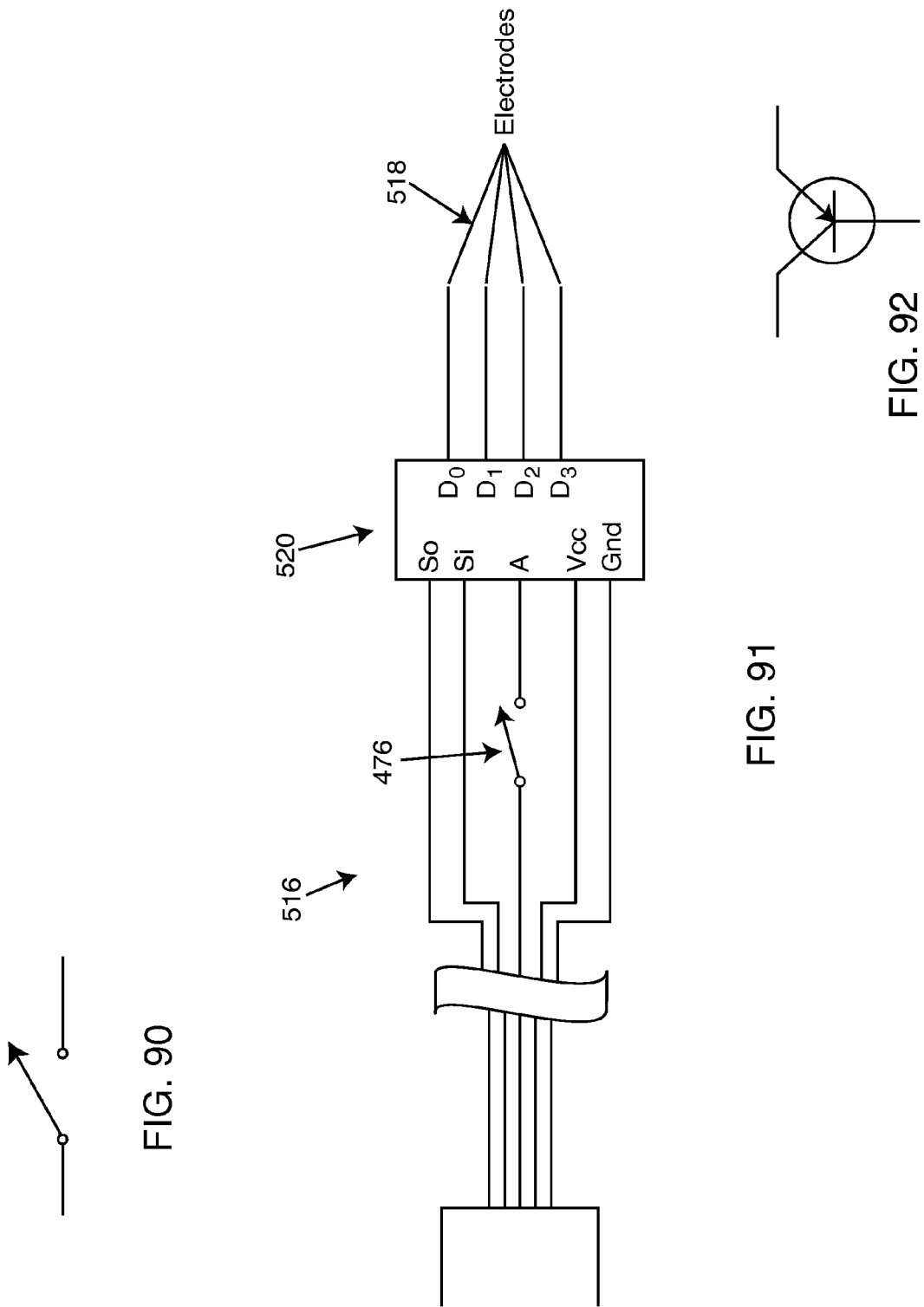

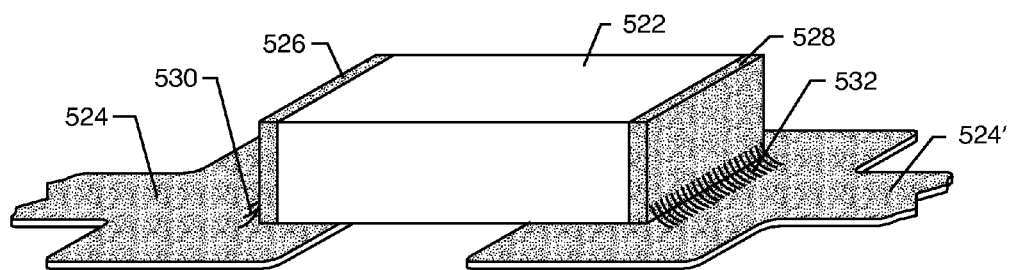
FIG. 93
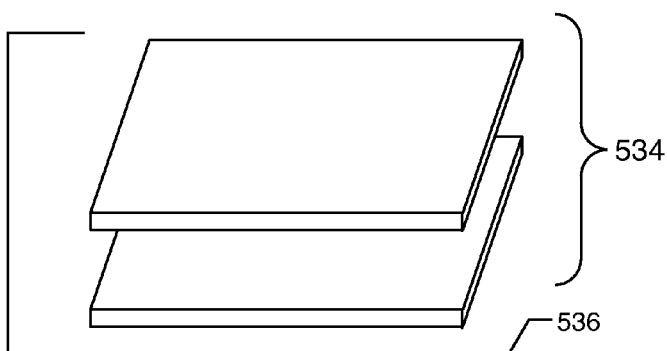
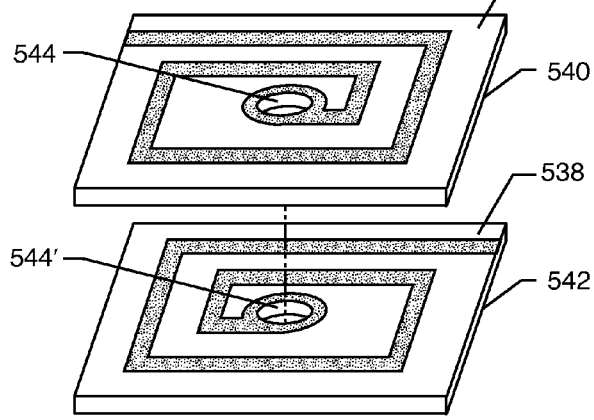
FIG. 94
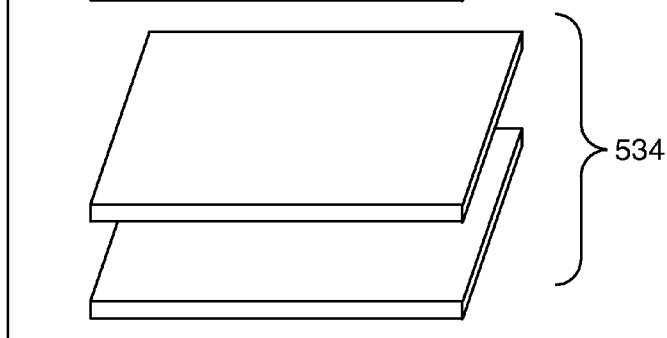
FIG. 95

ELECTRONIC NETWORK COMPONENTS UTILIZING BIOCOMPATIBLE CONDUCTIVE ADHESIVES FOR DIRECT BODY FLUID EXPOSURE

CROSS-REFERENCE TO RELATED APPLICATIONS

The present application is a continuation-in-part of U.S. patent application Ser. No. 12/269,255, filed on Nov. 12, 2008, now U.S. Pat. No. 7,917,219, which is a continuation-in-part of U.S. patent application Ser. No. 11/535,343, filed on Sep. 26, 2006, now U.S. Pat. No. 7,535,693, which is a continuation of U.S. patent application Ser. No. 11/136,843, filed on May 24, 2005, now U.S. Pat. No. 7,113,387, which is a continuation of U.S. patent application Ser. No. 10/778,954, filed on Feb. 12, 2004, now U.S. Pat. No. 6,985,347, which is a continuation of U.S. patent application Ser. No. 10/377,086, filed on Feb. 27, 2003, now U.S. Pat. No. 6,765,779, which claims priority from U.S. Provisional App. No. 60/360,642, filed on Feb. 28, 2002.

BACKGROUND OF THE INVENTION

This invention relates generally to active and passive electronic network components and component networks suitable for prolonged direct body fluid exposure and attachable to a conductive surface, circuit trace, leadwire or electrode. The component networks may include components mounted on or bonded to a substrate, flex cable, implanted lead or the like. More specifically, this invention relates to materials and methods of manufacturing all types of capacitors, inductors, resistors, bandstop filters, diodes, transient voltage suppressors, electronic switches, transistors, RFID chips and their associated antennas, microchips, lead based sensors (like blood gas or pressure), MEMs devices and the like, so that they can be exposed directly to body fluid without the need for a hermetic seal. Moreover, the present invention relates to use of biocompatible and non-migratable electrical connections in connection with said active and passive components or component networks.

It is well known that EMI feedthrough capacitors can be attached to the flanges of human implantable hermetic seals for reliable EMI filter performance. These EMI filters are very important for bypassing and attenuating RF signals from undesirable emitters, such as cell phones, microwave ovens and the like.

These devices are generally designed with one or more monolithic ceramic feedthrough capacitors or monolithic ceramic rectangular chip capacitors in intimate relation with the hermetic terminal. In general, monolithic ceramic capacitors are considered to be sensitive electronic components and are not manufactured of biocompatible materials. Monolithic ceramic capacitors are typically constructed of a barium titinate dielectric into which active and ground electrode plates are interspersed. The ceramic capacitor dielectric is typically of barium titinate, zirconium titinate, or other high dielectric constant ceramic materials with various dopants added to control its dielectric constant, temperature stability and electrical properties. Barium titinate in itself is biocompatible; however, the electrodes and the termination materials are generally not biocompatible. Typical monolithic ceramic capacitors would include a palladium-silver, or nickel silver electrode system (base metal electrode). Other electrode systems are possible, including ternary, which is a high fire system consisting of an alloy of gold, platinum and palladium.

Typical capacitor termination materials are applied in two ways. The first system involves a glass frit, which is loaded with metallic particles along with a binder and vehicle system to make a paste. This paste is then applied to the capacitor and fired into place. The conductive particles make contact with the exposed electrode plates and place them in parallel. A properly formed capacitor termination is a highly conductive surface to which electrical connections may be made through soldering or other methods. Typical materials used for this glass frit are a silver or copper loaded glass frit or a palladium silver or platinum silver composition. Silver is relatively inexpensive and highly conductive and is also available in a wide variety of flakes and spherical shapes.

The second system involves plating of the termination. There are a number of plating methods currently used, including a barrier plating technique which consists of plating down nickel and then various materials on top of the nickel to promote solderability. The nickel acts as a barrier layer and prevents leaching off of the capacitor. For example, if tin or copper were plated on top of the nickel, the tin or copper would readily wet with solder and the nickel would form a layer resistant to leaching or removal from the capacitor.

Therefore, in nearly all of the prior art devices the monolithic ceramic capacitor is placed on the inside of the implantable medical device. In other words, this places the sensitive monolithic ceramic capacitor away from the body fluid so that it cannot come in contact with the body fluid. Another way of stating this is that a hermetic terminal is used to prevent intrusion of body fluid into the interior of the electronic device. Accordingly, all of the electronic circuits, including the substrate, circuit boards, battery, computer chips, capacitors and electromagnetic interference capacitors, are customarily placed in a suitable location inside the titanium housing of the implantable medical device so that they are protected from body fluids.

However, modern pacemakers and implantable defibrillators tend to be very small in size and are very cramped in terms of space inside the unit. Thus, placing the capacitor on the outside of the housing would desirably increase the volumetric efficiency of the overall design, such as by allowing a larger battery to be inserted in the device housing. In addition, laser welds used to seal the housing, typically comprised of titanium, will have a lesser effect on the capacitor. Recognizing this, U.S. Pat. No. 6,055,455 discloses a monolithic ceramic capacitor placed on the outside (or the body fluid side) of the hermetic terminal of an implantable medical device. In this patent the concept of decoupling the EMI before it gets to the inside of the pacemaker or the implantable medical device is emphasized. However, it makes no difference from a filter effectiveness point of view whether the capacitor is on the inside surface or on the outside surface of the hermetic seal.

Electromagnetic interference consists of a number of modulated carrier frequencies, for example, the carrier frequency of a typical cellular phone. What is important is that the gap between the feedthrough capacitor and the hermetic seal be a wave-guide beyond cut off. In other words, that gap needs to be small enough so that the wavelength of the electromagnetic interference will not readily pass through it. As it turns out, after doing wave-guide calculations, this is relatively easy to do for a medical implant application. One reason for this is the human body's tendency to reflect and absorb EMI at frequencies of 3 GHz and above. In other words, it really makes no difference whether the EMI feedthrough capacitor is on the body fluid side or the inside of the hermetic terminal of an implantable medical device. The closely spaced feedthrough capacitor presents such a small wave-guide that it would take frequencies in excess of 20 GHz to effectively re-radiate around the filter. However, at frequencies of 3 GHz and above the human body is so effective in attenuating such signals that higher frequencies are really not of importance.

A significant mistake found in the prior art is the notion that adding some sort of an adjunct sealant over the top of a monolithic ceramic feedthrough capacitor will allow it to operate in the presence of body fluids. Body fluid is an extremely corrosive and conductive medium. There are many dissolved minerals in body fluid, including salt and potassium, which readily conduct electricity in their ionic state. Polymers and adjunct sealants and conformal coatings on electronic components have a number of weaknesses which include problems with adhesion and also bulk permeability. Simply stated, over a long period of time moisture can still penetrate through virtually any adjunct non-hermetic sealant and eventually reach the capacitor. In addition, adjunct sealants and coatings have a different thermal coefficient of expansion as compared to the barium titinate ceramic capacitor. Thus, after exposure to temperature excursions or simply after a long period of time, the adhesion of the coating to the capacitor surface starts to break down. This could allow a thin film of moisture or body fluid to be present at the surface of the ceramic capacitor. In fact, any slight separation of any of the adjunct sealant could cause a small gap or tightly spaced separation into which moisture could easily form. One way that moisture can form in such a tiny space is through dew point condensation. That is, during temperature excursions moisture laden or vapor laden air could enter such a small separation and then deposit out as a thin film of moisture.

One of the most common and severe failures of electronic components comes from a process known as metal migration, whisker formation or dendritic growth. A dendrite can form of various migratable materials, including silver, tin, and the like. Another common way of describing this phenomenon is through tin or silver whiskers. Once these dendrites form across the surface of the capacitor, the capacitor's insulation resistance drops dramatically. This can short out the capacitor, thereby shorting out the entire implantable medical device. The effect could also be degraded insulation resistance, which could result in reduced battery life or in reduced functionality of the output waveform of the implantable medical device.

To illustrate this problem, FIG. 1 is a cross-sectional view of a prior art unipolar hermetic terminal assembly 10, similar to that described by U.S. Pat. No. 4,424,551, the contents of which are incorporated herein. FIG. 2 is an electrical schematic diagram of the unipolar hermetic terminal assembly of FIG. 1. At first glance it would appear that the capacitor 12, shown inside the ferrule 14, is well protected against body fluid by the sealant 16, such as an epoxy seal. However, in actual practice there is a mismatch of thermal coefficients of expansion between the polymers and the barium titinate of the ceramic capacitors. There are also adhesion problems and difficulties with bulk permeability. Accordingly, across both the top and bottom surfaces of the capacitor 12 one can usually see, at high magnification, a small separation 17 is often present between the sealing material and the capacitor surface itself. This would be a separation between the top surface of the capacitor 12 and sealing material 16 due to a separation in the bond between non-conductive sealing material 16 and the capacitor 12. After a prolonged period of time, moisture can penetrate into this space, and a metal migration or dendrite 18 can form either on the top or bottom of the capacitor 12. The formation of this dendrite could lead to either immediate or latent catastrophic failure of the implanted medical device.

With reference to FIGS. 3-5, a prior art unipolar feedthrough capacitor 20 is mounted to a hermetic terminal of an implantable medical device, such as a cardiac pacemaker, an implantable cardioverter defibrillator (ICD) a cochlear implant, or the like. It will be seen from the electrical schematic diagram in FIG. 4 that the characteristics of the feedthrough capacitor 20 of FIGS. 3 and 5 are identical to those of the capacitor 12 shown in FIG. 1. Such prior art capacitors 20 are typically constructed using a silver-bearing or palladium silver bearing-glass frit for the outside diameter termination surface 22 as well as the inner diameter surface 24. Connecting material 26 connects the capacitor's lead wire 28 to the inside diameter surface 24 of the feedthrough capacitor 20. The material 26 is typically of a silver-filled conductive polyimide, or a lead or tin bearing solder or the like. If the capacitor 20 were exposed and placed on the body fluid side of the medical device, a thin film of moisture 30 would be present across the surface of the capacitor. This moisture could be present from direct immersion in body fluid or from the penetration of any adjunct sealants by body fluids. In the presence of moisture 30, dendrites or metal migration 32 would form or grow between the areas of opposite polarity 22 and 24. This dendritic growth or migration can also occur from the capacitor's outside diameter metallization material 22 and the material used to make the electro-mechanical connection between the capacitor lead wire 28, and the capacitor's inside diameter 24. Even if the capacitor's outside diameter termination material 22 was of biocompatible material, (which is not typical in the prior art), the connection material 26 which forms the electro-mechanical connection from the capacitor outside diameter 22 to a ferrule 34, could still be problematic because the connecting material 26 is typically a silver-filled conductive thermosetting polymer, such as a conductive polyimide or the like.

Thus, in the presence of moisture and a voltage bias, the silver is free to migrate and form dendrites 32 as shown in FIGS. 3 and 5. Of course those skilled in the art will realize that the formation of these dendrites 32 is highly undesirable because they are conductive and tend to lower the insulation resistance or short out the capacitor 20. This is particularly problematic in a low voltage pacemaker application where the formation of the silver, tin or other dendrites 32 would preclude the proper operation of the implanted medical device. Another undesirable effect of the formation of these dendrites 32 is that they would tend to conduct current and thereby dissipate power unnecessarily, leading to premature battery failure of the implanted medical device. Premature battery failure is highly undesirable and leads to unwanted surgery and increased expense, usually the replacement of the entire implantable medical device.

With reference now to FIGS. 6 and 7, a surface mounted quadpolar capacitor 36 is illustrated, such as that described in U.S. Pat. No. 5,333,095, the contents of which are incorporated herein. As can be seen from the illustration, dendrites 38 or 38' can form between any points of opposite polarity as long as there is migratable material as well as a migratable medium. Migratable mediums include thin films of moisture, solvents or the like. Accordingly, another problem can arise during cleaning or washing of the capacitor 36. Any entrapped cleaning solvents, such as alcohol, water or degreasers, when coupled with a bias voltage, can allow for the migration of the metallic migratable materials. It will be appreciated that not only can the dendrites 38 form between lead wires 40 of opposite polarity, but also at 38' between two lead wires of the same polarity and an adjacent ground at the capacitor outside diameter metallization 42. Both conditions are highly undesirable in that the dendrite 38 or 38' formation could short out or reduce the insulation resistance between the two lead wires 40 thereby degrading any biological signal sensing that they may perform. The term "short out" does not necessarily imply that the dendrite 38 or 38' will form a zero ohm connection because the resistance of the dendrite, metal migration or whisker depends upon a number of factors including the thickness density and length of the dendrite 38 or 38' that is formed. Dendrites do not form a continuous sheet, but rather are discontinuous. Time lapse photography has shown that dendrites form side branches similar to a tree with many leaves. What results is a matrix of silver conductive particles that have many strange geometric shapes. Accordingly, the resistivity of such a structure is highly variable, ranging from several thousand ohms down to a very few ohms.

FIGS. 8 and 9 show an in-line quadpolar capacitor 44 is illustrated wherein the outside or ground termination 46 is in two localized areas. Such localization minimizes the opportunity for dendrites to form. However, when the electrical connection is made between the termination material 46 and the conductive ferrule material 48 using a connective material 50 which is comprised of migratable material, typically a silver-filled solder or conductive thermal-setting polymer such as a conductive polyimide or the like, the formation of dendrites 52 or 52' is possible in the presence of moisture. A dendrite 52 could form between the capacitor conductive metallization 46 and lead wire 54, or a dendrite 52' could form between lead wires 54, as illustrated.

With reference to all of the illustrated prior art, when the capacitor is installed in the housing of an implantable medical device and the capacitor is oriented toward the inside, such dendrites typically do not form. This is because the inside of the implantable device is hermetically sealed. This prevents intrusion of body fluids or other moisture. In addition, the active implantable medical device is typically thoroughly cleaned and then baked dry prior to assembly. The device is then laser welded shut. Prior to final sealing, the interior of the implantable medical device is evacuated at high vacuum and then back-filled with dry nitrogen. In other words, the ceramic capacitors of the prior art are never really exposed to moisture throughout their design life. Accordingly, the dendrites 52 in FIG. 8 do not have a chance to form when the capacitor 44 is oriented to the inside of a properly constructed active implantable medical device.

FIG. 10 illustrates an internally grounded bipolar feedthrough filter capacitor 56, such as that disclosed in U.S. Pat. No. 5,905,627 the contents of which are incorporated herein by reference. Even though the capacitor 56 has no outside diameter or outside perimeter metallization, a dendrite 58' can still form if a moisture film and voltage bias form between the lead wire 60 and the ground pin 66 or a dendrite 58 can form between a lead wire 60' and a conductive ferrule 62. In this case, the conductive ferrule 62 has been greatly simplified and shown as a rectangular plate. In the art, these ferrules 62 take on a variety of sizes and shapes, including H-flanges to capture the mating halves of an implantable medical device housing. As shown, the dendrite 58 has formed all the way from the inner diameter termination surface 64 conductive material to the ferrule 62. In an internally grounded feedthrough capacitor 56, there is always a grounded lead wire or pin 66 which is connected to the capacitor's internal electrode plate set 68, illustrated in FIG. 12. It is also possible, or even likely, to form a dendrite 58' between this lead wire and any adjacent lead of opposite polarity. Such a dendrite 58' would short out the lead wire 60 to the grounded lead pin 66. This is why coating such leads, which may be formed of noble metal material, with migratable metals or materials such as tin-lead combinations, is problematic because the dendrites can form and migrate over any migratable conductive material, such as silver-filled conductive thermal-setting connective material which is often used to connect lead wires 60 and 66 to the inside diameter metallization 64 of the feedthrough capacitor or conductively connect the outside of the capacitor 56 to the ferrule 62.

It should be noted that for a dendrite to form, the migratable material need not be present on both sides. In other words, a migratable material is not necessarily both the cathode and the anode. There are no materials in titanium that would migrate, however, silver particles from conductive silver bearing glass frit fired onto the capacitor is capable of migrating in the presence of a voltage bias and a moisture film. It is also possible that a dendrite material form directly between the inside diameter metallizations 64 from the ground feedthrough hole and one or more of the active insulated feedthrough capacitor wires.

Detecting the presence of these dendrites can sometimes be very confusing for the test technician. This is because the dendrites most readily form in a high-impendence, low voltage circuit where a moisture film is present along with migratable materials. The dendrite, metal migration or metal whisker is typically very lacy, thin and of low cross-sectional area. Accordingly, this material can act like a fuse and open up if a high voltage or a low impedance voltage or current source is applied. Accordingly, when dendrites are present, they are sometimes inadvertently blown open by routine electrical testing either by the manufacturer or by the customer's receiving inspection department. A concern is that after years of field use, if the dendrite were to reform, this could slowly degrade the battery life of the medical device through decreased insulation resistance or degrade the device's ability to sense very low level biological signals. These are yet again reasons why it has been common in the prior art to place the ceramic feedthrough capacitor toward the inside where it is protected from body fluids.

FIGS. 13 and 14 show a prior art integrated chip capacitor 70, such as that described in U.S. Pat. Nos. 5,959,829 and 5,973,906, the contents of which are incorporated herein. These chip capacitors 70 come in a variety of sizes and shapes and are used to decouple electromagnetic interference from the lead wires 72 of an implantable medical device to the metallic ferrule 74. As illustrated, capacitor 70 has integrated four rectangular chip style capacitors into a single monolithic package. Each of these chip capacitors makes a connection to a respective lead wire 72 and decouples EMI to the metallic ferrule 74. Since prior art chip capacitors are constructed of the same materials as are typical in the entire capacitor industry, it is likely that a dendrite 76 will form if moisture or solvents are present. Such dendrites 76 can form between the migratable connective materials used to connect the capacitor metallization 78 to the lead wire 72 and the ferrule 74, or between the lead wires 72 (not shown).

It is a common misconception that it takes many months or years for metal migration or dendrites to form. Actually, the dendrite itself has been observed to form very quickly so long as (1) a migratable material, (2) a moisture or solvent film, and (3) a suitable bias voltage from a high impedance source is present. Once these three factors come together, it can be only a matter of seconds or minutes for the dendrite itself to actually form and short out the electronic component or circuit. Dendrites can also form from lead wires to the conductive materials 77 used to connect the capacitor's ground termination to the conductive ferrule. This is the case even if the ferrule is of a non-migratable material such as titanium or a noble metal, such as gold or the like, provided that the connective material 77 is of a migratable material such as silver, tin, or other known migratable metals. Notwithstanding U.S. Pat. No. 6,055,455, the inventors are not aware of a single instance in an implantable medical device where the capacitor has been placed on the outside and exposed to body fluid. Instead, it has been standard practice in the medical implant industry that all electronic components be protected inside the hermetically sealed enclosure, which is typically vacuum evacuated and back filled with an inert gas such as nitrogen or the like to ensure a very dry atmosphere, and prohibit contact with body fluids. Of course, in such a dry atmosphere, one of the three essential ingredients for metal migration or dendrite formation is removed and such dendrites do not form.

Metal migration, whiskers and dendrite formation does not only occur of the surfaces on ceramic feedthrough and chip capacitors. Said dendrites can also form inside the capacitor along microfractures, cracks, or knit line defects (slight separations in the capacitor electrode lamination boundary). Internal metal migration within a ceramic capacitor can have the same catastrophic effects as surface migration. That is, the insulation resistance of the capacitor can be severely reduced including the shorting out of the capacitor completely.

The ceramic feedthrough capacitor which acts as an EMI filter is poised directly at the point of ingress and egress of the lead wires between the implantable medical device and body tissue. For example, in a cardiac pacemaker, the feedthrough capacitor is placed at the point where lead wires from the heart enter into the pacemaker itself. Any short circuiting or lowering of insulation resistance of the ceramic feedthrough capacitor precludes or shorts out the proper operation of the pacemaker itself. This can be very dangerous or even life threatening to a pacemaker-dependent patient whose heart depends on each pulse from a pacemaker so that it itself will beat. There are numerous instances in the literature wherein cardiac pacemakers, implantable defibrillators and neurostimulators have been shown to adversely react in the presence of an emitter such as a cell phone or retail store security gate (electronic article surveillance system). Pacemaker potential responses to EMI include sensing (pacemaker inhibition), noise reversion to asynchronous spacing, tracking for dual chamber devices, in rate adaptive devices the rate changes within programmed rate limits, activation of the lead switch, ICD undersensing, asynchronous pacing, or microprocessor reset. In an implantable cardioverter defibrillator (ICD), potential responses to EMI can include all of the responses for a pacemaker in that ICDs often include a pacemaker function. In addition, ICDs may also respond to EMI by over-sensing that manifests itself as either inhibition or an inappropriate delivery of therapy. An inappropriate delivery of therapy means that a fully alert and cognizant patient would receive a high voltage shock. Delivery of such a high voltage can injure the patient by literally throwing him off his feet (such a case has been documented with the male patient breaking his arm). In addition, ICDs can respond to EMI by tracking, undersending an arrhythmia, or electrical current directly induced in the lead system that can trigger a dangerous cardiac arrhythmia. Accordingly, proper operation of the EMI filter is critical to protect the implantable medical device from not exhibiting any of the possible aforementioned malfunctions. Formation of dendrites can seriously degrade the proper operation of the pacemaker and/or make the filter ineffective at performing its proper function.

For example, with reference to FIGS. 15-17A, a cross-sectional view of a prior art unipolar feedthrough capacitor assembly 79 is shown similar to that described in U.S. Pat. Nos. 4,424,551; 4,152,540; 4,352,951 and others. Monolithic ceramic capacitors have a relatively low thermal coefficient of expansion compared to metals. Ceramic capacitors are very strong in compression, but very weak in tension. This is typical of most brittle materials. Accordingly, it is very easy to introduce cracks within the ceramic capacitor structure if the capacitor is subjected to excessive stresses. The ceramic capacitor assembly shown in FIG. 15 has the ceramic capacitor 87 embedded within a metallic ferrule 80. For a human implant application, this metallic ferrule 80 would typically be made of titanium and could have a variety of shapes and flanges. The connection from the inside diameter of the ferrule 80 to the outside diameter termination surface metallization 82 of the feedthrough capacitor is shown as material 84. Material 84 is typically a thermal-setting conductive adhesive, such as a silver-filled conductive polyimide, epoxy or the like. The entire assembly shown in FIG. 15 is designed to be installed into a pacemaker, ICD or the like by laser welding directly into the titanium can of the implantable device. Accordingly, the ferrule 80 is rapidly heated and tends to expand. The relatively cooler ceramic capacitor 87 does not expand nearly at the same rate. Accordingly, a variety of cracks can be introduced into the ceramic capacitor. These cracks can be axial, radial or cover sheet type features.

For purposes of example, as shown in FIG. 17, a crack 86 has propagated across the corner of the ceramic capacitor 87. Additionally, the crack 86 has contacted plates 88 and 90 of opposite polarity. In other words, the crack 86 has propagated through the main body of the ceramic dielectric 92 between a ground electrode plate 88 and the lower active electrode plate 90. This in and of itself does not present an immediate electrical defect. The reason for this is that as long as the crack 86 itself does not contain metallic particles, the two electrodes 88 and 90 are not shorted out. However, it is quite possible for these cracks to propagate to the outside diameter or top surface of the capacitor 87. Long-term exposure to body fluid in combination with the bulk permeability of the surrounding polymers can lead to the presence of a moisture thin film that lines the inside of this crack 86. FIG. 17A shows a silver dendrite 86' that has formed by metal migration through the crack. The reason for the formation of the dendrite has to do with the intrinsic materials that are typically used in the prior art electrodes and capacitor terminations themselves. Ceramic capacitors are typically made with nickel, silver or palladium silver electrodes. These are low cost electrode systems that are found in many ceramic capacitors today. They are formed within the solid monolithic ceramic by firing or sintering at a relatively low temperature (around 1100° C.). An internal dendrite is a highly undesirable situation to occur because it may short out the capacitor 87. Such shorting or reduced insulation resistance of the ceramic capacitor 87 not only degrades its effectiveness as an EMI filter, it also can cause the catastrophic failure of the entire implantable medical device. As mentioned, this can be life threatening, for example, in the case of a pacemaker-dependant patient. The dendrite 86' can be low enough in resistance to short out the pacemaker output pulse. In this case, the patient's heart would simply stop beating, which would quickly lead to death.

There is an emerging need for passive circuit elements that are directly exposed to body fluids at locations along implanted leads and/or in implanted sensors which are remote from the active implantable medical device during diagnostic procedures such as magnetic resonance imaging (MRI), it is important to prevent excessive currents from flowing in the implanted leads such that the leads or their distal electrodes could overheat and damage body tissue.

In the past, passive circuit elements such as resistors, inductors and capacitors have been enclosed within a hermetic seal. However, there are a number of negatives associated with the hermetic seal. One is, as a practical matter, the hermetic seal ends up being larger than the individual capacitor and filter components themselves. When threading the leads in the human body, particularly into the left ventricular area, or tunneling leads, for example, to a deep brain stimulator, it is important that the leads be as small as possible. A second negative associated with a hermetic seal is it adds greatly to the packaging complexity and the cost.

Accordingly, there is a need to have all components of a passive or an active electronic device be biocompatible and non-migratable in the presence of electrical bias and body fluids. Additionally, there is a need for internal and external electrical attachments of all non-hermetically sealed passive or active components. Additionally, there is a need for biocompatible and non-migratable internal and external electrical attachments of all non-hermetically sealed passive or active components. For example, one is referred to electrical connection material 26 shown in FIG. 3. If the feedthrough capacitor 30 is entirely biocompatible but the electrical connection material 26 is not, this could still be very problematic. For example, if connection material 26 was a silver-filled thermal-setting conductive epoxy or polyimide, those silver particles could migrate under the presence of voltage bias in body fluid and moisture thereby resulting in a metal whisker or a dendrite and thereby creating a low impedance or even a short circuit. On the other hand, if electrical connection material 26 was a lead-bearing solder, the lead could leech into body fluids and become toxic to body tissues. Similar analogies apply to other electronic components, including bandstop filters, diodes, multiplexers, inductors, resistors, transistors, microchips, electronic networks and the like, such as those shown and described in U.S. Pat. No. 7,363,090, U.S. patent application Ser. Nos. 12/337,170, (U.S. Patent Application Pub. No. 2009/0163980, now abandoned); 12/337, 376, (U.S. Patent Application Pub. No. 2009/0163981); and 11/943,419, (U.S. Pat. No. 7,804,676); U.S. Patent Application Publication Nos. 2008-0116997, 2008-0132987, 2008-0161886, 2008-0049376, 2008-0071313, 2007-0112398, 2005-0197677, and 2006-0085043; and U.S. Provisional Patent Application No. 61/179,693, the contents all of which are incorporated herein.

Moreover, there is a need for a biocompatible and non-migratable electrical connection material and/or biocompatible thermal-setting conductive attachment material which can be used in combination with any passive or an electronic component or network, including combinations of capacitors, inductors, resistors, frequency selective networks, such as bandstop filters, transistors, microchips, RFID chips, lead based sensors, diodes, multiplexers, MEMs devices and the like. The present invention fulfills these needs and provides other related advantages.

SUMMARY OF THE INVENTION

In accordance with the present invention, an implantable passive or active electronic network component or component network is provided which is suitable for prolonged direct body fluid exposure and is attachable to a conductive surface, circuit trace, lead or electrode. The electronic network component or component network comprises (1) a non-conductive body of biocompatible and non-migratable material, (2) a conductive termination surface of biocompatible and non-migratable material associated with the body, and (3) a connection material of biocompatible and non-migratable material for conductively coupling the termination surface to the conductive surface, circuit trace, lead or electrode.

In preferred embodiments, the connection material comprises a thermal-setting adhesive such as a polymer selected from the group consisting of epoxies, polyimides, polyethylene oxide, polyurethane, silicone, polyesters, polycarbonate, polyethylene, polyvinyl chloride, polypropylene, methylacrylate, para-xylyene, and polypyrrhol. The adhesive preferably includes a biocompatible metal filler such as a noble metal filler such as titanium, platinum and platinum/iridium alloys, tantalum, niobium, zirconium, hafnium, nitinol, Co—Cr—Ni alloys such as MP35N, HAVAR® (a cobalt base alloy) and ELGILOY® (a Co—Cr—Ni alloy), stainless steel, gold, ZrC, ZrN, TiN, NbO, TiC, TaC, Indium Oxide/Indium Tin Oxide.

The termination surface comprises a noble metal or a noble metal composition, or other non-migratable and biocompatible material such as titanium, platinum and platinum/iridium alloys, tantalum, niobium, zirconium, hafnium, nitinol, Co—Cr—Ni alloys such as MP35N, HAVAR® and ELGILOY®, stainless steel, gold, ZrC, ZrN, TiN, NbO, TIC, TaC, Indium Oxide/Indium Tin Oxide.

The biocompatible connection material comprises a brazing, welding or soldering material selected from the group consisting of titanium, platinum and platinum/iridium alloys, tantalum, niobium, zirconium, hafnium, nitinol, Co—Cr—Ni alloys such as MP35N, HAVAR® and ELGILOY®, stainless steel, gold, ZrC, ZrN, TiN, NbO, TiC, TaC, Indium Oxide/Indium Tin Oxide (Transparent Conductive Oxides), gold-bearing glass frit, TiCuSil, CuSil, and gold-based braze. The adhesive may adhere at least a portion of the electronic network component or component network to the conductive surface, circuit trace, lead or electrode.

The electronic network component may comprise a capacitor, a resistor, an inductor, a diode, a transistor, an electronic switch, a MEMs device, or a microchip.

The capacitor includes first and second sets of biocompatible and non-migratable electrode plates embedded within the body, wherein each set of electrode plates is conductively coupled to a respective conductive termination surface. Preferably the first and second sets of electrode plates comprise a noble metal or noble metal composition such as gold, platinum, a gold-based alloy, or a platinum-based alloy.

The inductor comprises at least one biocompatible and non-migratable circuit trace on a surface of the body, which extends from a first biocompatible and non-migratable termination surface to a second biocompatible and non-migratable termination surface. The inductor circuit trace preferably comprises a noble metal or a noble metal composition such as gold, platinum, a gold-based alloy or a platinum-based alloy. In another embodiment, the inductor may comprise at least one biocompatible and non-migratable circuit trace embedded within the body and extending from a first biocompatible and non-migratable termination surface to a second biocompatible and non-migratable termination surface. Again, the inductor circuit trace preferably comprises a noble metal or a noble metal composition such as gold, platinum, gold-based alloy or a platinum-based alloy.

The aforementioned capacitor may be placed in parallel with the inductor to form a bandstop filter in accordance with the present invention.

The resistor preferably comprises a biocompatible and non-migratable circuit trace on a surface of the body which extends from a first biocompatible and non-migratable termination surface to a second biocompatible and non-migratable termination surface. The resistor circuit trace preferably comprises a noble metal or a noble metal composition such as gold, platinum, a gold-based alloy or a platinum-based alloy. In another embodiment, the resistor comprises at least one biocompatible and non-migratable circuit trace embedded within the body and extending from a first biocompatible and non-migratable termination surface to a second biocompatible and non-migratable termination surface. Again, the resistor circuit trace preferably comprises a noble metal or a noble metal composition such as gold, platinum, a gold-based alloy or a platinum-based alloy.

The diode preferably comprises at least one bio-compatible and non-migratable circuit trace embedded within the body and extending from a first biocompatible and non-migratable termination surface to a second biocompatible and non-migratable termination surface. The diode circuit trace preferably comprises a noble metal or a noble metal composition such as gold, platinum, a gold-based alloy or a platinum-based alloy.

Likewise, the electronic switch preferably comprises at least one biocompatible and non-migratable conductor embedded within the body and extending from a first biocompatible and non-migratable termination surface to a second biocompatible and non-migratable termination surface. The electronic switch conductor preferably comprises a noble metal or a noble metal composition such as gold, platinum, gold-based alloy or a platinum-based alloy.

The MEMs device preferably comprises at least one MEMs conductor embedded within the body and extending from a first biocompatible and non-migratable termination surface to a second biocompatible and non-migratable termination surface. The MEMs conductor preferably comprises a noble metal or a noble metal composition such as gold, platinum, a gold-based alloy or a platinum-based alloy.

The transistor preferably comprises at least one biocompatible and non-migratable circuit trace embedded within the body and extending from a first biocompatible and non-migratable termination surface to a second biocompatible and non-migratable termination surface. The transistor circuit trace preferably comprises a noble metal or a noble metal composition such as gold, platinum, a gold-based alloy or a platinum-based alloy.

The microchip preferably comprises at least one biocompatible and non-migratable circuit trace embedded within the body and extending from a first biocompatible and non-migratable termination surface to a second biocompatible and non-migratable termination surface. The microchip circuit trace preferably comprises a noble metal or a noble metal composition such as gold, platinum, a gold-based alloy or a platinum-based alloy.

The electronic network component or component network may include a plurality of conductive circuit traces within the non-conductive body. Such conductive circuit traces preferably comprise a biocompatible and non-migratable material such as gold, platinum, a gold-based alloy or a platinum-based alloy. An adhesive of biocompatible and non-migratable material is preferably utilized for conductively coupling at least two of the plurality of the conductive circuit traces together such as, for example, a multilayer conductor.

In another preferred embodiment, the microchip may comprise an RFID inlet. An adhesive of biocompatible and non-migratable material is preferably utilized for conductively coupling the RFID inlet to an associated antenna.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 15 is a cross-sectional view of a prior art unipolar capacitor, having cracks and dendritic growth between electrodes thereof;

FIG. 16 is an electrical schematic diagram of the capacitor of FIG. 15;

FIG. 17 is an enlarged view of area 17 of FIG. 15, illustrating the crack and dendritic growth between electrodes;

FIG. 17A is an enlarged view of area 17A of FIG. 17, illustrating dendritic growth within the crack;

FIG. 36 is a perspective view of an internally grounded biopolar capacitor layered with glass in accordance with the present invention;

FIG. 37 is a perspective view of a hermetic terminal, having terminal pins or lead wires extending therethrough;

FIG. 38 is an electrical schematic diagram of the capacitor of FIG. 36;

FIG. 39 is a cross-sectional view illustrating the configuration of active electrode plates in the capacitor of FIG. 36;

FIG. 40 is a cross-sectional view illustrating the configuration of ground electrode plates in the capacitor of FIG. 36;

FIG. 66 is a table showing the relationship between French sizes and millimeters and inches;

FIG. 90 is an electrical schematic illustration of the MEMs switch assemblies shown in FIGS. 87, 88 and 89;

FIG. 91 is a line schematic drawing showing an electronic multiplexer which can be used to select optionally electronic switches or L-C bandstop TANK filters;

FIG. 92 is an electrical schematic illustration of a typical PNP transistor which can be used as part of the electronic switches shown in FIG. 91;

FIG. 93 is an perspective view of an inductor chip attached to opposing circuit traces;

FIG. 94 is an exploded perspective view of the various layers of the inductor chip of FIG. 93;

FIG. 95 is an electrical schematic illustration of the inductor chip shown in FIGS. 93 and 94.

DETAILED DESCRIPTION OF THE PREFERRED EMBODIMENTS

Figure 1:
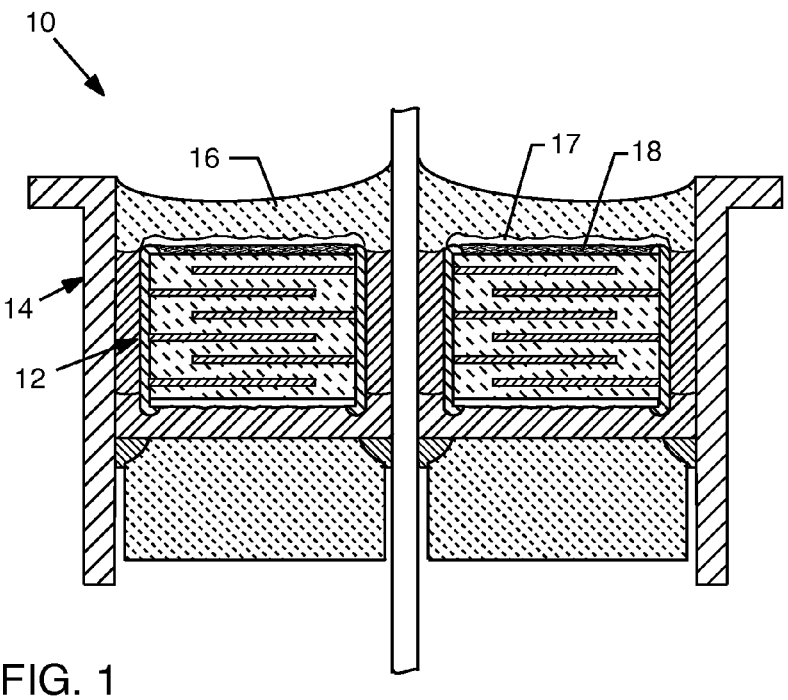
FIG. 1 is a cross-sectional view of a prior art unipolar capacitor having an adhesive seal on a top surface thereof, illustrating a small separation formed between a sealing material and a top surface of the capacitor where dendrites may form.
Figure 2:
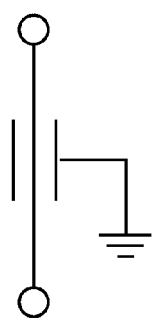
FIG. 2 is an electrical schematic diagram of the capacitor of FIG. 1.
Figure 3:
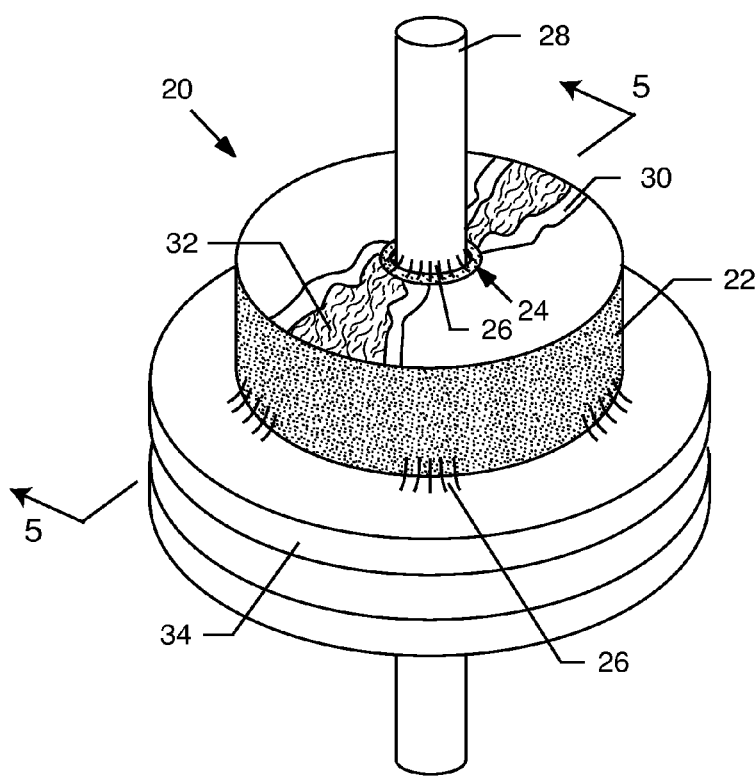
FIG. 3 is a perspective view of a prior art unipolar feedthrough capacitor mounted to a hermetic terminal of an implantable medical device, and having dendritic growth thereon.
Figure 5:
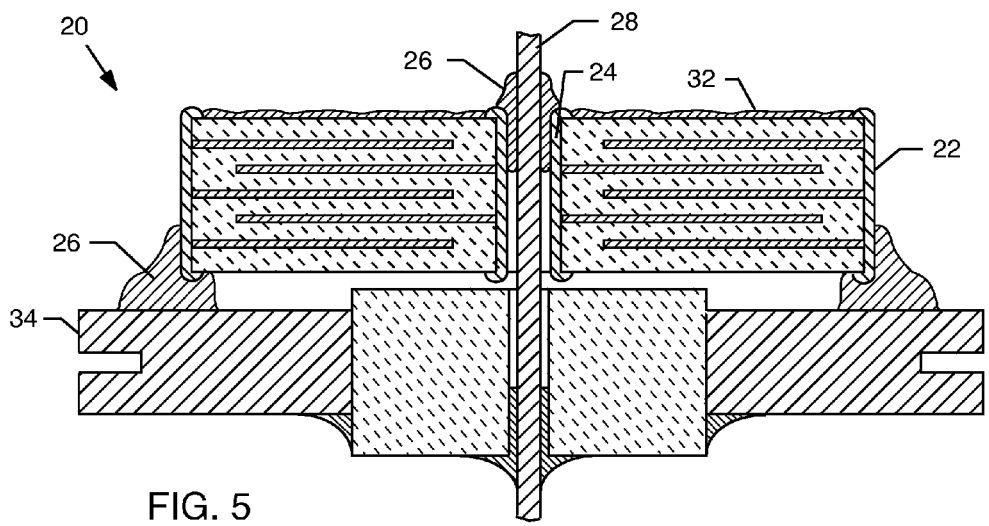
FIG. 5 is a cross-sectional view taken generally along line 5-5 of FIG. 3, illustrating internal components of the capacitor assembly.
Figure 6:
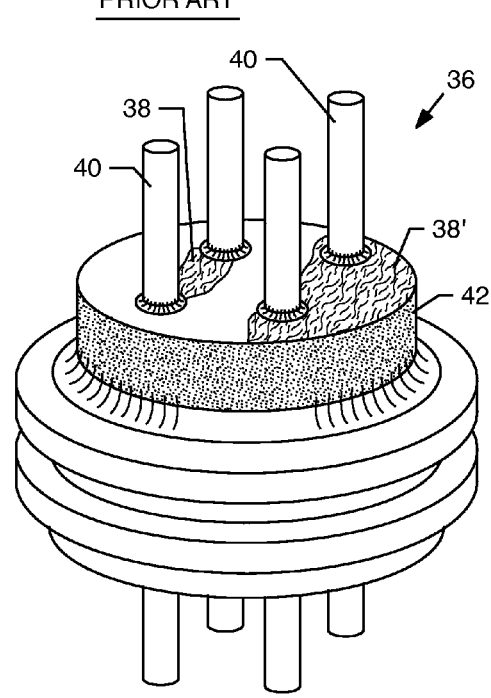
FIG. 6 is a perspective view of a prior art surface mounted quadpolar capacitor, illustrating dendritic growth between lead wires and/or lead wires and ground thereof.
Figure 4:
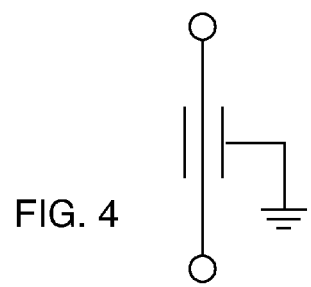
FIG. 4 is an electrical schematic diagram of the capacitor of FIG. 3.
Figure 7:
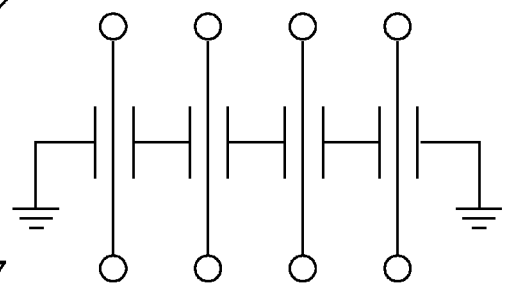
FIG. 7 is an electrical schematic diagram of the capacitor of FIG. 6.
Figure 8:
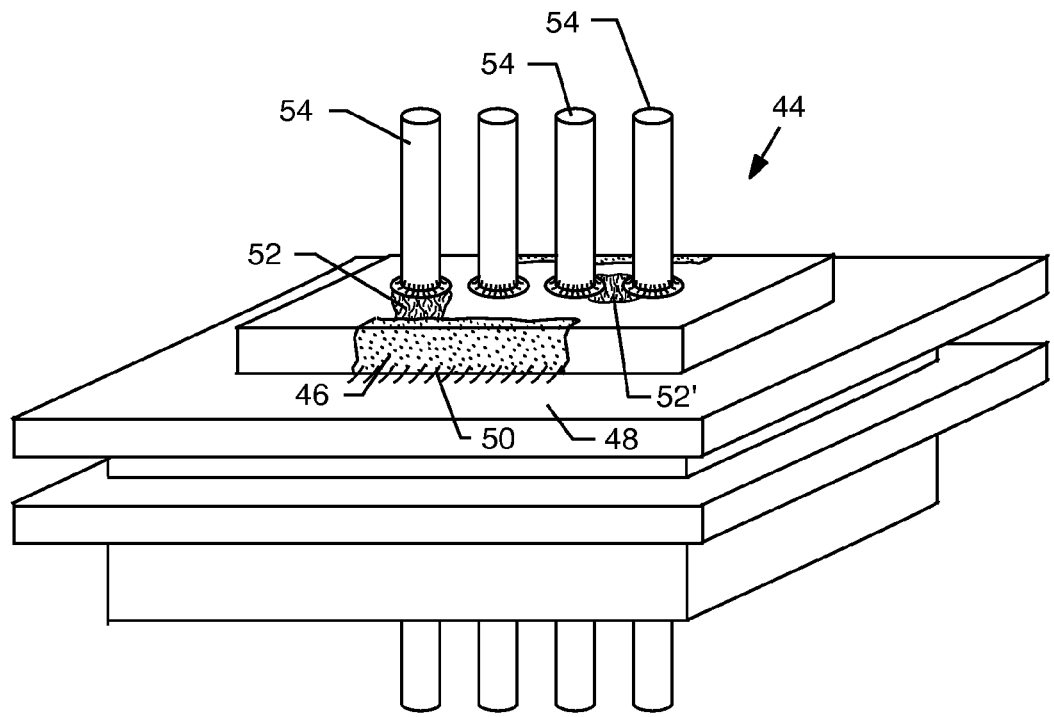
FIG. 8 is a perspective view of a prior art in-line quadpolar capacitor, illustrating dendritic growth between conductive portions thereof.
Figure 9:
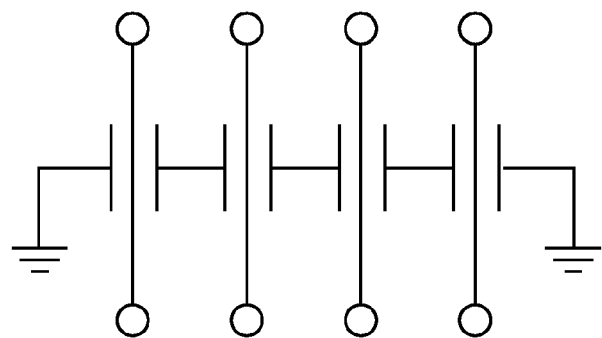
FIG. 9 is an electrical schematic diagram of the capacitor of FIG. 8.
Figure 10:
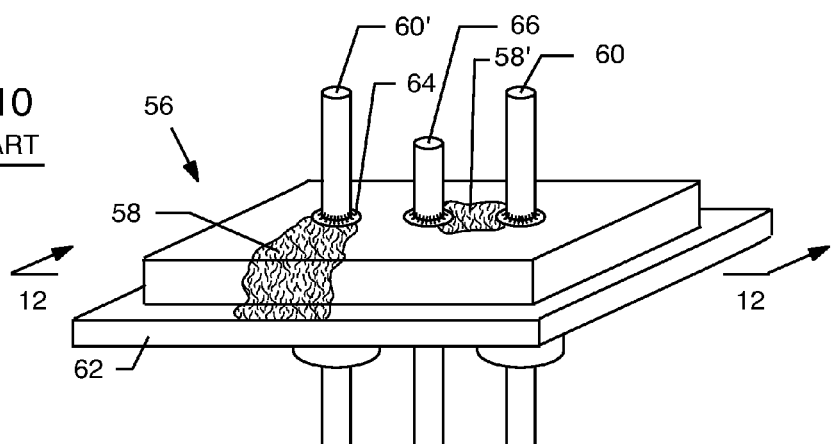
FIG. 10 is a perspective view of a prior art internally grounded bipolar feedthrough capacitor having dendritic growth between conductive portions thereof.
Figure 11:
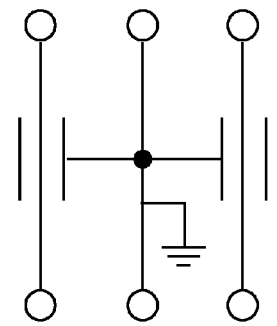
FIG. 11 is an electrical schematic diagram of the capacitor of FIG. 10.
Figure 12:
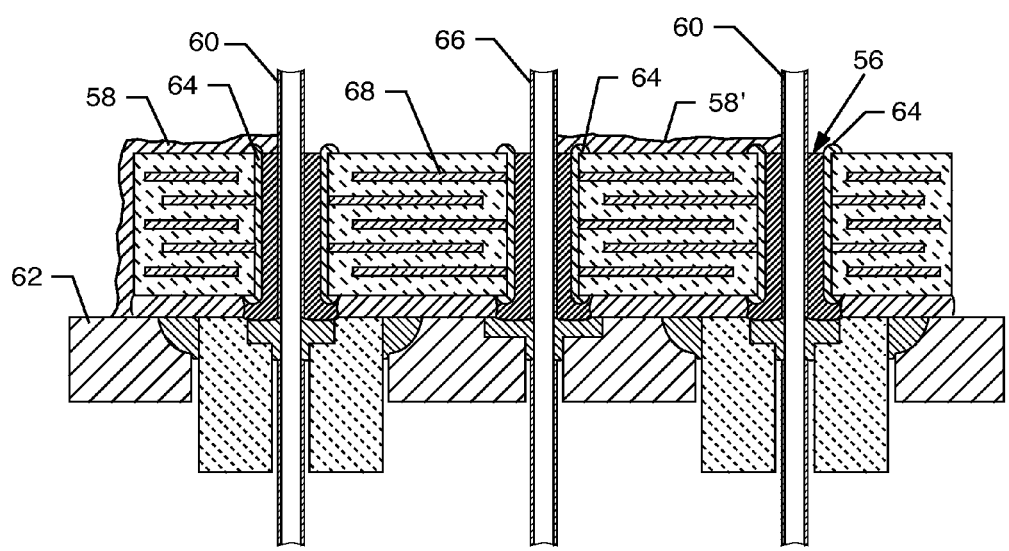
FIG. 12 is a cross-sectional view taken generally along line 12-12 of FIG. 10, illustrating internal components thereof and dendritic growth formed thereon.
Figure 13:
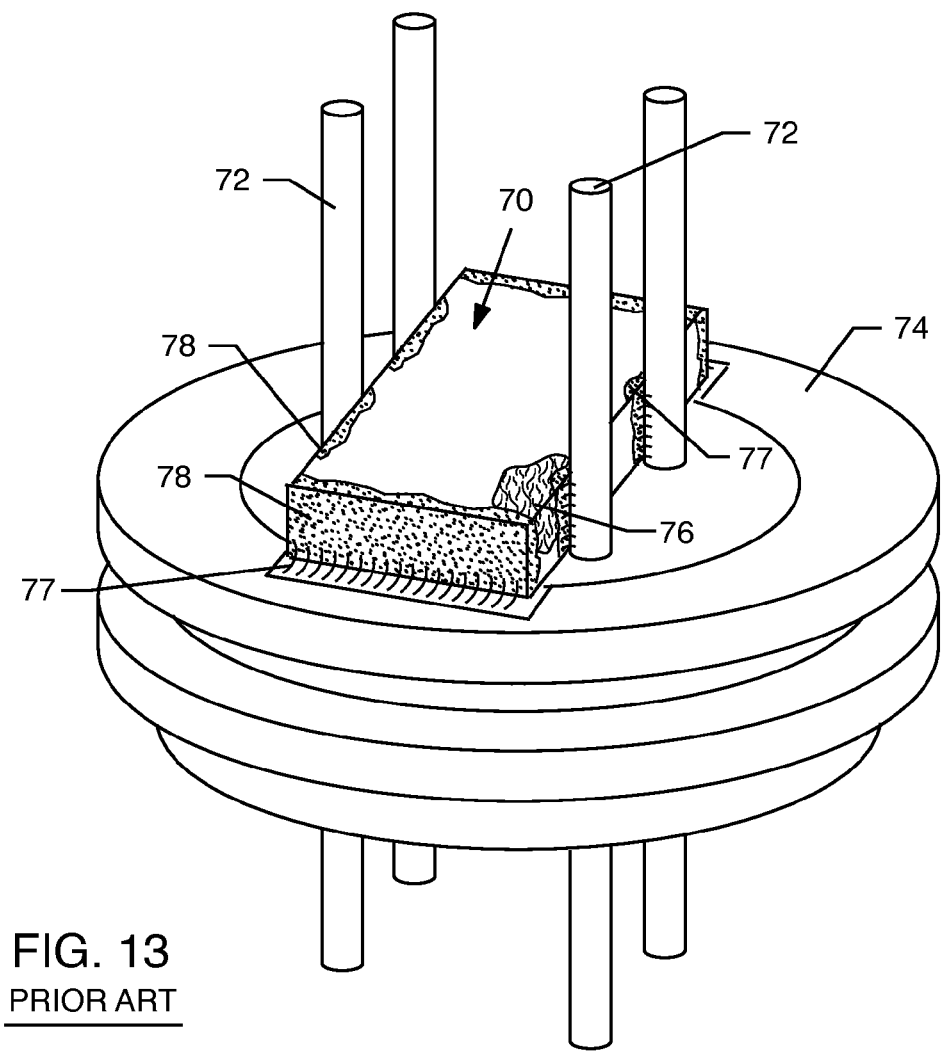
FIG. 13 is a perspective view of a prior art integrated chip capacitor having dendritic growth thereon.
Figure 14:
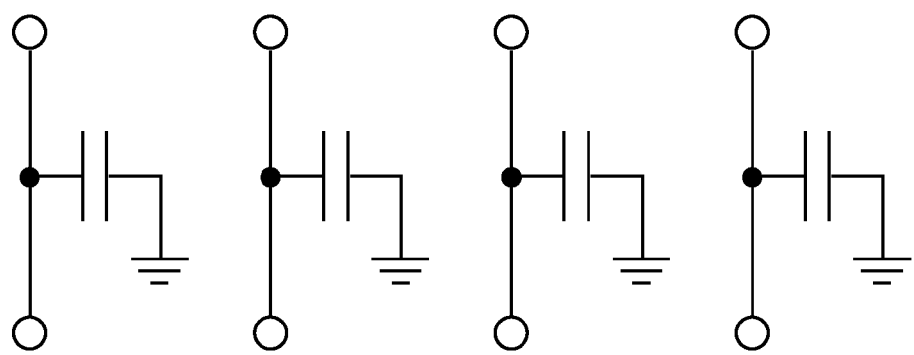
FIG. 14 is an electrical schematic diagram of the chip capacitor of FIG. 13.

As shown in the accompanying drawings for purposes of illustration, the present invention resides in active or passive electronic network components or component networks assemblies such as capacitors, resistors, inductors, frequency selective networks such as bandstop filters, diode or diode arrays, RFID chip-antenna assemblies, microchips, multiplexers, electronic switches, MEMs devices or the like, which are adapted for direct body fluid exposure. Moreover, the present invention resides in novel biocompatible electrical connection materials which can be used to connect externally or internally to any of the aforementioned active or passive electronic network components or component networks, including connections to conductive surfaces, circuit traces, leadwires or electrodes. As used herein, electrodes can include, for example, the internal electrodes of a capacitor, such as a feedthrough capacitor or MLCC or an electrode in contact with body tissue for the purposes of either stimulating said body tissue or sensing biologic signals. An example of a tissue stimulating electrode would be a pacemaker lead and electrode placed into the right ventricle of the human heart.

As noted above, three ingredients are needed for catastrophic or latent metal migration defects to occur in an implanted medical device: 1) the presence of a migratable material, which may include silver, tin, and many other materials; 2) a migratable medium, such as a thin film of moisture or solvent; and 3) an activation energy such as an applied voltage. On the outside of an active implantable medical device (AIMD), such as a cardiac pacemaker which is implanted in body fluid and has a small output voltage, two of these three elements are always present; that is, the migratable medium and the activation energy. Activation energy is present in most active implantable medical devices, including cardiac pacemakers, implantable cardioverter defibrillators, neuro-stimulators, cochlear implants, and the like.

The use of solders to make the electrical connection between the active or passive electronic component or component network and its associated conductive surfaces, circuit traces, leadwires or electrodes is generally ruled out. The reason for this is that most solders contain either lead or tin, both of which are not biocompatible. The problems with lead are obvious from all of the literature regarding lead poisoning in the human body. Tin is ruled out because it is not biocompatible plus it will readily form whiskers or dendrites. Even exotic gold alloy solders still usually contain a percentage of tin or lead, which rules them out for similar reasons. The trouble with other conducting materials such as a conductive polyimide or conductive epoxy is that the polymer is loaded with a silver powder, such as a silver flake or a silver sphere, which is not tightly bound up chemically and is free to migrate. This is also true of the prior art ceramic capacitor metallization materials. For example, a silver bearing glass frit which is fired onto the capacitor will readily form a dendrite. Accordingly, it is a novel feature of the present invention that the third ingredient, namely, migratable materials exposed to the migratable medium, be removed. Thus, one aspect of the present invention resides in an active or passive electronic component or component network whose electrical connections are adapted for direct body fluid exposure by being constructed of biocompatible and non-migratable materials, particularly in locations where body fluid exposure occurs.

The active or passive electronic component or component network may also include a protective barrier, preferably glass or a non-conductive polymer coating, which helps to prevent the body fluid from contacting such conductive and critical portions of the capacitor assembly. Although low temperature glasses are not truly hermetic over long periods of time, adjunct seals such as glass or polymers may be used in conjunction with biocompatible and non-migratable materials of the present invention to provide an added degree of protection.

Thus, in general, the active or passive electronic component or component network assembly which is adapted for direct body fluid exposure comprises biocompatible and non-migratable materials, as well as the electrical connection to adjoining surfaces, circuit traces, leadwires or electrodes.

Biocompatible metals and alloys that can be used for the electronic network components or component network or the connection materials include all of the metals and alloys of titanium, platinum and platinum iridium alloys, tantalum, niobium, zirconium, Hafnium, nitinol, Co—Cr—Ni alloys such as MP35N, HAVAR®, ELGILOY®, stainless steel and gold. There are also a number of conductive metal compounds that can be used including ZrC, ZrN, TiN, NbO, TIC, TaC, and indium Oxide/indium Tin Oxide (Transparent. Conductive Oxides). Commercially available biocompatible electrically conductive epoxies are manufactured by Epoxy Technology, Inc, in Billerica, Mass. For example Epoxy technology EPO-TEK H81 features a biocompatible epoxy which is gold filled (www.epotek.com).

A biocompatible and non-migratable electrical connection material can also be used to connect a terminal pin or a tissue stimulating electrode to a circuit trace or conductive surface of the electronic network component or component network.

The conductive connection materials are typically thermal-setting, brazing, welding or special biocompatible soldering materials. So as to be non-migratable, these materials are selected from the group consisting of: gold, gold alloy, platinum, gold-filled-thermal-setting conductive material, platinum-filled-thermal-setting conductive material, gold-bearing glass frit, TiCuSil, CuSil, and gold-based braze.

Table 1 below shows a more comprehensive list of polymers that can also be filled with any of the biocompatible metals mentioned above. This list can include a variety of epoxies and polyimide materials in addition to polyethylene oxide with ionic additions such as NaCl or any of the other commonly used implantable polymers including polyurethane, silicone, polyesters, polycarbonate, polyethylene, polyvinyl chloride, polypropylene, methylacrylate, para-xylylene and polypyrrhol. As mentioned, any of these can be made conductive with a biocompatible material, for example, by adding a particulate filler such as platinum or gold flake, spheres or powder. There are other materials that could be used including pyrolytic carbon and Tra-Duct 2902 conductive adhesive.

All of the aforementioned considerations and characteristics of the electronic network components or component network are also applicable to internal connections of the individual electrical network components themselves. In particular, the passive electrical network components, which include capacitors, inductors, transistors, microchips, resistors, RFID chip-antenna assemblies, and frequency selective networks such as bandstop filters, are preferably manufactured entirely of biocompatible materials in accordance with the present invention. This way they can be disposed within the lead systems of an active implantable medical device (AIMD) without the need for a separate hermetic seal casing, which is expensive and substantially increases the size of the implanted device, which is highly undesirable.

Figure 18:
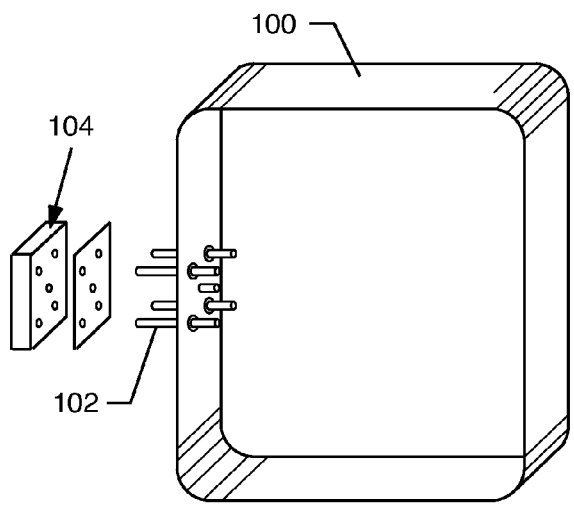
FIG. 18 is a diagrammatic view of an EMI filter assembly disposed on the outside of a hermetically sealed can used in medical devices, in accordance with the present invention.
Figure 19:
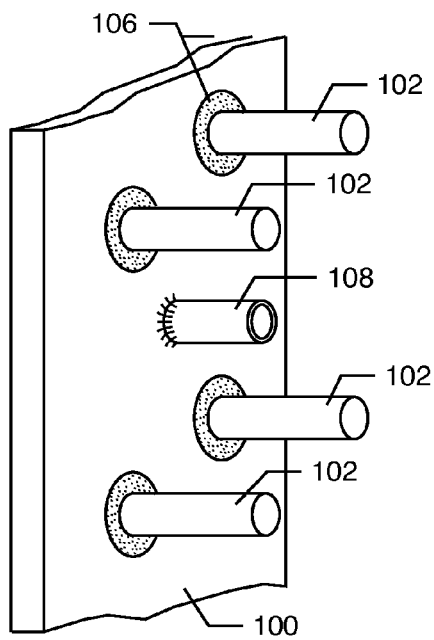
FIG. 19 is a partially fragmented and enlarged perspective view of leads extending from the can of FIG. 18.
Figure 20:
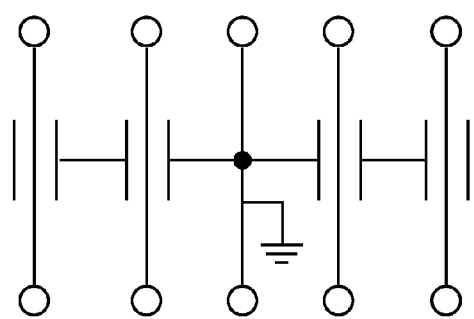
FIG. 20 is an electrical schematic diagram of the assembly of FIG. 18.

With reference to FIGS. 18-20, a metal can or housing 100 is illustrated which is exemplary of those used to enclose the electronics of an implantable medical device, such as a pacemaker or the like. These electronics typically include a battery, a circuit board, integrated circuits, and a variety of other components and sensors (not shown). In the prior art, as described above, a capacitor is disposed within the housing 100, which is closed, such as by welding, and hermetically sealed to protect all of the interior electronic components from the intrusion of body fluids or other contaminants. Terminal pins or lead wires 102 extend into the housing 100 in insulative relationship with the housing and pass through an EMI feedthrough filter capacitor, as is well-known in the art.

However, in accordance with the present invention, the feedthrough capacitor 104 can be disposed outside of the housing 100, advantageously saving space on the inside of the unit housing 100. In order to accomplish this, the feedthrough capacitor 104, or any other active or passive electronic network component or component network, and the lead wires 102 are all formed of biocompatible and non-migratable materials, such as noble metals, which do not migrate in the presence of an electrical bias and body fluid.

Another feature of the present invention is that all of the internal and external electrical connections of said capacitor or any active or passive electronic network component or component network embody electrical connection materials to adjoining surfaces, circuit traces, leadwires or electrodes, that are also designed of biocompatible and non-migratable materials.

In FIG. 19, an enlarged view of the lead wires 102 extending through the housing 100 is shown. Each of the lead wires 102 is in insulative relationship with the housing 100 by insulating material 106, which is shown for illustrative purposes. There are a variety of methodologies that can be used to maintain the four lead wires 102 in non-insulative relationship with the metallic can or housing 100. These include the use of alumina insulators, glass seals, or a ferrule or individual unipolar ferrules with gold-brazed alumina insulators. The center ground pin 108 may be hollow, as illustrated, whereby after hermetic sealing by laser welding of the lid of the housing (not shown) one could then use the hollow ground pin 108 to pull a vacuum and then back fill the inside with dry nitrogen. While still in a nitrogen tank, hollow tube 108 would then be hermetically sealed by welding, ball insertion or the like. The capacitor illustrated in FIG. 18 is of the internally grounded type, which simplifies the assembly. However, it is not necessary that the capacitor 104 be of internally grounded construction, but rather surface mounted technology may be used such as that described by U.S. Pat. No. 5,333,095 or other capacitor types so long as they are constructed of materials in accordance with the present invention so that the capacitor can be disposed in direct contact with body fluids outside of the housing 100 of the medical device.

Figure 21:
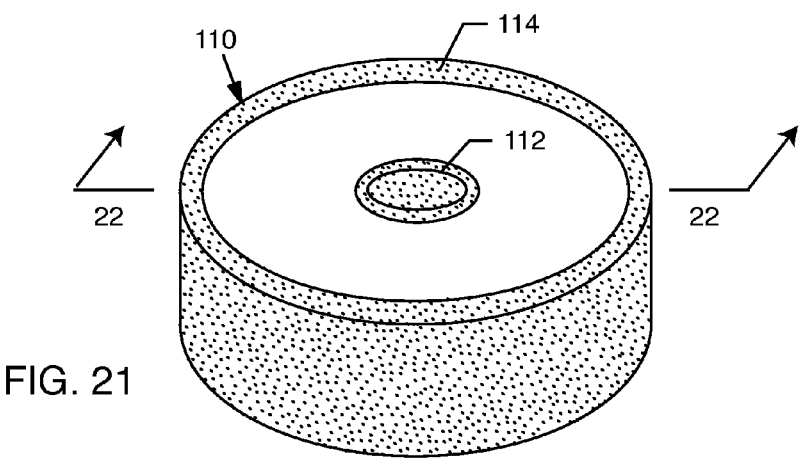
FIG. 21 is a perspective view of a unipolar capacitor comprised of non-migratable materials in accordance with the present invention.

FIG. 21 illustrates a monolithic feedthrough ceramic capacitor 110 having metallization of non-migratable materials on an inner terminal surface 112 and an outer terminal surface 114. The capacitor 110 may be constructed using conventional manufacturing methods, in terms of silkscreen, punching, hole drilling, and the like. However, the metallization materials for the inner and outer termination surfaces 112 and 114 are typically comprised of a noble metal or alloy, such as pure gold, pure platinum, or the like. Other metals include titanium, platinum/iridium alloys, tantalum, niobium, zirconium, hafnium, nitinol, stainless steel and Co—Cr—Ni alloys such as MP35N, HAVAR® and ELGILOY®. See Table 1 below. These metals are biocompatible and are also known to not migrate or form dendrites in the presence of moisture or body fluid solutions. It should be understood that the termination surfaces 112 and 114 can be coated with the noble metals or alloys which are non-migratable, or comprised entirely of such metals. The important aspect is that those portions that are potentially in contact with moisture be of non-migratable material to prevent dendritic growth.

TABLE 1

LIST OF CONDUCTIVE, ATTACHABLE, NON-MIGRATING BIOCOMPATIBLE MATERIALS

| Metals and Alloys | Conductive Metal Compounds | Polymers* |
|---|---|---|
| Titanium | ZrC | Polyethylene Oxide with ionic addition such as NaCl (see U.S. Pat. No. 6,295,474) |
| Platinum and platinum/iridium alloys | ZrN | Polyurethane |
| Tantalum | TiN | Silicone |
| Niobium | NbO | Polyesters |
| Zirconium (often used in knee joint replacements) | TiC | Polycarbonate |
| Hafnium | TaC | Polyethylene |
| Nitinol | Indium Oxide/ Indium Tin Oxide (Transparent Conductive Oxides) | Polyvinyl Chloride |
| Co—Cr—Ni alloys such as MP35N, Havar ®, Elgiloy ® | | Polypropylene |
| Stainless Steel | | Methylacrylate |
| Gold (has been used as a stent coating) | | Para-xylylene |
| | | Polypyrrhol |
| | | Epoxies |
| | | Polyimides |

*Any of the commonly used implantable polymers mentioned above can be made conductive by adding a particulate filler such as Pt powder.
Others: Pyrolytic carbon and Tra-Duct 2902 conductive adhesive.

Figure 22:
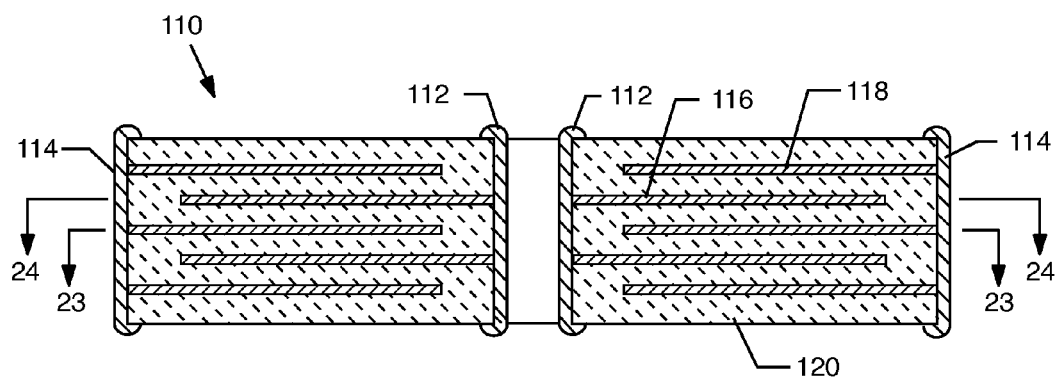
FIG. 22 is a cross-sectional view taken generally along line 22-22 of FIG. 21.

FIG. 22 is a cross-section of the unipolar feedthrough capacitor of FIG. 21, taken along line 22-22.

Figure 23:
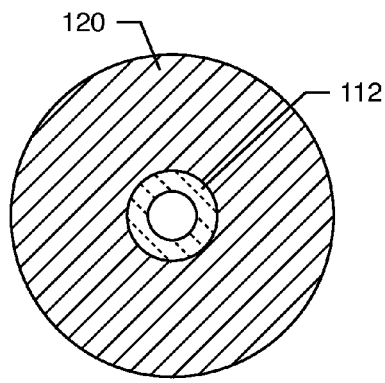
FIG. 23 is a cross-sectional view of the capacitor of FIGS. 21 and 22 along the line 23-23 in FIG. 22, illustrating the layout of conductive ground electrode plates therein.
Figure 24:
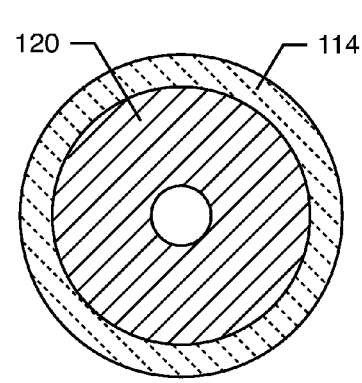
FIG. 24 is a cross-sectional view taken along the line 24-24 in FIG. 22, illustrating the layout of active electrode plates therein.

Within the capacitor 110 are active 116 and ground 118 electrodes (see, respectively, FIGS. 23 and 24). Cracks can form in the non-conductive or dielectric material 120 filling the capacitor 110 and separating the electrodes 116 and 118, thus possibly leading to dendritic growth between the electrodes 116 and 118. In accordance with the present invention the electrodes 116 and 118 are also formed of a biocompatible and non-migratable material. Preferably, these electrodes 116 and 118 are constructed of platinum or a platinum alloy. The use of platinum electrodes 116 and 118 enables the capacitor to be a high fire capacitor. That is, the capacitor would have to be sintered at a much higher temperature than is typically used in the industry. However, there are other materials which could be used which would form suitable alloys that would not tend to migrate. For example, a ternary system, comprised of an alloy of gold, platinum palladium, could be used. The use of ternary electrodes is known, however, never in combination with the other material described herein and never used in a human implant application where direct body fluid exposure would be expected.

Figure 25:
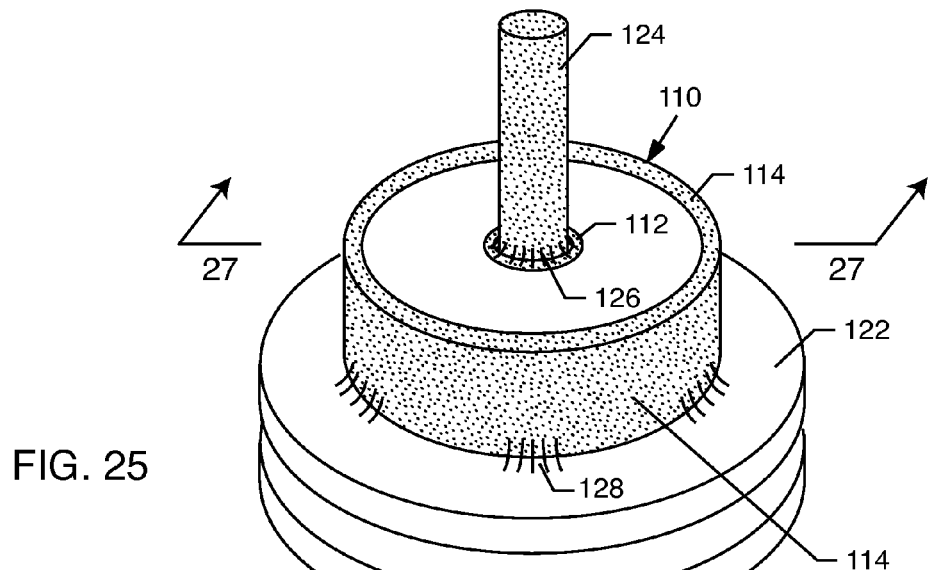
FIG. 25 is an isometric view of the capacitor of FIG. 21, having a lead wire extending therethrough and attached to a hermetic terminal of a human implantable electronic device.
Figure 26:
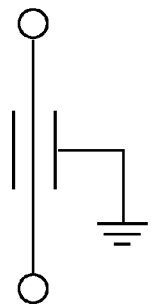
FIG. 26 is an electrical schematic diagram of the assembly of FIG. 25.
Figure 27:
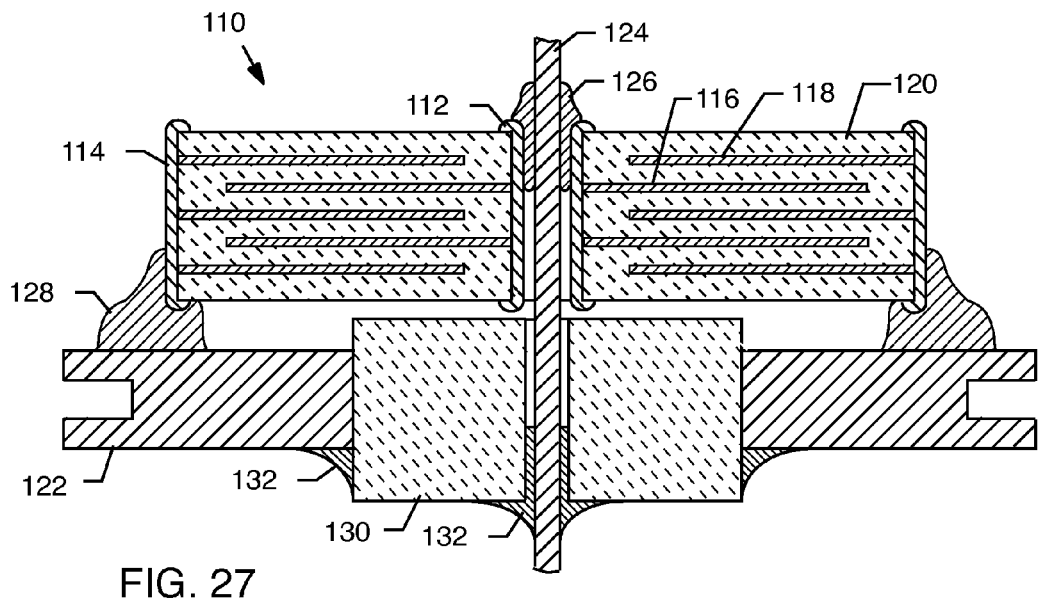
FIG. 27 is a cross-sectional view taken generally along line 27-27 of FIG. 25, illustrating internal components thereof and the use of non-migratable materials.

With reference to FIGS. 25-27, the unipolar capacitor 110 is installed to a hermetic terminal 122, such as a ferrule, of a human implantable electronic device. A lead wire or terminal pin 124 extends through the capacitor 110, the purpose of the capacitor 110 being to prevent EMI from disturbing or interrupting the function of internal circuitry and components of the implantable medical device. The hermetic terminal or ferrule 122 is typically comprised of titanium or the like. While not of a noble metal or alloy thereof, titanium is biocompatible and is not migratable. The lead wire 124 should be coated with or solidly formed of a biocompatible and non-migratable material, typically gold or platinum or its alloys.

The electrical connecting material 126 between the lead wire 124 and the inner termination surface 112 must also be made of biocompatible material that cannot migrate or form dendrites. Similarly, the electrical connection 128 between the outer termination surface 114 and the ferrule 122 must also be comprised of a biocompatible, bio-stable, non-migratable material. Such electrical connections 126 and 128 are typically comprised of thermal-setting conductive adhesives, welding or soldering materials. In a preferred embodiment, such thermal-setting conductive epoxies or polyimides would comprise gold, platinum or other biocompatible metals as a conductive filler. Said fillers may be in powder form. Other suitable filler materials include platinum, or platinum coated spheres or flakes of niobium or tantalum. As the electronic network component or component network's outer surface metallization is typically of pure gold or pure gold plating, the connection between the pure gold and the titanium is typically done with a gold-filled conductive polyimide. In a similar manner, the connection between the lead wire 124, which may be comprised of platinum iridium, and the capacitor's inside diameter 112 which is typically comprised of gold, is preferably a gold-filled conductive polyimide. Alternative materials, such as gold brazing compound or the like, which forms a non-migratable material, may also be used. Such gold brazed material is pure gold, pure platinum, or equivalent such that it is noble and therefore does not migrate. A special platinum or gold bearing fired on glass frit may also be used. See Table 1 above.

With respect to the conductive connections, a conductive polyimide is preferable to a conductive epoxy because of its generally higher temperature rating, although either may be used. An alternative to the use of a conductive thermal-setting adhesive would be the use of a non-migratable weld, braze or solder compound, such as pure gold braze or weld.

With particular reference to FIG. 27, an insulator 130 is disposed between the ferrule 122 and the lead wire 124. The interface between the insulator 130 and the terminal pin 124 and ferrule 122 must be hermetically sealed. Such seal 132 is comprised of a suitable biocompatible material such as pure gold braze or TiCuSil or CuSil. It should be noted that TiCuSil and CuSil are brazing alloys that bind up the silver so tightly that it cannot readily migrate and form a dendrite.

Thus, the capacitor 110 and assembly illustrated in FIGS. 21-27 is comprised of materials that have been constructed of suitable biocompatible and non-migratable materials, such as noble metals, such that even in the presence of body fluid and bias voltage would not migrate and form a dendrite. That is, the capacitor inside and outside termination surfaces 112 and 114, the active and ground electrodes 116 and 118, the lead wire 124, and connective materials 126, 128 and 132 are all non-toxic and non-migratable material, at least where exposed to the body fluid. Thus, dendritic growth is prevented.

Figure 28:
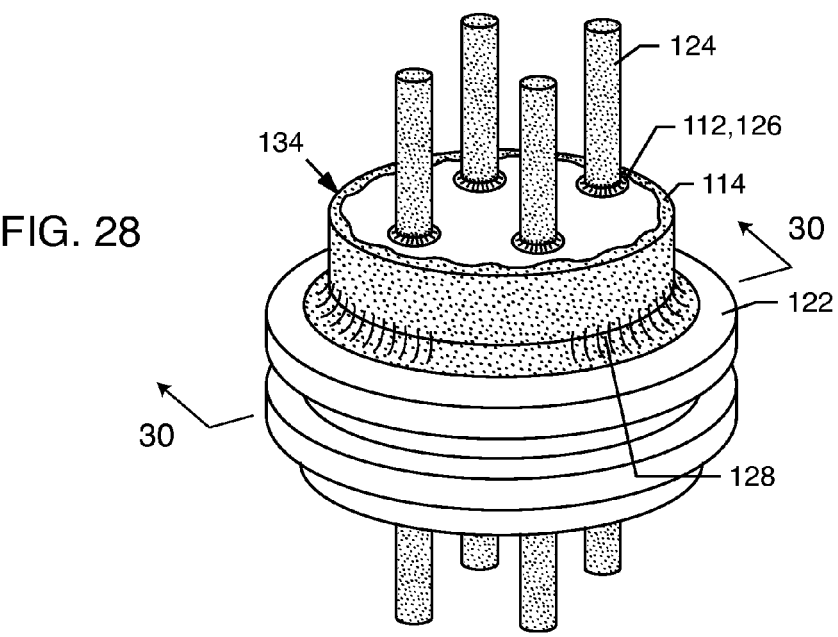
FIG. 28 is an isometric view of a quadpolar surface mounted capacitor in accordance with the present invention.
Figure 29:
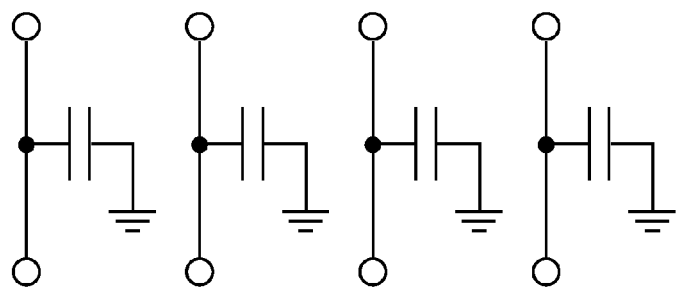
FIG. 29 is an electrical schematic diagram of the capacitors of FIG. 28.
Figure 30:
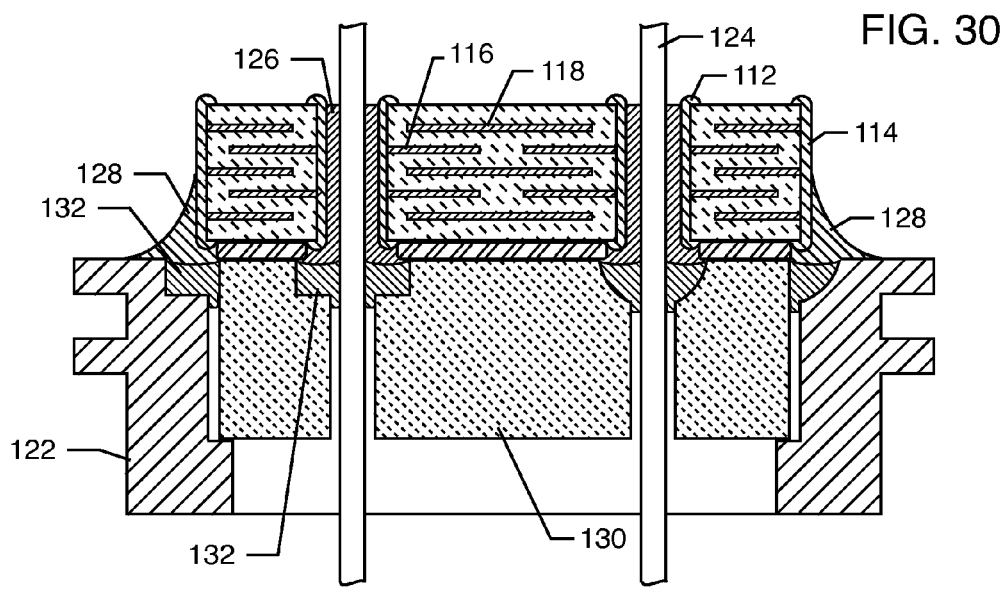
FIG. 30 is a cross-sectional view taken generally along line 30-30 of FIG. 28, illustrating internal components thereof and the use of non-migratable materials.

With reference now to FIGS. 28-30, the present invention is not limited in the type or configuration of capacitor used. A quadpolar surface mounted feedthrough capacitor 134 is illustrated which is entirely constructed of non-migratable materials, at least where exposed to body fluids and moisture. Thus, all of the materials exposed to the body fluid side are made of materials that will not form dendrites or migrate. That is, the portion of the lead wire 124, inner surface metallization 112, connective material 126, outer termination surface 114, and connective material 128 to the ferrule 122 which are exposed to the body fluid are comprised of biocompatible and non-migratable materials as described above. Preferably, the electrodes 116 and 118 as well as the seals 132 of the insulator 130 are also comprised of such biocompatible and non-migratable materials as described above. It will be appreciated that in this and the following descriptions of various embodiments, functionally equivalent components are often referred to with the same reference number used in connection with the description of other embodiments.

As mentioned above, the lead wires 124 and inner and outer metallization 112 and 114 of the capacitor can be plated, such as depositing electroplated nickel first then overplating with pure gold or the like plating, or otherwise coated with the non-migratable material. Alternatively, they are comprised of such materials.

Figure 31:
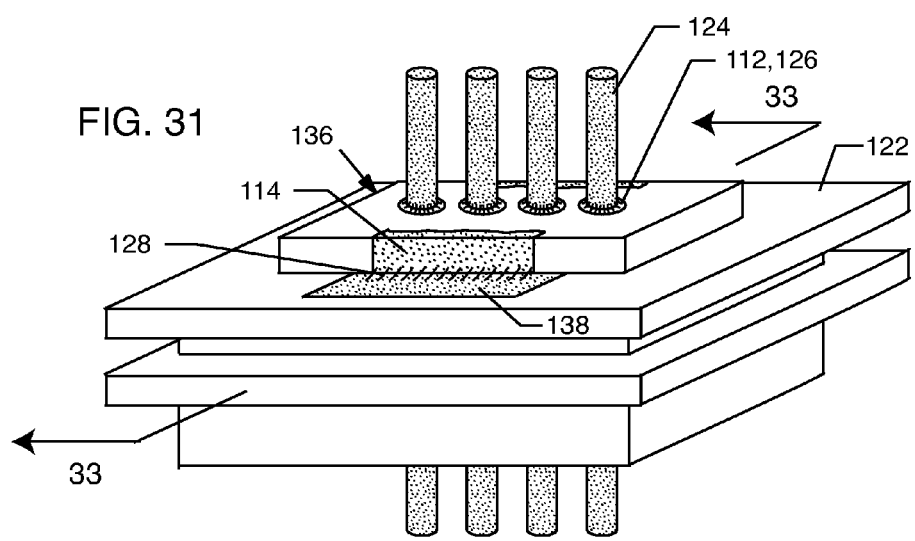
FIG. 31 is an isometric view of an inline quadpolar capacitor assembly embodying the present invention and incorporating non-migratable materials.
Figure 32:
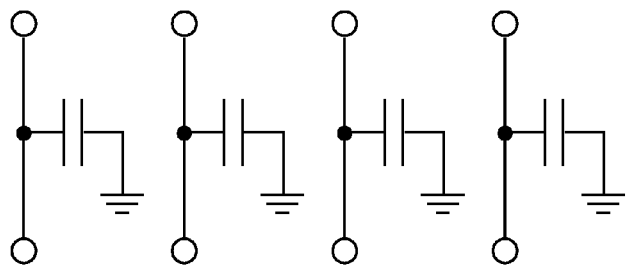
FIG. 32 is an electrical schematic diagram of the capacitor assembly of FIG. 31.
Figure 33:
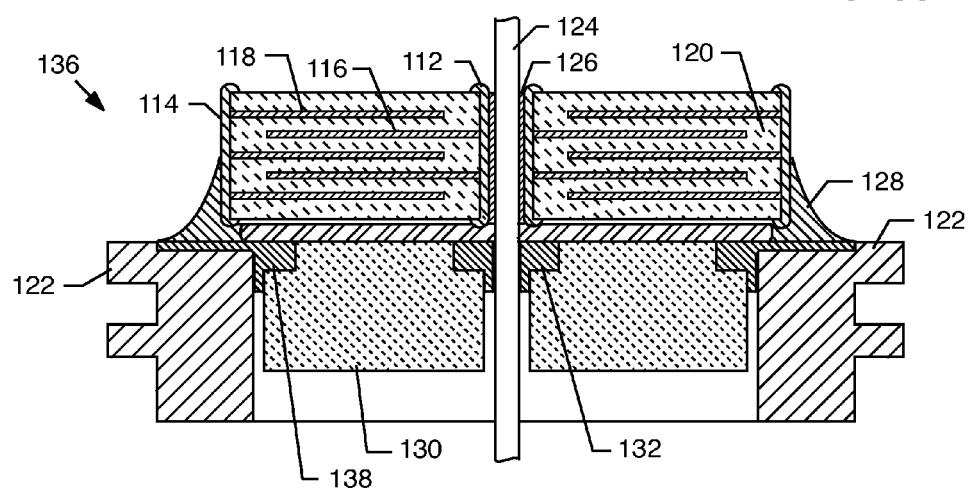
FIG. 33 is a cross-sectional view taken generally along line 33-33 of FIG. 31, illustrating internal components thereof.

With reference now to FIGS. 31-33, an in-line quadpolar capacitor 136 is shown surface mounted on the body fluid side of the hermetic terminal 122 of a human implantable medical device. The lead wires or terminal pins 124 are coated with or formed of a non-migratable material, such as a noble metal including gold or platinum. Similarly, as described above, the connection 126 between the inner termination surface 112 and the lead 124 is a non-migratable material, such as those described in Table 1 above. In this embodiment, a hermetic terminal with gold bond pads 138 is used. A biocompatible and non-migratable conductive connector 128, such as gold or platinum filled thermal-setting conductive polyimide or pure gold braze or the like, is used to connect the outer termination surface 114 to the gold bond pad 138. Thus, on the body fluid side, those portions of conductive components which are exposed to the body fluid are comprised entirely of biocompatible and non-migratable materials to prevent the formation of dendrites.

Figure 34:
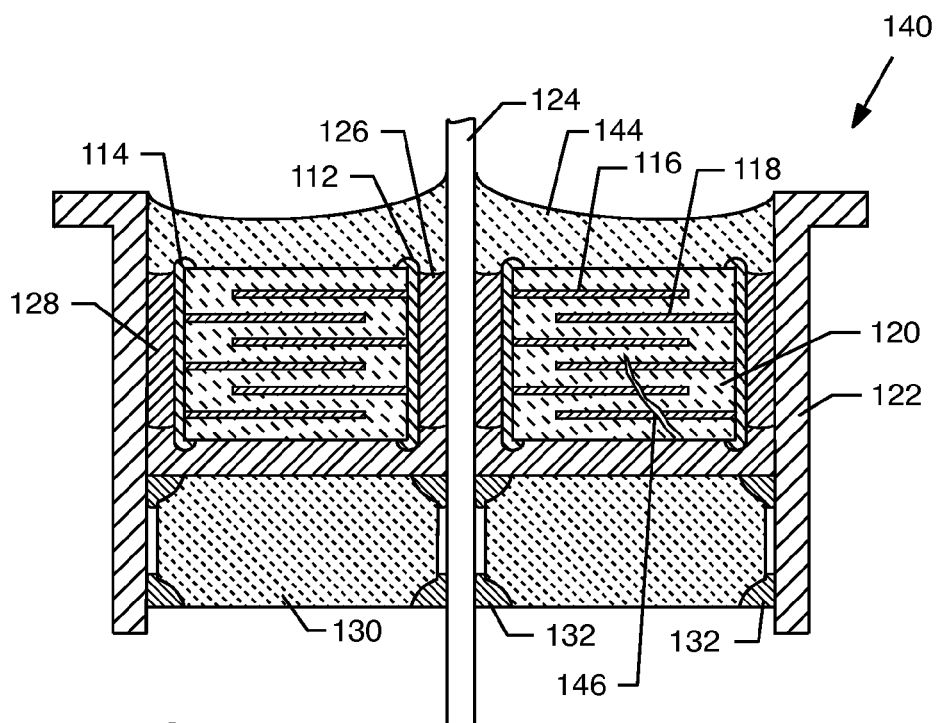
FIG. 34 is a cross-sectional view similar to FIG. 1, but illustrating use of non-migratable materials in accordance with the present invention and thus having a crack between electrodes thereof without dendritic growth.
Figure 35:
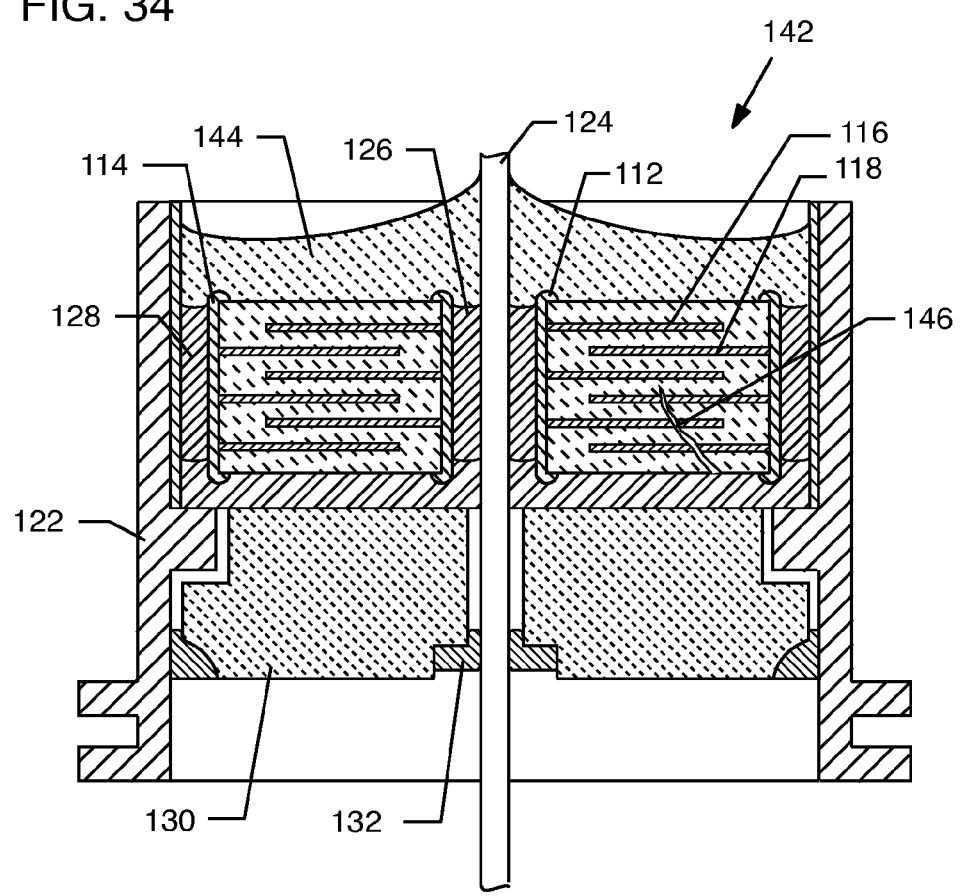
FIG. 35 is a cross-sectional view of another feedthrough capacitor having a crack therein and without dendritic growth due to the use of non-migratable materials in accordance with the present invention.

With reference to FIGS. 34 and 35, hermetic terminal assemblies 140 and 142 are illustrated comprised of the biocompatible and non-migratable materials as discussed above, and having a sealant 144, such as the epoxy sealant disclosed in U.S. Pat. No. 6,055,455, the contents of which are incorporated by reference herein. In these cases, the capacitors are deliberately shown with fractures or cracks 146, resulting during the manufacturing process as described above. However, it will be noted that these cracks have no metal migration or dendrite within them. This is due to the fact that the capacitors are entirely constructed of materials that do not migrate. This includes the lead wire terminal pin 124, inner and outer termination surfaces 112 and 114, electrodes 116 and 118, and connective materials 126 and 128. Thus, even a fairly large crack in a capacitor does not present a long-term reliability problem, particularly for a low-voltage device. This is due to the fact that no harmful metal migration in the form of dendrites will form.

Accordingly, in both hermetic terminals 140 and 142, the penetration through the non-conductive sealing epoxy 144, shown on the top of the capacitor, is not a problem. Even though it is expected that over a long period of time body fluid would penetrate through the covering epoxy 144 through bulk permeability or through micro-separations due to lack of adhesions, the capacitor and its interconnections have been all constructed in accordance with the present invention so as not to be comprised of migratable materials, thus preventing the formation of insulation resistance reducing dendrites.

FIGS. 36-42 show an internally grounded bipolar capacitor 148 embodying the present invention. The capacitor 148 is designed to be surface mounted to a hermetic terminal 122, such as the illustrated ferrule. Capacitor 148 has been specially prepared during manufacturing to lay down a very thin layer of glass 150 on at least its top surface, and preferably both its top and bottom surfaces, as illustrated. It has been found that such glass layers 150 not only render the overall capacitor 148 stronger so it will better resist both mechanical and thermal stress during handling, installation and assembly of the implantable medical device, but also optimizes the capacitor's 148 resistance to moisture or penetration by fluids. Thus, unlike the aforementioned epoxy sealants, the use of a glass sealant may provide sufficient resistance to penetration by fluids so as to enable a capacitor of migratable materials to be placed on the body fluid side. However, in a preferred embodiment, the conductive components which might be exposed to the body fluid are comprised of biocompatible and non-migratable materials to ensure that the harmful metal migration and dendrite formation discussed above will not occur.

Applying the glass layer 150 can be done in various manners. For example, after capacitor firing, the capacitor can be run through a glass-sealing kiln very near the melting point of the glass, but just below it. The capacitor 148 would be placed on glass sheets which would be run through the furnace allowing some of the glass to diffuse into the surfaces of the ceramic capacitor 148. The glass has the effect of reducing some of the capacitor porosity and filling it with insulating glass. This cuts down on any tendency to form a dendrite and also makes the capacitor itself more moisture resistant. Another technique of applying the glass layer 150 would be the use of a fine glass or ground powdered glass, or a paste-like frit which would be applied to the capacitor which is then run through a firing furnace. High volume applications could be by silk-screening or spray processes. After the manufacturing of the ceramic capacitor 148 at very high temperature, it would be possible to lay down a very thin glass layer, which would be fired or co-fired into place.

The capacitor 148 of FIG. 36 is designed to be mounted to a hermetic terminal, such as the ferrule 122 illustrated in FIG. 37. This ferrule has been simplified into a rectangular shape, although in actual practice it can have many flanges and take on many shapes and configurations depending upon its application. The two outer most leads 124 are formed in insulative relationship with conductive ferrule 122 by use of insulating connectors or sealants 152. The center lead wire, or ground wire 154 is grounded and directly brazed or welded to the conductive ferrule 122 using non-migratable material 128, such a gold braze or the like. The grounded pin or wire 154, which is brazed or welded to the ferrule 122 with a non-migratable material 128 is the connection point for the capacitor's internal ground electrode plates 118.

FIGS. 39 and 40 illustrate the active and ground electrode plates used in such a configuration, such as that described in U.S. Pat. No. 5,905,627.

Figure 41:
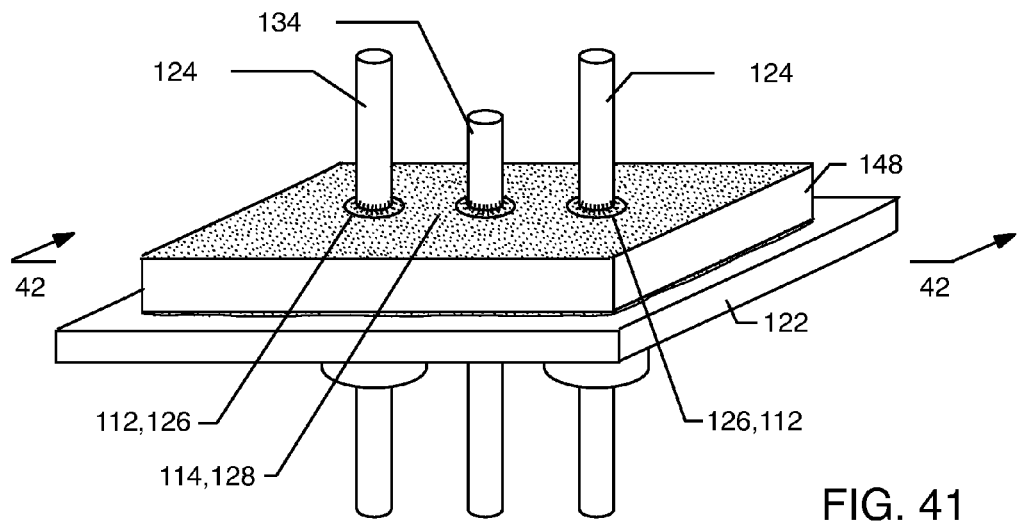
FIG. 41 is a perspective view of the capacitor of FIG. 36 attached to the hermetic terminal of FIG. 37.
Figure 42:
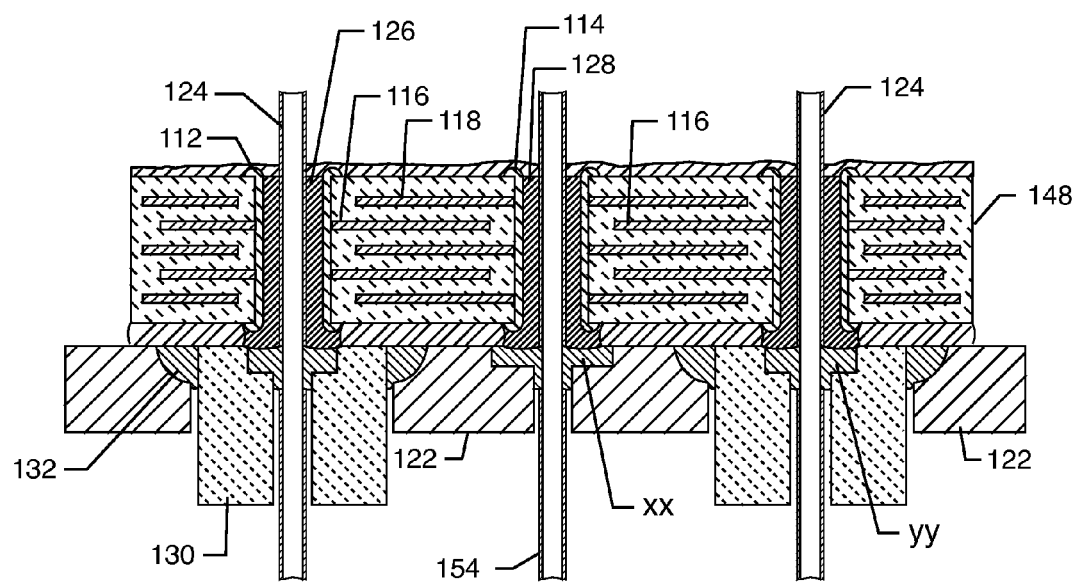
FIG. 42 is a cross-sectional view taken generally along line 42-42 of FIG. 41, illustrating internal components of the assembly, and a glass layer thereon.

With reference now to FIGS. 41 and 42, as discussed above, the capacitor 148 and assembly are manufactured in accordance with the teachings of the present invention. That is, the internal electrode plates 116 and 118 are comprised of platinum or alloys of gold, platinum or palladium. Other electrode compositions that would not migrate in the presence of body fluids are also acceptable. Moreover, the conductive connections 126 and 128 are comprised of non-migratable thermosetting or brazing material such as that described above. The hermetic seal mechanical connections 132 are preferably comprised of a gold braze of the like. An alternative to this would be to use a glass seal where a compression or a fusion seal is formed between the ferrule and the outer lead wires 124 such that no metal joining is required at all.

One advantage of the internally grounded capacitor 148 is that it does not require any perimeter or outer termination metallization at all. Neither does it require any electrical or mechanical connection between the capacitor 148 and the metallic ferrule 122 as this connection occurs between the ground terminal pin 154 and the ferrule 122. As there is no capacitor outer metallization, the connectors 128 between the ground lead wire 154 and the ferrule 122 are comprised of non-migratable materials, as are the seals and connectors 132 between the insulators 130 and the ferrule 122. Of course, the connective material 126 between in the inner diameter termination surfaces 112 and the lead wires 124 are comprised of non-migratable materials as well.

Figure 43:
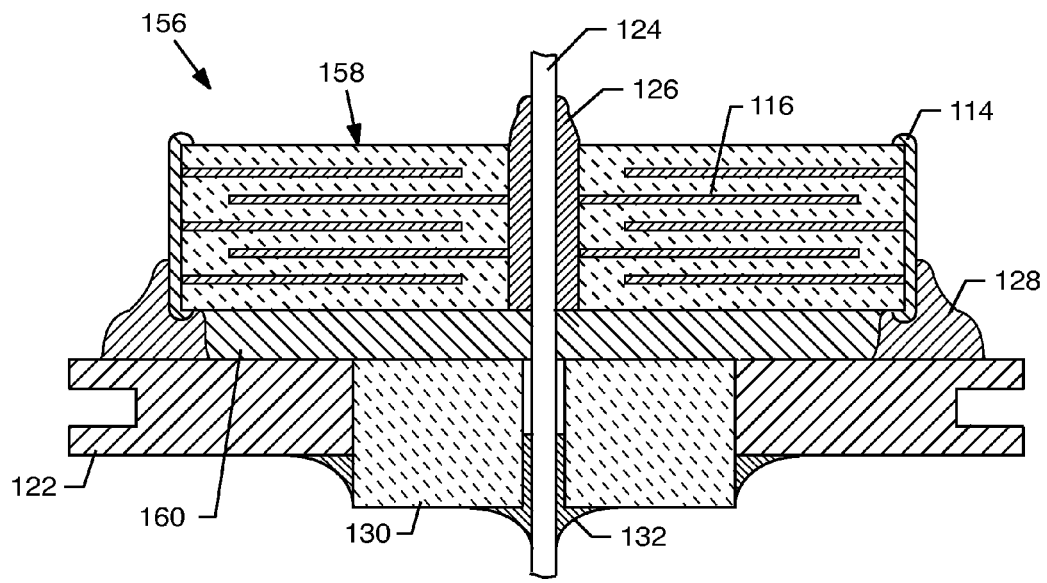
FIG. 43 is a cross-sectional view of a feedthrough capacitor assembly, wherein the inner metallization of the capacitor has been removed in accordance with the present invention.

With reference now to FIG. 43, prior art monolithic ceramic capacitors have been constructed with termination materials. Such termination materials cover both rectangular MLC chip capacitors and feedthrough chip capacitor through-hole passageways. The reasons for such termination metallization materials are: (1) to provide electrical connection to the active and ground electrode plates, which are set in parallel; and (2) to provide a surface wherein one can solder or otherwise make conductive attachments from the capacitor to other components in the circuitry. In the specific case of a human implant device as illustrated and described above, termination metallization materials are utilized in the connection from the capacitor active electrode plates and terminal pin or lead wire, and the connection between the capacitor ground electrode plates and the metallic ferrule.

The assembly 156 illustrated in FIG. 43 is similar to that illustrated in FIGS. 25-27, except that the feedthrough capacitor 158 does not include an inner termination metallization surface, shown by the reference number 112 in FIGS. 25-27. Instead, the lead wire or terminal pin 124 is conductively coupled to the set of active electrodes 116 of the capacitor 158 solely with the electrical connective material 126. The connective material 126 is biocompatible and non-migratable and can be comprised of such materials as gold or platinum-filled thermal-setting conductive polyimide or any other conductive material that has been loaded with suitable particles such as gold or platinum such that it can make a direct electrical contact with the one or more electrodes 116.

It is important that the conductive thermal-setting material 126 penetrate all the way down through the one or more passageways of the feedthrough capacitor 158. This is best accomplished by injection or centrifuging. Accordingly, it is important that this material 126 not be allowed to extend underneath the capacitor 158 such that it could cause a short between the ferrule 122 or the outer metallization 114, which is still present in the embodiment illustrated in FIG. 43. Accordingly, an insulating material or insulating washer 160 is disposed below the capacitor 158 to prevent material 126 from migrating or penetrating into areas where it would be undesirable. In a preferred embodiment, the insulating material 160 is an adhesively coated polyimide washer.

Of course, as discussed above, the one or more electrodes 116 would also be of non-migratable material such as a noble metal including platinum or gold or an alternative alloy consisting of gold platinum and palladium. The thermal-setting conductive material 128 used to electrically connect the conductive ferrule 122 with the outer metallization 114 of the capacitor 158 is comprised of non-migratable materials as described above.

Whereas the present invention is primarily directed to human implanted devices and applications, the embodiment illustrated in FIG. 43 have much broader application for all feedthrough capacitors whether they be for medical implant or not. The concept of making electrical connection from a lead wire or to the outside diameter without the need for termination material has obvious advantages to those skilled in the art. It is very labor-intensive to apply these termination materials, which involve several process and termination firing steps. Eliminating the inner termination surface 112 and electrically coupling the lead wire 124 directly to the active electrode plates 116 with material 126 eliminates a number of process steps relating to prior art capacitor inside diameter termination material.

Figure 44:
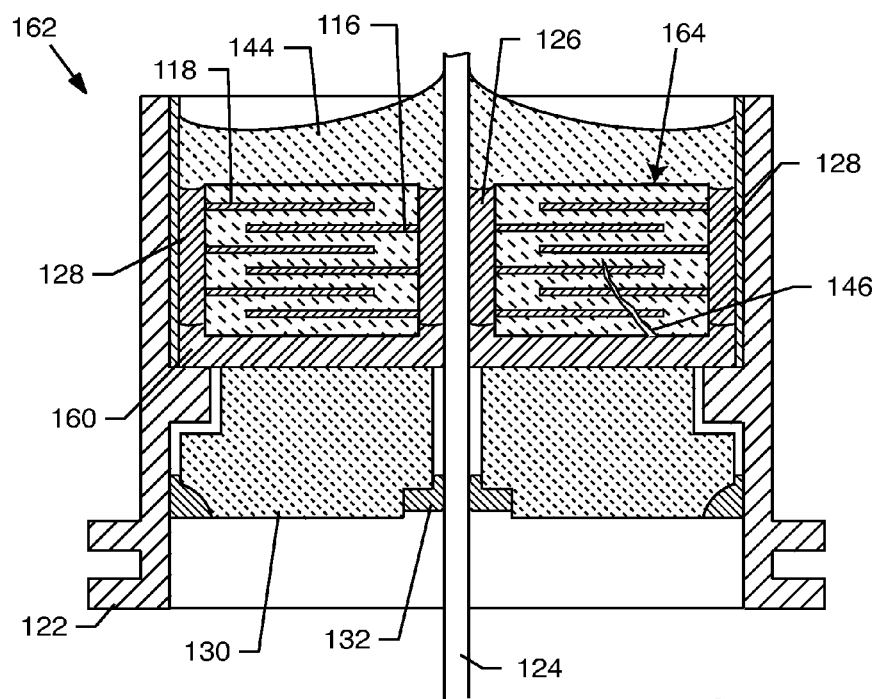
FIG. 44 is a cross-sectional view of another feedthrough filter assembly, wherein the inner and outer metallization of the capacitor has been eliminated in accordance with the present invention.

FIG. 44 illustrates a terminal assembly 162 which is similar to that illustrated in FIG. 35. However, the feedthrough capacitor 164 embedded within the surrounding metallic ferrule 122 does not include inside diameter or outside diameter metallization (labeled with reference numbers 112 and 114 in FIG. 35). Instead, the one or more feedthrough holes, which may be of any geometry, are filled with the conductive material 126 described above in relation to FIG. 43. Conductive material 128, which may comprise the same material as 126, directly conductively couples the ground electrode plates 118 to the hermetic terminal ferrule 122. Once again, insulative material, typically in the form of a washer 160, prevents shorting of the capacitor.

Figure 45:
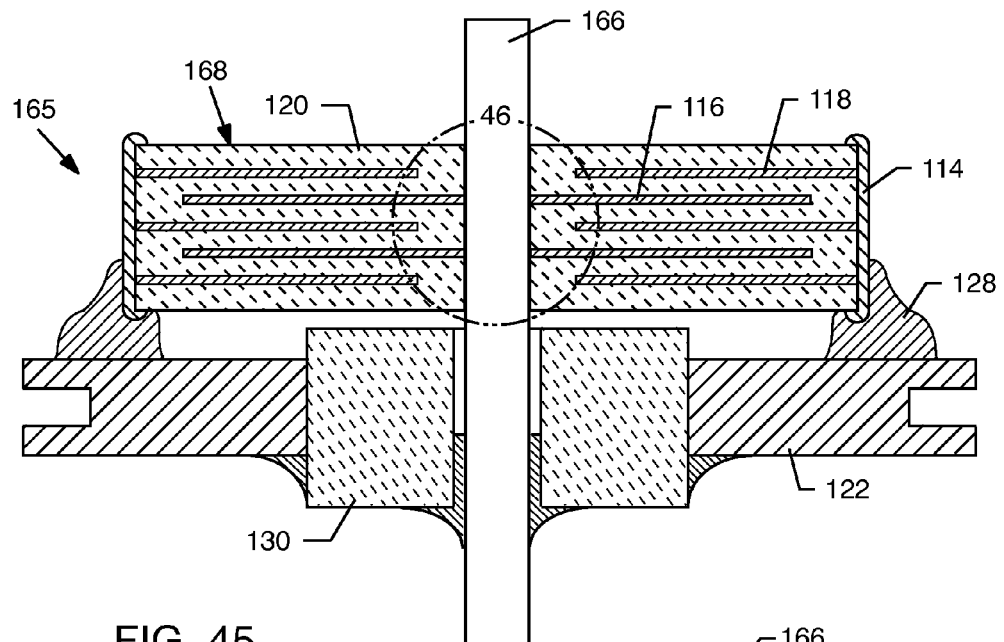
FIG. 45 is a cross-sectional view of a feedthrough filter capacitor assembly, wherein a terminal pin directly contacts the active electrode portions of the capacitor in accordance with the present invention.
Figure 46:
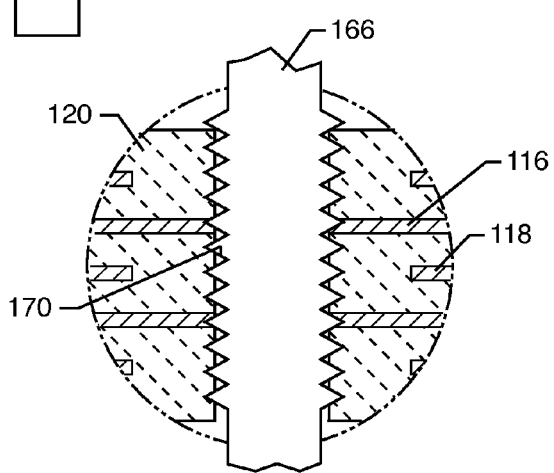
FIG. 46 is an enlarged sectional view taken generally from area "46" of FIG. 45, illustrating a knurled or roughened portion of the terminal pin.

With reference now to FIG. 45, yet another assembly 165 is illustrated which shows an alternative method of electrically coupling a terminal pin or electrical lead 166 to the internal electrode set 116 of the capacitor 168. In this case, the pin or wire 166 is designed to form a very tight or pressed fit within the inside diameter or passageway of the capacitor 168. In the instance of an inner metallization material 112, a mechanical connection is made between the lead wire 166 and the capacitor metallization 112. As illustrated in FIG. 45, the inner metallization 112 may be absent such that the active electrode plates 116 directly contact the terminal pin or electrical lead wire 166 either through the enlargement of the terminal pin 166 or the reduction in diameter of the passageway through the capacitor 168. In a preferred embodiment, the electrical lead 166 has been prepared prior to inserting with a knurled, sputtered or roughened area 170 which coincides with the internal electrode set 116 to increase the electrical contact surface area to either the capacitor metallization 112 or directly to electrodes 116. See FIG. 46.

It will be appreciated that the embodiments illustrated in FIGS. 43-46 incorporate the non-migratable materials previously discussed so as to have application in implantable biomedical devices in which the electronic network components of the EMI filter assembly, including the capacitor, are exposed to body fluid. The selection and use of the non-migratable materials and the construction of the capacitor, terminal pin or lead wire, and conductive connections provide a biocompatible surface which prevents dendritic growth and the like.

Figure 47:
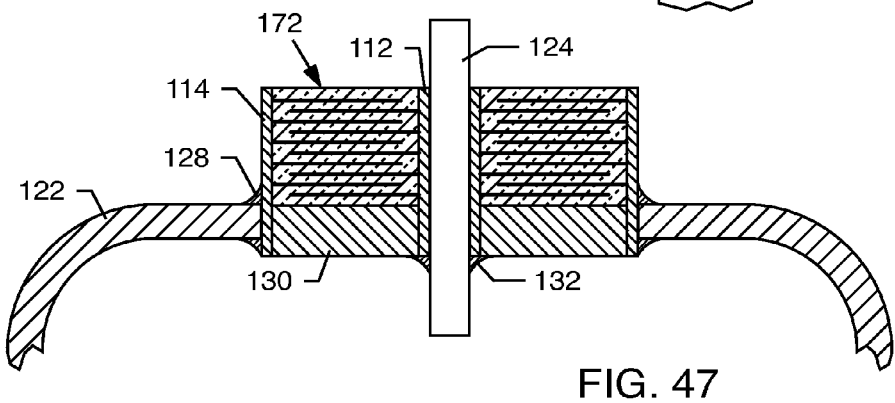
FIG. 47 is a cross-sectional view of an integrated feedthrough capacitor assembly embodying the present invention.

FIG. 47 illustrates an integrated feedthrough capacitor 172 such as that shown in U.S. Pat. No. 6,008,980, the contents of which are incorporated herein. In this case, the feedthrough capacitor 172 itself becomes its own hermetic seal. This is desirable as it eliminates a number of components and process steps. Incorporating the use of biocompatible and non-migratable materials in accordance with the present invention allows the capacitor 172 to be placed on the body fluid side of the hermetic seal.

In the previously illustrated and described embodiments, the capacitors have been feedthrough capacitors. However, it will be appreciated by those skilled in the art that the present invention is not limited to such feedthrough capacitors.

Figure 48:
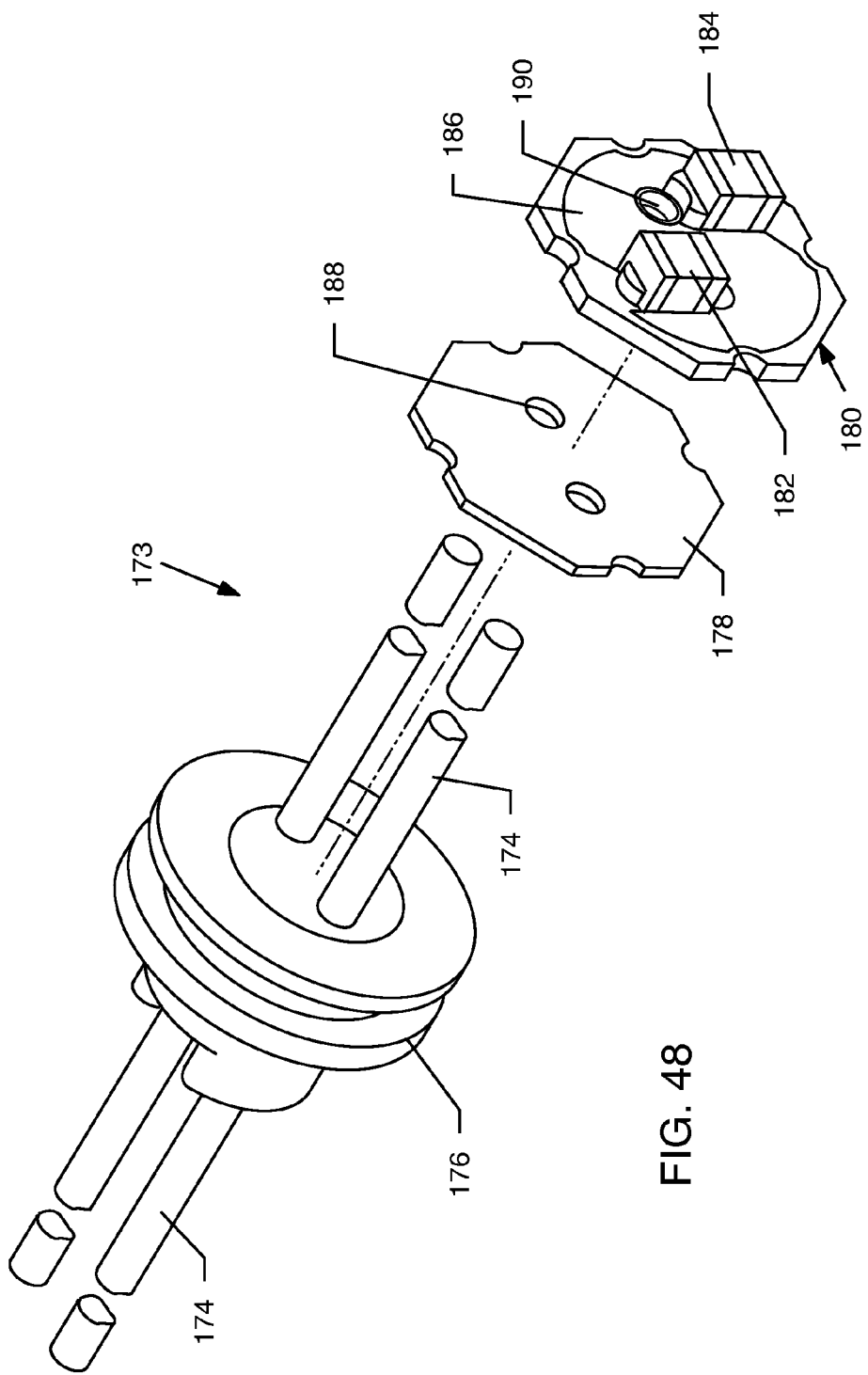
FIG. 48 is a partially fragmented exploded perspective view of a multi-lead feedthrough showing an insulating sheet between the feedthrough and filter support assembly and incorporating chip capacitors in accordance with the present invention.

In FIG. 48, an EMI filter assembly 173 is shown which is similar to that illustrated and described in U.S. Pat. No. 5,896,267, the contents of which are incorporated by reference herein. The assembly 173 includes multiple leads 174 extending through feedthrough 176 and insulating film 178. A capacitor support assembly 180 supports two chip capacitors 182 and 184. Insulating film 178 is disposed between the multi-lead feedthrough 176 in the capacitor support assembly 180. Of course, the arrangement is applicable to feedthrough assemblies of any number of leads. Insulating film 178 is shaped to contour match that of the substrate 186. The leads 174 extend through aligned apertures 188 and 190 of the insulating film 178 and substrate 186. As such, the leads 174 do not extend through the chip capacitors 182 and 184, but the chip capacitors 182 and 184 are designed so as to present active and ground electrode surfaces which interact with the leads 174 and a grounding terminal, as described in U.S. Pat. No. 5,896,267. The capacitors 182 and 184 and the pertinent conductive connection materials, leads 174, etc., are coated or comprised of non-migratable materials as discussed above so as to be placed on the body fluid side of the applicable implantable device outside of the hermetic terminal.

Thus, it will be appreciated by those skilled in the art that manufacturing feedthrough filter capacitor assemblies in accordance with the teachings of the present invention, namely, the use of a biocompatible and non-migratable material such as noble metals and the like, and/or glass sealing layers, allows the capacitor to be disposed outside of the housing of the medical device without tissue toxicity and the formation of harmful dendrites due to metal migration. The free space within the housing can enable the housing to be smaller, incorporate a larger battery, and have more sophisticated electronics. Other benefits will be appreciated by those skilled in the art.

All of the capacitor elements described above are shown attached on the body fluid side of hermetic seals that are generally associated with active implantable medical devices such as cardiac pacemakers, implantable cardioverter defibrillators and the like. However, there is an emerging need for passive circuit elements that are directly exposed to body fluids at locations along implanted leads and/or in implanted sensors which are remote from the active implantable medical device. In one particular application, during diagnostic procedures such as magnetic resonance imaging, it is important to prevent excessive currents from flowing in implanted leads such that the leads or their distal electrodes could overheat and damage body tissue. This is more thoroughly described in U.S. Pat. No. 7,363,090, the contents of which are incorporated herein by reference. In U.S. Pat. No. 7,363,090, novel bandstop filters consisting of a capacitor in parallel with an inductor are placed at or near the distal tip electrode in order to attenuate or prevent the flow of high frequency RF energy from an MR scanner. It has been well documented in the literature that induced RF energy from an MR scanner can cause severe damage to body tissues.

Accordingly, there is a need for biocompatible capacitor and inductor elements that do not have to be housed or enclosed within a hermetic seal.

Referring to U.S. Patent Publication No. 2007/0112398 A1, the contents of which are incorporated herein, one can see that there are a number of embodiments wherein the inductor and capacitor elements are enclosed in the hermetic seal. However, there are a number of negatives associated with the hermetic seal. One is, as a practical matter, the hermetic seal ends up being larger than the individual capacitor and filter components themselves. When threading leads in the human body, particularly into the left ventricular area, or tunneling leads, for example, to a deep brain stimulator, it is very important that the leads be as small as possible. One is referred to the medical French gauge shown in FIG. 66. When one is constrained to enclosing the capacitor and inductor elements in a hermetic seal, it is very difficult to get below six French (0.079 inches). However, for left ventricular and neurostimulator implants, it is desirable to get down to four or even three French (0.053 to 0.039 inches, respectively). Accordingly, it's not practical to enclose these components in a hermetic seal.

It is a feature of the present invention that the capacitor, inductor or resistor components and their internal and external electrical connections be manufactured entirely of biocompatible materials. This way they can be disposed within the lead systems without the need for a separate hermetic seal casing. Other applications include series inductors or resistors in lead wires which provide a variable reactive frequency element. Additional applications include remote sensors such as pulse oxygen sensors, hemodynamic or pressure sensors. These are typically placed at the end of leads inside the chambers of the heart, for example. There are also deep brain sensors that are used to detect the onset of an epileptic seizure. It is highly desirable that these deep brain electrodes be as small as possible so that when they are inserted, minimum damage is done to surrounding brain tissues. In addition, there is a need for biocompatible RFID sensor tags implanted within the human body (FIG. 95). RFID chips typically include a number of passive components including inductors, capacitors and the like.

Figure 49:
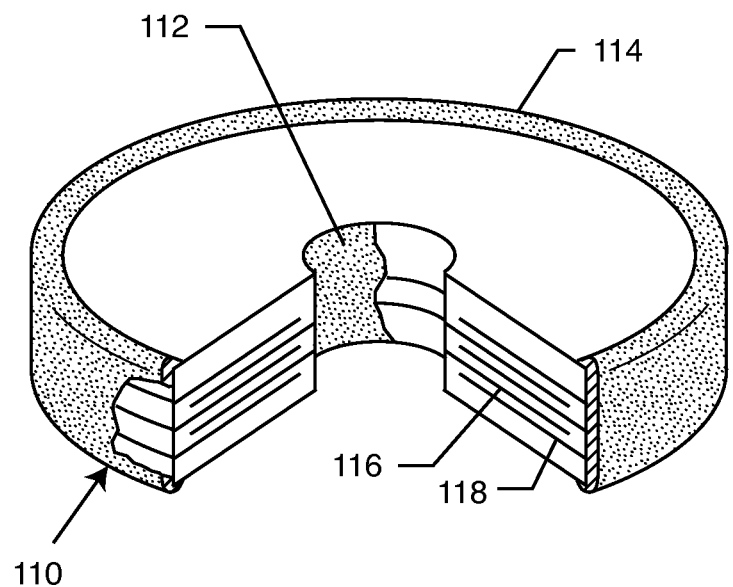
FIG. 49 is a partially fragmented perspective view of a unipolar discoidal feedthrough capacitor.

FIG. 49 illustrates a unipolar discoidal feedthrough capacitor 110 similar to that shown in FIGS. 21-24. This is a multilayer coaxial capacitor. One of its advantages is that it operates at very high frequency. This is because of its coaxial transmission line nature and the fact that it has very low internal inductance. The capacitor 110 includes overlapping circular electrode plate sets 116 and 118. Electrode plate set 116 is known as the active electrode plate set and is electrically connected to the capacitor inside diameter metallization 112 as shown. The ground electrode plate set 118 is attached to the outside diameter metallization 114. Similar feedthrough capacitors are often used in conjunction with EMI filters for active implantable medical devices. These are generally shown and described in U.S. Pat. Nos. 4,424,551; 5,905,627; 6,008,980; 6,643,903; 6,765,779 and many others.

Figure 50:
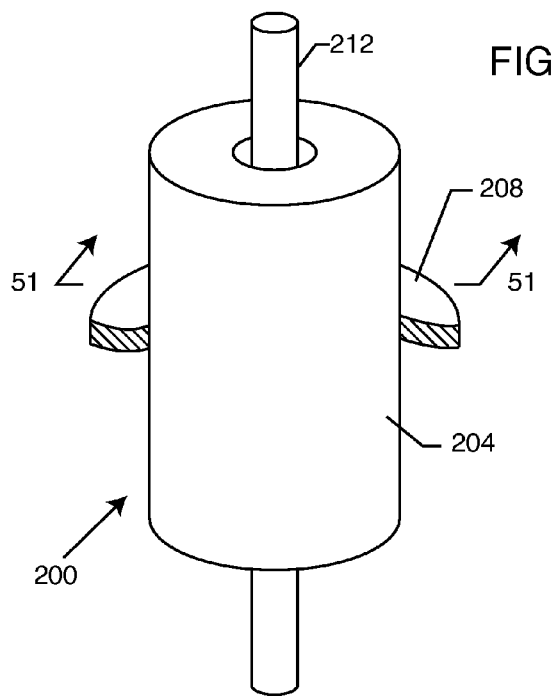
FIG. 50 is a perspective view of a tubular feedthrough capacitor.
Figure 51:
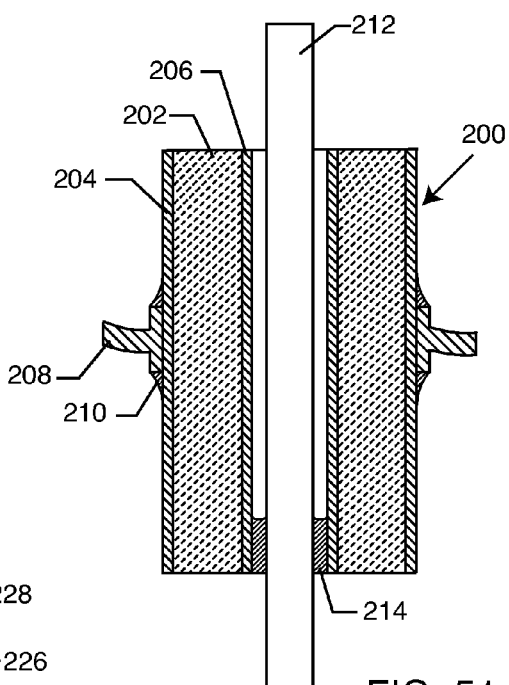
FIG. 51 is a sectional view taken along the line 51-51 of FIG. 50.

FIGS. 50 and 51 illustrate a tubular feedthrough capacitor 200. In the art, this is known as a single wall or extruded tubular capacitor, and is very commonly used in commercial electronic applications. Such capacitors 200 are fabricated in a drawing-extrusion process. The tubes are cut off at a desired length and are fired (sintered). The material in this case is a high K ceramic dielectric 202. The tube is then metalized on the outside 204 and also metalized on the inside diameter 206 as illustrated. The capacitance is formed between the inner and outer diameter metallizations 204, 206 (two concentric cylinders separated by the high K dielectric). A flange 208 is typically associated with the capacitor 200 by high temperature solder attachment 210 for convenient mounting into a bulkhead. There is also a lead wire 212 which passes continuously through the feedthrough capacitor 200 and is attached to the inside diameter metallization 206 using a high temperature solder 214. These prior art feedthrough capacitors are very efficient low inductance capacitors and are used in a wide variety of prior art electronic low pass EMI filter applications.

Figure 52:
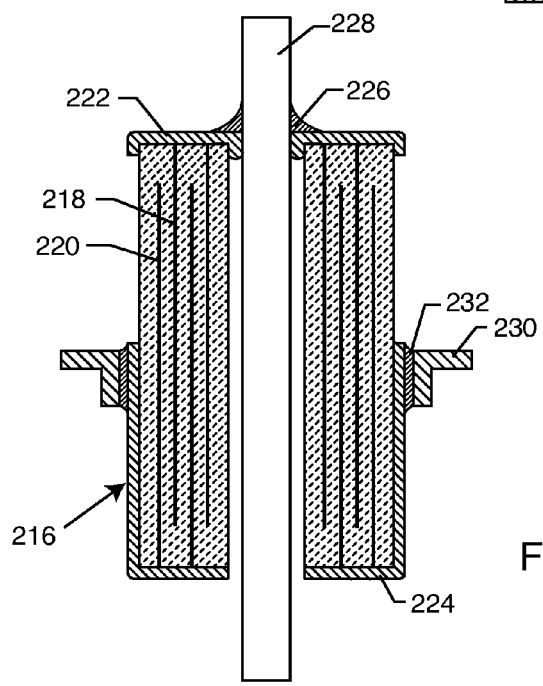
FIG. 52 is a sectional view similar to that shown in FIG. 51, illustrating a multilayer tubular capacitor.

FIG. 52 is a cross-section of a multilayer tubular capacitor 216. This is very similar to the capacitor 200 shown in FIG. 51 except that it is not formed by tube extrusion processes. This capacitor 216 is rolled, has embedded electrode plates 218, 220, and has a cylindrical shape. It is then fired and metallization is placed on its top end 222 and bottom end 224 as shown. An electrical connection 226 is made to lead wire 228. Metallization 224 is attached to the electrode set 220 at the bottom of the cross-section. An optional flange 230 is added for convenient mounting into a bulkhead. This flange is attached using high temperature biocompatible and non-migratable solder, braze, thermal-setting conductive adhesive or the like 232.

Figure 53:
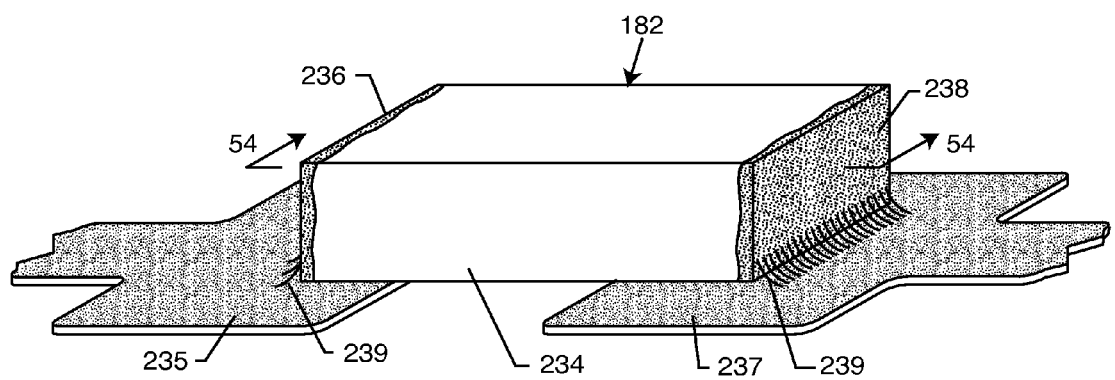
FIG. 53 is a perspective view of a rectangular monolithic ceramic capacitor (MLCC)

FIG. 53 is an isometric view of the rectangular monolithic ceramic capacitor (MLCC) 182 as shown in FIG. 48. It comprises a main ceramic body 234 and it has termination surfaces 236 and 238 for convenient mounting to a circuit board, lead wires or the like.

Figure 54:
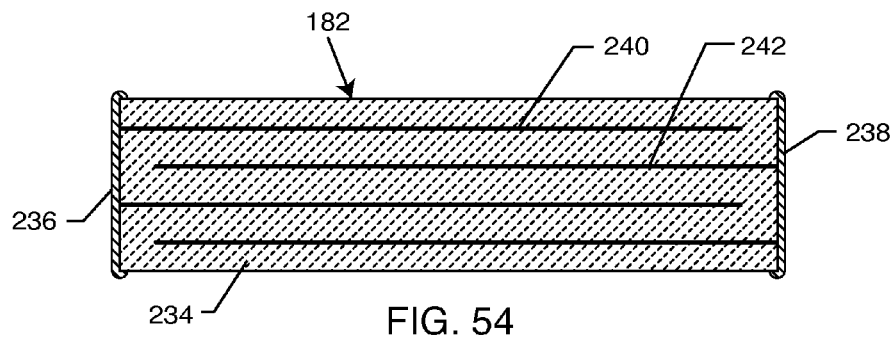
FIG. 54 is a sectional view taken generally along the line 54-54 of FIG. 53.

FIG. 54 is a cross-section of the capacitor 182 taken generally along line 54-54 in FIG. 53. One can see in the cross-section that there are two overlapping electrode plate sets 240 and 242. The overlapping of these electrode plate sets forms the active area of the capacitor 182. In a resistor application, one would deposit an electrode in a relatively thin trace or with relatively high resistivity materials. Accordingly, one can control a deliberately high value of resistance for certain applications.

Referring once again to FIG. 53, one can see that there are circuit traces 235, 237 which are typically part of a larger component network. Circuit traces 235, 237 would be deposited on a substrate such as alumina, polyimide or other similar biocompatible material. Circuit traces 235, 237 themselves, of course, must be of suitable biocompatible and non-migratable material in accordance with the present invention. Shown is an electrical connection material 239 which connects between termination surfaces 236 and 238 and circuit traces 235 and 237. Those skilled in the art will appreciate that circuit trace 237 is also functionally equivalent to a lead which could be also directly attached to the termination surface 238. The electrically conductive material 239 can comprise a conductive thermal-setting material comprising a polymer selected from the group consisting of: epoxies, polyimides, polyethylene oxide, polyurethane, silicone, polyesters, polycarbonate, polyethylene, polyvinyl chloride, polypropylene, methylacrylate, para-xylylene, and polypyrrhol. The circuit traces 235, 237, as mentioned, can be part of an electronic component network wherein the thermal setting material 239 has been filled with a non-migratable and biocompatible conductive material selected from the group consisting of titanium, platinum and platinum/iridium allows, tantalum, niobium, zirconium, hafnium, nitinol, Co—Cr—Ni alloys such as MP35N, HAVAR® and ELGILOY®, stainless steel, gold, ZrC, ZrN, TiN, NbO, TiC, TaC, gold-bearing glass frit, TiCuSiI, CuSiI, and gold-based braze. The electrical connection 239 can also be accomplished by a brazing, welding or soldering operation consisting of materials selected from the group consisting of: tantalum, platinum, and platinum/iridium allows, tantalum, niobium, zirconium, hafnium, nitinol, Co—Cr—Ni alloys such as MP35N, HAVAR® and ELGILOY®, stainless steel, gold, ZrC, ZrN, TiN, NbO, TiC, TaC, Indium Oxide/Indium Tin Oxide (Transparent Conductive Oxides), gold-bearing glass frit, TiCuSiI, CuSiI, and gold-based braze.

Figure 55:
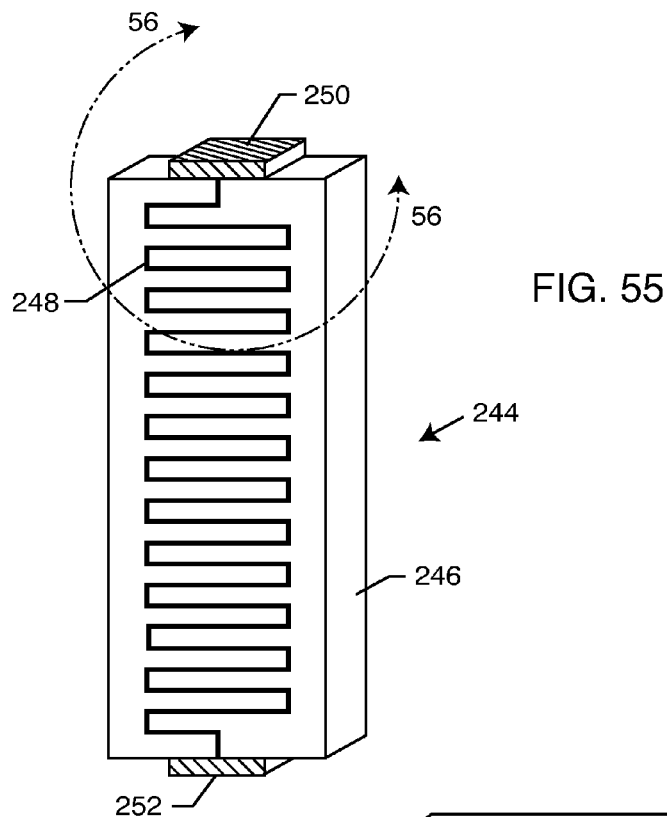
FIG. 55 is a perspective view of a novel non-ferrite chip inductor that may be utilized to build a bandstop filter.
Figure 56:
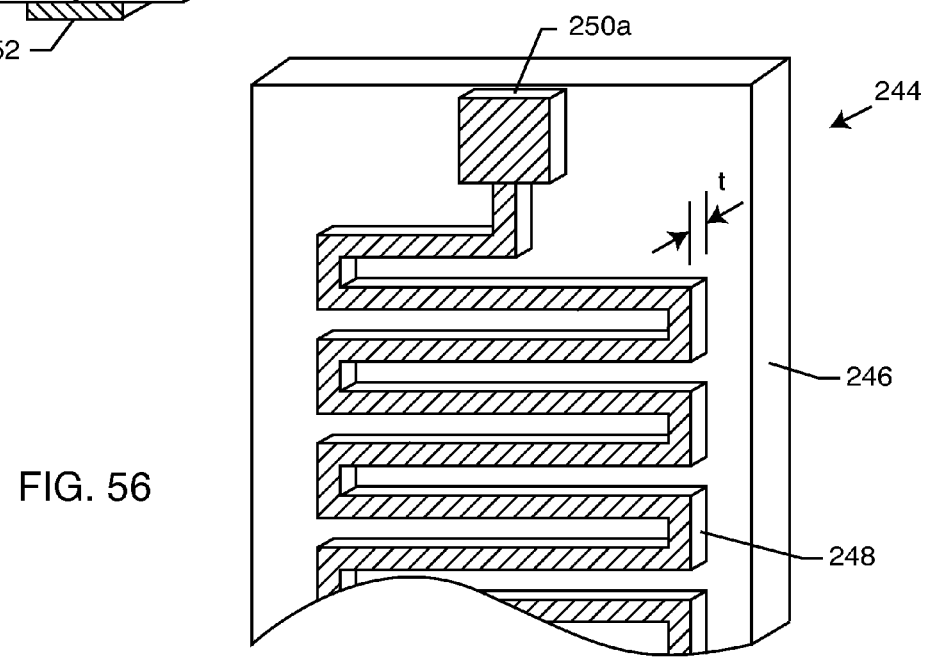
FIG. 56 is an enlarged fragmented view taken generally of the area designated by 56-56 in FIG. 55, and showing an alternative configuration.

FIG. 55 is an isometric drawing of a chip inductor 244 which could be used in place of a spiral wound inductor. The chip inductor 244 includes a thin substrate 246 which can be a biocompatible ceramic, circuit board material or the like. The inductor circuit trace 248 includes convenient wire bond pads 250 and 252. This is better understood by looking at the enlarged fragmented view of FIG. 56. There, an optional wire bond pad 250a is shown which has been surface mounted. This provides another way to attach a lead wire, for example, by gold wire bonding. Also, evident from FIG. 56 is the thickness t of the inductor circuit trace 248. In the inductor application, by depositing a relatively thick circuit trace 248, one can minimize the inductor ohmic losses (series resistance Rs). By minimizing Rs, there is less attenuation to the desired low frequency biologic signals. For example, in the case of a cardiac pacemaker, biological signals of interest are in the 10 Hz to 1000 Hz frequency range. At these frequencies, the inductive reactance is negligible (approaches zero). However, the series resistance $R_s$ of the inductor is still present and if too high could attenuate desired biologic signals. Additionally, the cardiac pacemaker output pulse could be attenuated by too much inductor resistive loss thereby presenting an inefficient use of AIMD energy and a potential problem for electrical capture (pacing) of the heart.

Chip inductors and chip resistors can also be wound on a cylindrical mandrel. For inductors, this mandrel could be of ferromagnetic materials in order to increase its volumetric efficiency and the amount of inductance it has achieved. However, ferromagnetic materials are contra-indicated for MRI imaging applications. Accordingly, it's preferred that the use of wound or coaxial resistors or inductors not employ any ferromagnetic materials. A major problem with winding multiple turns of small diameter wire is the relatively high value of DC resistance that would result. This is a highly desirable characteristic for a resistor, however, for an inductor, this high resistance would be undesirable at low frequency in that it could potentially attenuate pacing or stimulation pulses and also degrade sensing of biologic signals. An additional problem associated with inductors made from many turns of fine wire is that they can become their own heating element in the presence of magnetic resonance imaging (MRI). Accordingly, placing a lot of small diameter wire with a high series resistance in the implantable device lead wire system is generally not a good idea. The structure of FIGS. 55 and 56 overcomes such disadvantages by providing a volumetrically efficient inductor while at the same time minimizing the DC resistance.

Figure 57:
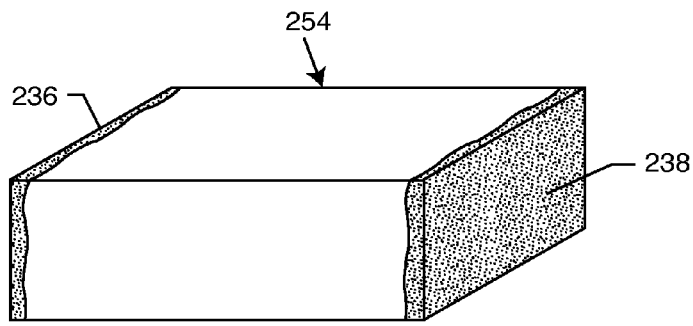
FIG. 57 is a perspective view of a novel composite monolithic ceramic capacitor-parallel resonant TANK (MLCC-T) which forms a bandstop filter.

FIG. 57 is an isometric view of a composite monolithic ceramic capacitor-parallel resonant TANK (MLCC-T) 254 which forms a bandstop filter 256. Viewed externally, one can see no difference between the MLCC-T 254 and an MLCC capacitor such as that illustrated in FIG. 53. However, the novel MLCC-T 254 has an embedded inductor 258 which is connected in parallel across the capacitor between its opposite termination surfaces 236 and 238.

Figure 58:
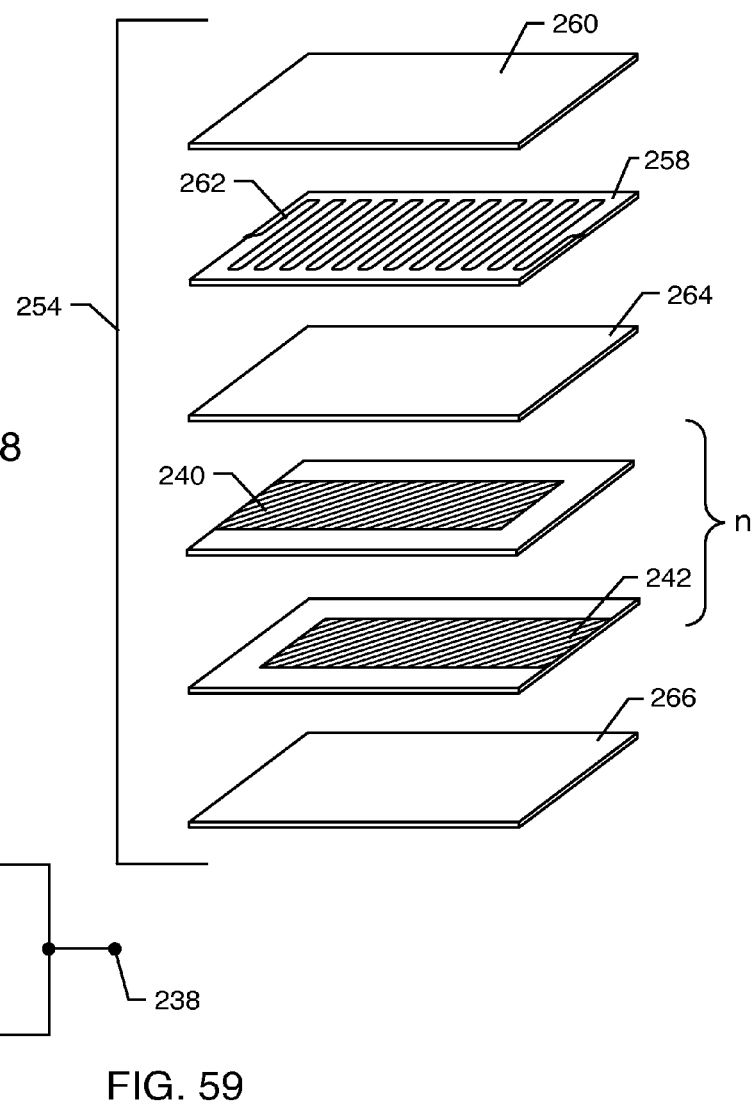
FIG. 58 is an exploded view of the various layers of the MLCC-T TANK filter of FIG. 57.

FIG. 58 is an exploded view of the various layers of the MLCC-T TANK filter 254 shown in FIG. 57. The MLCC TANK (MLCC-T) 254 includes an embedded inductor 258. At low frequencies, the embedded inductor 258 shorts out the capacitor from one end to the other. However, at high frequency, this forms a parallel TANK circuit 256 which is better understood by referring to the schematic diagram in FIG. 59. In FIG. 58, one can see that as the capacitor stacks up from the top, we have an area of blank cover sheets 260 followed by one or more embedded inductor layers 258. These inductor meander traces 262 can have a variety of shapes as further illustrated in FIG. 83 of U.S. Patent Publication No. 2007/0112398. Then there are a number of other blank interleafs 264 before one gets to the capacitor electrode plate sets, 240 and 242. As shown, the capacitor electrode plate set 240 connects to the left hand termination 236 and the capacitor electrode plate set 242 connects to the right hand termination 238. In FIG. 58, only single electrodes are shown as 240, 242. However, any number of plates "n" could be stacked up to form the capacitance value that is desired. Then bottom blank cover sheets 266 are added to provide insulative and mechanical strength to the overall bandstop filter MLCC-T 254. The meander inductor trace 262 is deposited or silk screened onto the layer 258, which can be one layer or many layers as desired. When many inductor layers 258 are put in parallel, this tends to reduce the overall inductance, but also desirably reduces the DC resistance of the inductor traces. The inductor 262 itself is known as a meander because it tends to meander back and forth as it goes through the MLCC-T 254.

In a typical monolithic ceramic capacitor manufacturing operation, the aforementioned stack up illustrated in FIG. 58, could be done both by wet-stack processing wherein each ceramic layer is sprayed down as a liquid or in a waterfall process, then pre-dried, and then the electrical layers (other capacitor electrodes or inductor traces) are laid down and dried. In a typical ceramic capacitor thick film process, these layers are laid down in ceramic tape and then stacked and pressed. In either case, a monolithic structure is formed which is then stacked and pressed. The methodology that is illustrated in FIGS. 57 and 58 is also applicable to a wide range of other types of capacitor technologies including electrolytic and film. For example, film capacitors can be stacked like an MLCC or rolled encompassing any of the embedded inductor traces as illustrated herein. It will also be appreciated that wound or monolithic layered film capacitors could also be constructed with an attached or embedded inductor in a similar fashion. Accordingly, the concepts of the present invention are applicable to a wide variety of equivalent electronic network component technologies.

At this point, there is a binder burn-out process which raises the green (unfired) capacitor from relatively low temperature to an elevated temperature. This process is to allow volatiles and solvents that were included in the ceramic slurry or tape to volatilize and slowly evolve and dissipate out of the monolithic structure. Eliminating these volatiles prior to high temperature firing or sintering is necessary so that the MLCC-T layers will not delaminate. The next step in this process is to fire or sinter the composite MLCC-T 254 at very high temperature. This causes the ceramic grains to sinter forming a hard monolithic structure. The last step, referring to FIG. 57, is the application of the biocompatible and non-mirgratible termination surfaces 236 and 238. These termination surfaces can be a biocompatible thick film ink, such as glass fritted platinum or gold, a gold plating, or the like and applied in many processes that are known in the art. Once again, the overall MLCC-T 254, which is illustrated in FIG. 57, looks identical to a prior art MLCC. However, embedded within it is the novel inductor structure 258 creating the novel parallel bandstop filter 256.

Figure 59:
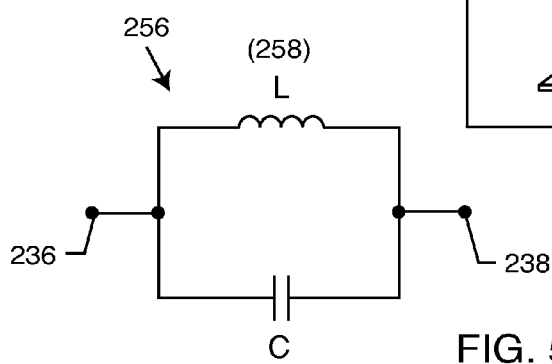
FIG. 59 is an electrical schematic diagram of the MLCC-T bandstop filter of FIGS. 57 and 58.

Referring to schematic drawing FIG. 59, one can see that the inductor L has been placed in parallel with the capacitor C which is all conveniently located within the monolithic structure MLCC-T 254 shown as FIG. 57.

Referring once again to FIG. 58, in a typical embodiment one might have one to five inductor layers 258 (or many more). By putting additional inductor layers 258 in parallel, one can drop the overall DC resistance $R_L$ which is desirable in an active implantable medical device application. The capacitor electrode plate sets 240 and 242 can vary anywhere from two to four plates all the way up to as many as hundreds of alternating parallel plates. The number of electrode plates and their overlap area, (along with the dielectric constant and dielectric thickness) determines the capacitance value for a particular resonant bandstop filter application. Preferably, the inductor traces 262 and the capacitor's electrode plates 240 and 242 would be of a noble metal such as pure platinum or gold which are biocompatible materials. Since these bandstop filters 256 will be placed in human tissues (for a pacemaker, literally floating in the blood stream), it is very important that all of the materials, including platinum, gold, palladium, tantalum, niobium and titanium, be biocompatible and extremely reliable. Platinum is an excellent choice for such biocompatible materials and is preferred in the MLCC-T 254 of the present invention because of its excellent compatibility with the ceramic layers such as Barium Titinate, Barium Strontinate, and the like. This is because of the high melting point of the platinum. In a preferred embodiment, the ceramic materials including Barium Titinate or Barium Strontinate and the like would be lead free and would themselves be composed of entirely biocompatible materials.

Figure 60:
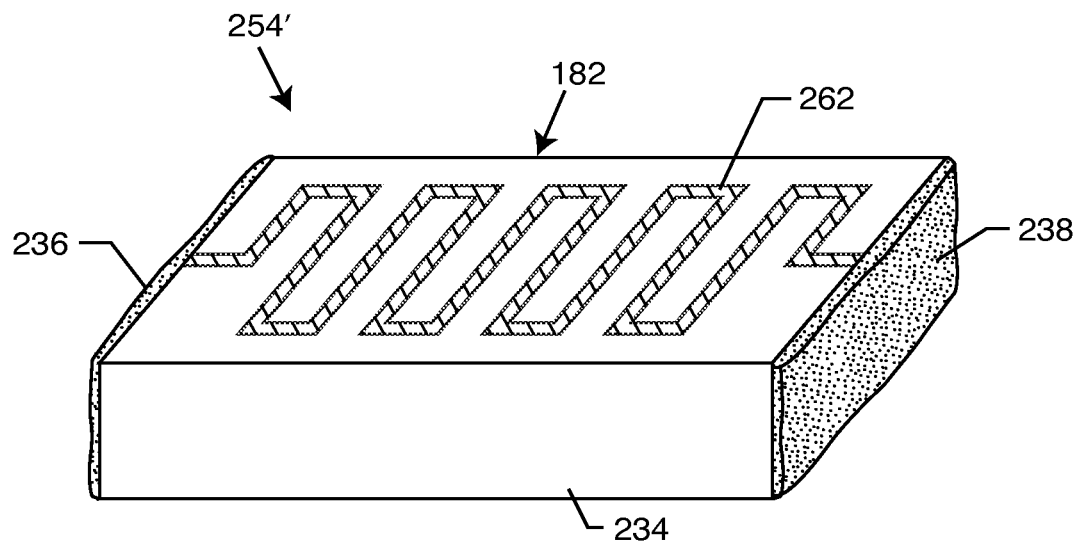
FIG. 60 is a perspective view of a monolithic chip capacitor showing an exemplary inductor circuit trace applied to an upper surface thereof.
Figure 83:
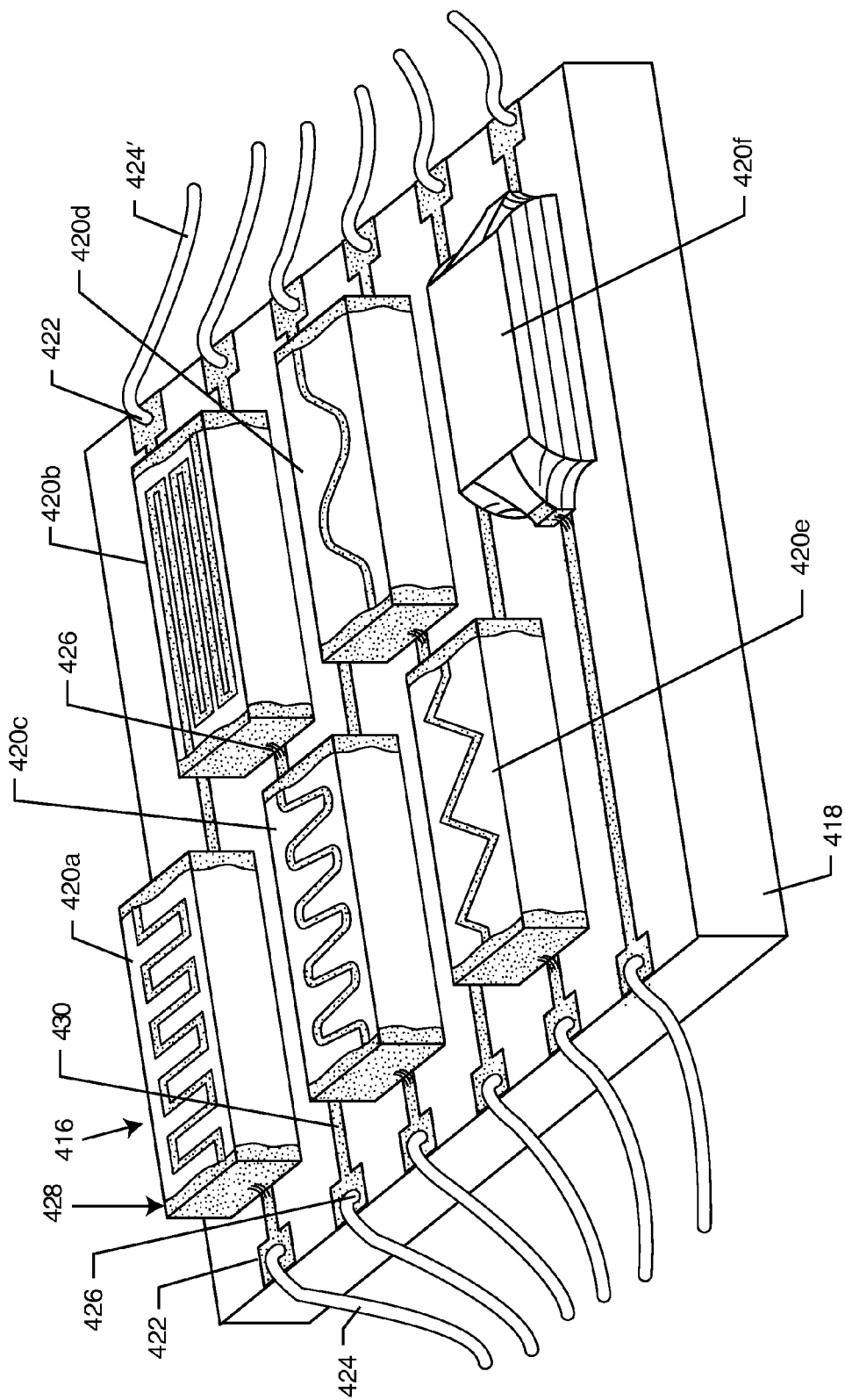
FIG. 83 is an exposed perspective view taken along the line 83-83 in FIG. 81, showing one of many possible variations of the multiple bandstop filter array of FIG. 81.

Referring to FIG. 60, one can see that any of the inductor circuit traces 262 from FIG. 83 of US 2007/0112398 could also be printed or deposited right on top of the MLCC capacitor 182 to form MLCC-T 254'. In this case, they do not need to be embedded and co-fired within the entire ceramic capacitor. The advantage here is that low cost MLCCs which have been produced from very high volume commercial capacitor operations could be utilized and the inductor trace 262 could be printed on as a supplemental operation. The inductor trace 262 could also be placed on its own substrate which could then be co-bonded to a monolithic ceramic capacitor which is essentially equivalent to the structure previously shown in FIG. 60.

Figure 61:
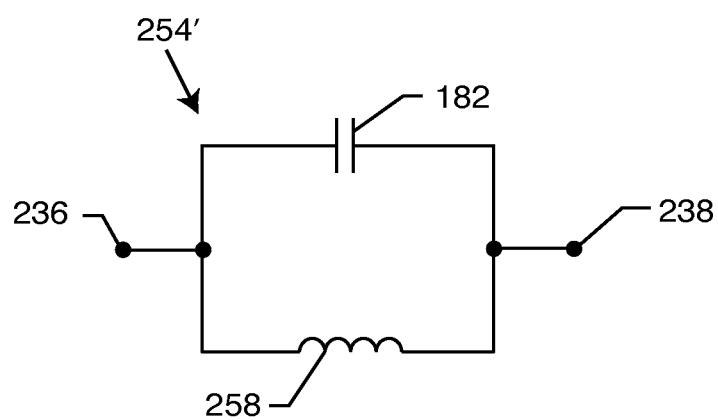
FIG. 61 is a schematic diagram of the MLCC-T of FIG. 60.

FIG. 61 is the schematic diagram of the FIG. 60 MLCC-T 254'. The inductor 258 imprinted onto the capacitor 182 could be made of pure platinum or pure gold so that it would be biocompatible and suitable for direct exposure to body fluids. This is a very convenient rectilinear (flat) geometry in that it is readily adaptable to electrodes that are typically used for neurostimulators, deep brain stimulators, spinal cord stimulators and the like. Coaxial parallel TANK circuits are more applicable to insertion through veins like the subclavian vein and down through the valves of the heart for convenient insertion into the right ventricle. Coaxial geometries are also particularly adapted where the physician must use surgical tunneling techniques to insert an electrode. For example, tunneling techniques are commonly used for neurostimulators to insert a lead wire to stimulate a particular nerve or muscle in a paralyzed patient. The technology and invention described above is also applicable to any type of passive component array including low pass filters, high pass filters, bandstop filters and series resonant (L-C) trap filters.

Figure 62:
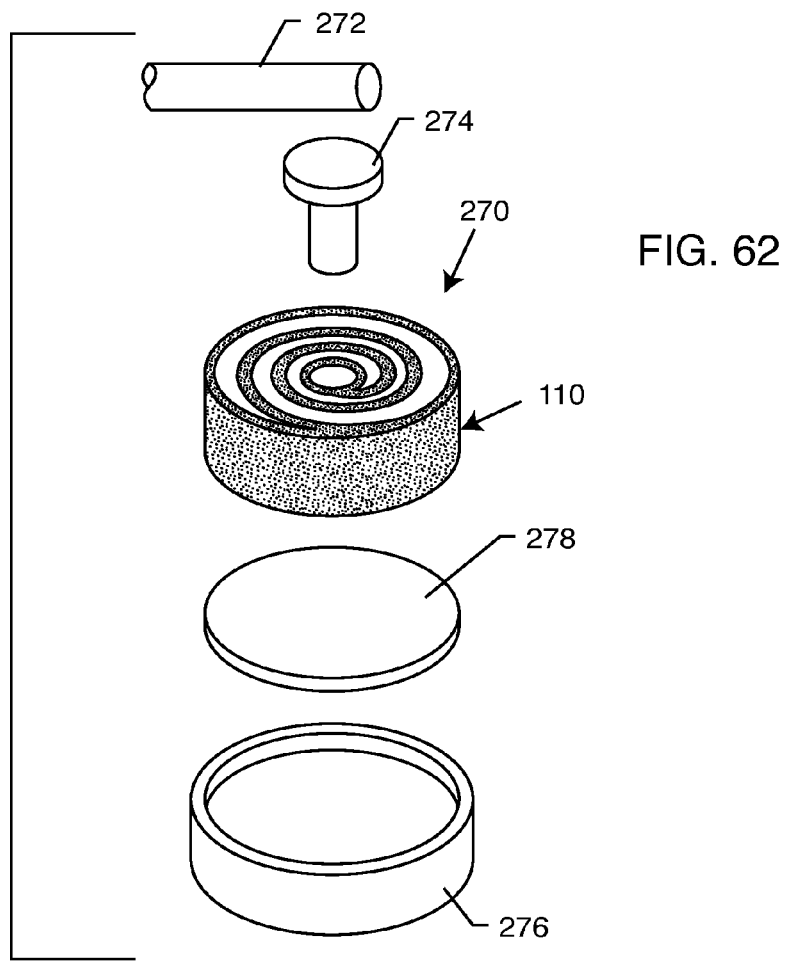
FIG. 62 is an exploded perspective view of a distal electrode pad applicable to a wide variety of neurostimulator applications.
Figure 63:
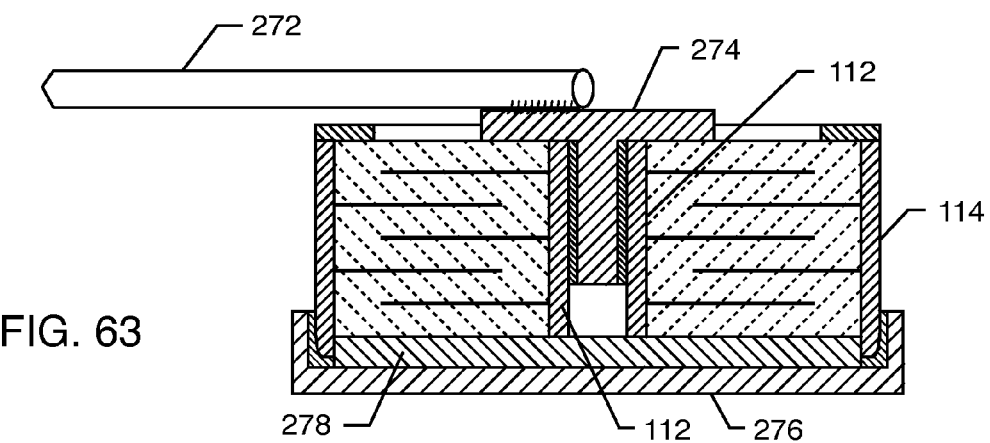
FIG. 63 is a vertical sectional view of the components illustrated in FIG. 62, in their assembled configuration.

FIGS. 62 and 63 describe alternative ways of accomplishing the same thing using a feedthrough capacitor structure. In this case, the inductor 270 has been printed onto the top of the capacitor 110 or attached to the capacitor by means of a supplemental substrate. Lead wire 272 is connected to the capacitor's internal diameter metallization 112 using an intermediate contact plate 274. The electrode 276 is electrically and mechanically attached to the capacitor outside diameter metallization 114, but electrically insulated from the internal metallization 112, such as with an insulative pad or liner 278.

Figure 64:
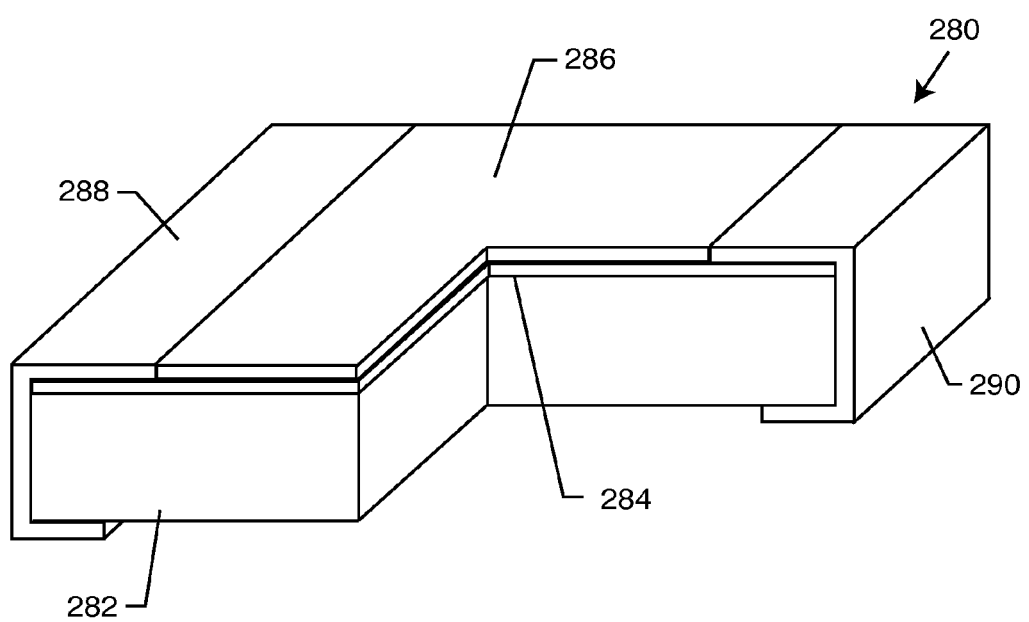
FIG. 64 is a partially fragmented perspective view of monolithic chip resistor embodying the present invention.

FIG. 64 illustrates a chip resistor 280. Chip resistors can embody either thick film or thin film technology. FIG. 64 illustrates an implantable chip resistor 280 which comprises a nonconductive body 282 or substrate of biocompatible and nonmigratable material such as alumna ceramic. A thick or thin film resistive element 284 is deposited on top of the body 282. This forms a conductive electrode with a volume resistivity and thickness that is consistent with the overall resistance value as measured between termination surfaces 288 and 290. In other words, the resistivity and the thickness of the deposited layer 284 are both adjusted in order to control the overall resistance. In addition, the overall physical dimensions of the chip are important. For example, if the chip was longer and thinner, you would have greater resistance and so on. The chip electrode resistance element 284 is typically covered by a protective coating 286. Resistance element 284 is constructed of a biocompatible and non-migratable material in accordance with the present invention. Termination surfaces 288 and 290 are applied in a manner very similar to previously described monolithic ceramic capacitors (MLCCs). These conductive termination surfaces are also of biocompatible and non-migratable materials and are affixed to the main body 282. This allows for convenient electrical attachment of leadwires or circuit traces to the chip resistor 280.

Figure 65:
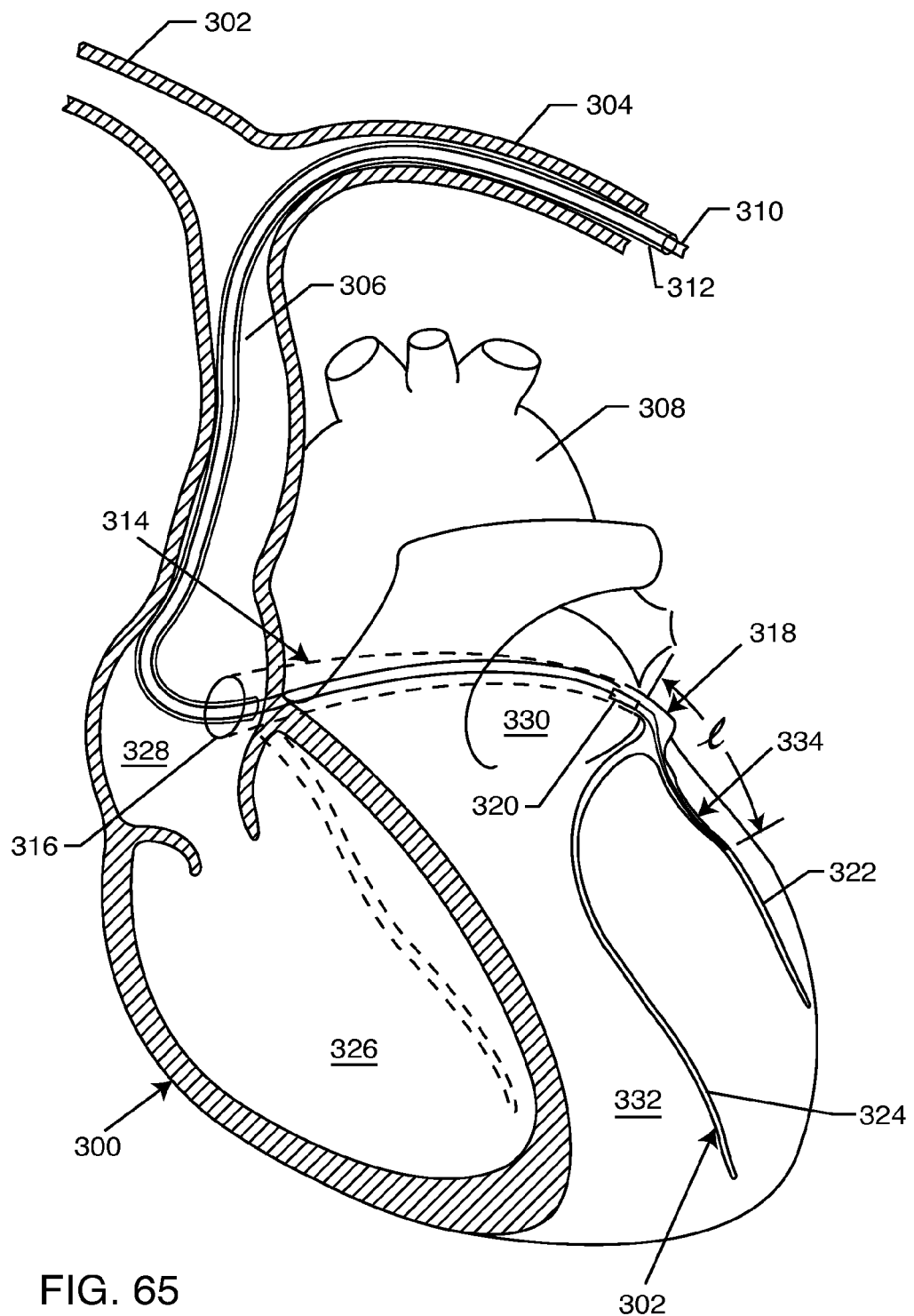
FIG. 65 is a diagrammatic representation of the human heart, showing a left ventricular endocardial lead system.

FIG. 65 is a diagrammatic representation of a human heart 300 which includes right and left subclavian veins 302 and 304 respectively, the superior vena cava 306 and the aorta 308. A lead wire 310, which is typically routed from a biventricular cardiac pacemaker or a biventricular implantable cardioverter defibrillator (ICD) (which are not shown), is routed through a catheter 312 and directed, in this case, through the left subclavian vein 304 and then down through the superior vena cava 306 and into the coronary sinus 314. The leadwire 310 must first enter the coronary sinus ostium 316 where the implanting physician selects the correct location. The coronary sinus 314 is actually divided into two zones: the first part (on the left) is known as the coronary sinus 314; and the second part (on the right) is called the great cardiac vein 318. The great cardiac vein 318 wraps around the back of the left ventricle. A bandstop filter 320 is intended to be placed ideally near the end of the great cardiac vein 318 where it breaks into several venous branches. These branches are called the posterior branch, the lateral branch 322 and the anterior branch 324. A more comprehensive name, for example, would be the interventricular branch.

One can also see the right ventricle 326 and the right atrium 328. Also shown are the left atrium 330 and the left ventricle 332. The ideal location for a proximal bandstop filter 320 is shown. An ideal length for the proximal bandstop filter 320 would be between 5 and 7.5 mm in length. At this particular location, at the end of the great cardiac vein 318, cardiac motion is relatively small and fibrotic tissue will tend to encapsulate the bandstop filter 320 and its lead wires 310 and thereby attach it/fixate it in position in this relatively low motion region. This is a particular advantage, in that the lead 310 will remain highly reliable and resistant to breakage. Because of the relatively large diameter of the coronary sinus 314 and the great cardiac vein 318, this portion of the lead wire system, including the bandstop filter 320, can be of much larger diameter (for example, 7 or 8 French as shown in FIG. 66). Beyond this point, where the great cardiac vein 318 branches, the venous systems become much smaller. In general, these branches are below 6 French in diameter and ideal electrode sizes go all the way down to 3 French. FIG. 66 shows the relationship between French size, millimeters and inches. Since left ventricular pacing is important for cardiac resynchronization and treatment of congestive heart failure, a lead wire reduction should occur at the point of egress of the bandstop filter 320 allowing insertion of electrodes into the small diameter venous system in the proper position outside the left ventricle 332.

The primary benefit of locating the bandstop filter 320 in the coronary sinus 314 and/or great cardiac vein 318 is that the diameter of the bandstop filter 320 itself can be larger making it much easier to manufacture. The distal portion 334 of the lead 310 from the bandstop filter 320 is smaller (3 to 6 French size) for easier employment and navigation into the branch veins of the left ventricle 332. Secondary benefits beyond the diameter of the bandstop filter 320 include the length of the bandstop filter. Entering into and navigating the coronary sinus 314 and great cardiac vein 318 generally involve larger bend radii compared to accessing and navigating the branch vessels. Therefore the portion of the lead 334 that traverses through and resides in the branch vessels must be very small and very flexible, not having a stiff section longer than approximately 1.5 mm as a rule of thumb. Rigid sections of the lead 310 measuring longer than 1.5 mm can impede the ability to navigate around the tight corners and bends of the branch vessels. In the coronary sinus 314 and great cardiac vein 318, however, there is substantially more latitude, and stiff sections of the lead could approach 5 mm or even 7.5 mm without drastically impeding deliverability. A secondary benefit of locating the bandstop filter 320 in the coronary sinus 314 or the great cardiac vein 318 has to do with MRI image artifacts. Although the image artifact will be quite small due to avoiding the use of ferromagnetic materials, it is still beneficial to locate the bandstop filter 320 away from the coronary arteries, ventricular wall motion or other anatomies/physiologies/pathologies of most interest. If a bandstop filter 320 is located in the coronary sinus 314, however, it could generate small artifact in the vicinity of the valves. Another benefit of having the bandstop filter 320 located in the coronary sinus 314 or the great cardiac vein 318 is that its rigidity provides a foundation on which fixation fixtures may be more strategically utilized. For example, one or more tines could originate from the region of the lead where the bandstop filter 320 resides. Additionally, rigidness of the bandstop filter 320 makes the tines more effective in their engagement of the vessel walls. Alternatively, a rigid portion of the lead 360, skillfully navigated beyond a corner or bifurcation, can function as a fixation mechanism that proves difficult or requires skill to track the lead.

Figures 67, 68:
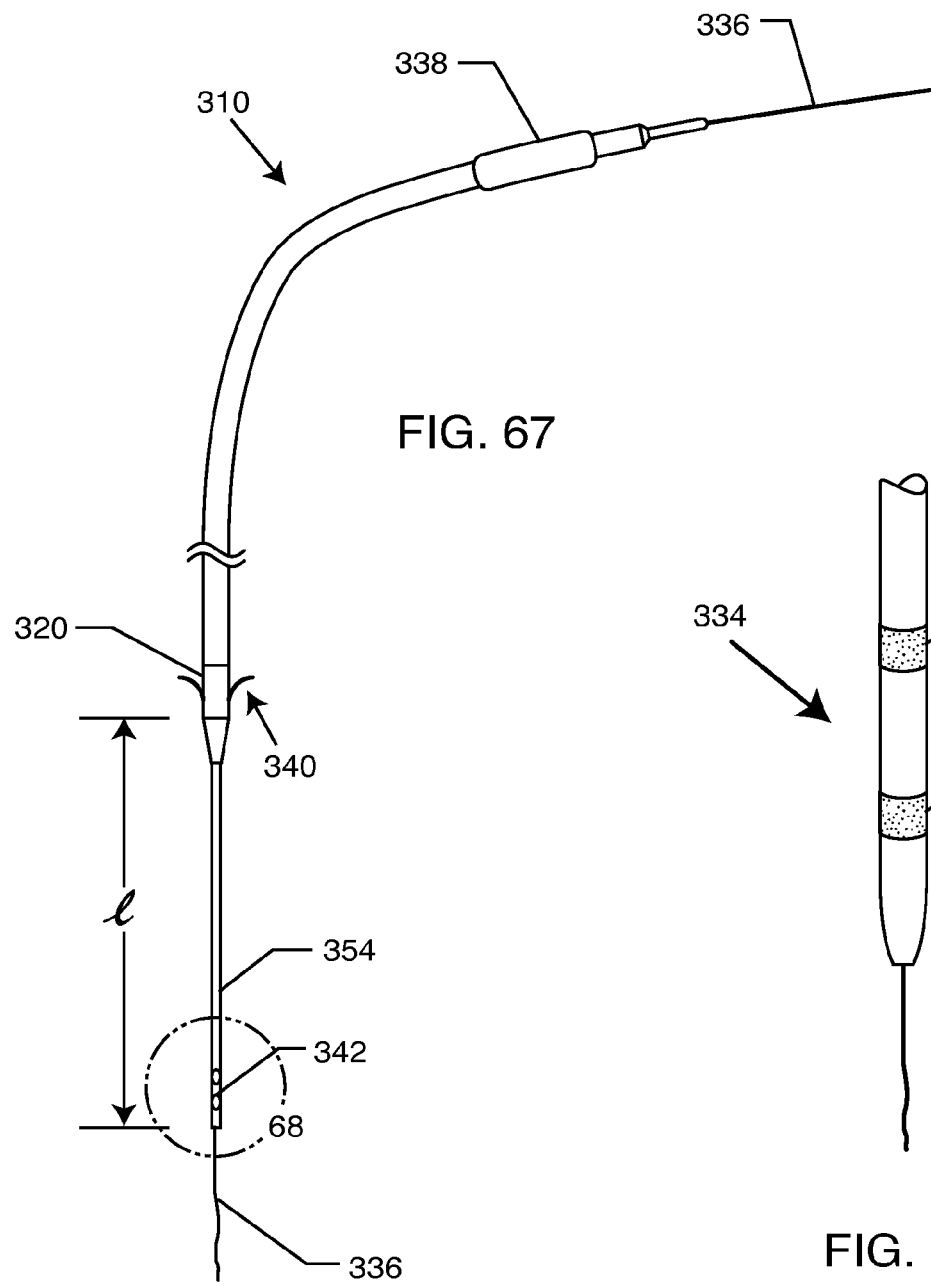
FIG. 67 is an enlarged perspective view of the lead system of FIG. 65.
FIG. 68 is an enlarged view of the distal lead taken generally of the area indicated by the line 68 in FIG. 67.

FIG. 67 is an enlarged perspective view of the lead wire system 310 taken from FIG. 65. One can see that there is a guide wire 336 which is common in the prior art for inserting into position prior to sliding the lead wire system 310 down over it. A terminal pin 338 is designed to plug into the implantable medical device, such as a pacemaker or ICD. The bandstop filter 320 is shown at the point where the lead wire 310 would be reduced from 6-9 French down to 3-6 French. Optional fixation tines 340 are shown which may be affixed to the bandstop filter 320. By way of reference, the French scale is related to both diameter in millimeters (mm) or inches. For example, 7 French is 2.3 mm (0.092 inch) in diameter and 3 French is only 1 mm in diameter (0.039 inch). The length (l) of the reduced diameter lead wire section 334 can be adjusted in accordance with the branch vein into which the lead system is being inserted in the desired location of the electrodes 342. Below the electrodes 342 is the other end of the guide wire 336. Once the electrodes 342 are in the proper position and the system has been tested, the guide wire 336 is typically removed. A particular advantage of the lead system 310 as shown in FIG. 67 is that no new deployment instruments or catheters are required. In other words, this system that includes the bandstop filter 320 is backwards compatible with all known deployment systems. It is also very important that the lead wire system 310 is designed to be extracted in the case of a broken lead, defective lead or infected lead. The lead wire system illustrated in FIGS. 67 and 68, is also backwards compatible with current (prior art) mechanical and laser lead extraction technologies.

Figure 69:
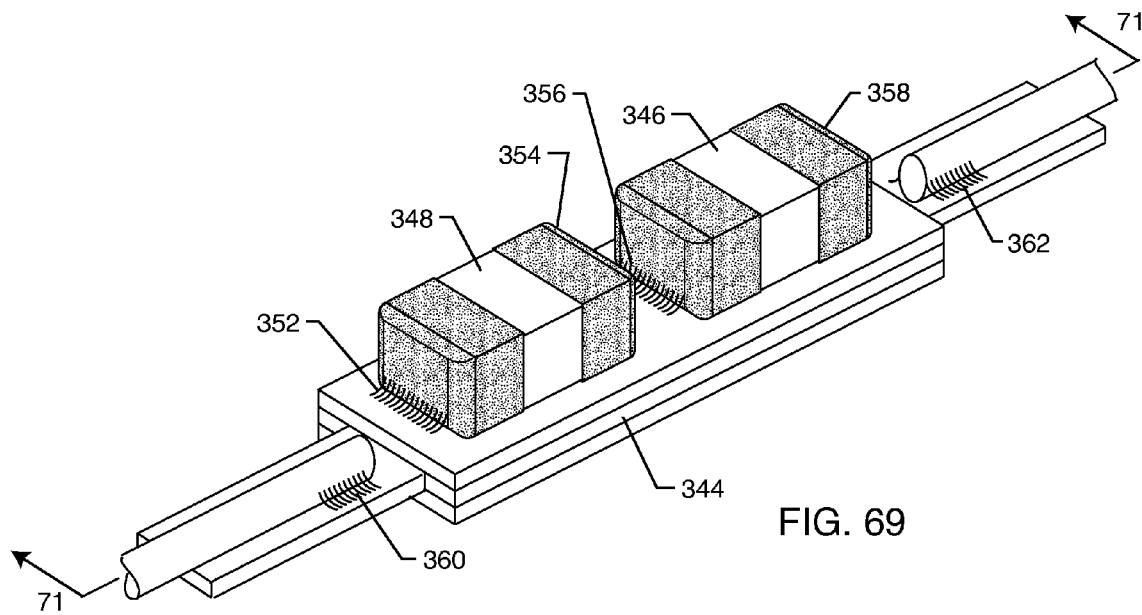
FIG. 69 is a perspective view of a multilayer flex cable onto which a chip capacitor and a monolithic chip inductor are mounted.
Figure 70:
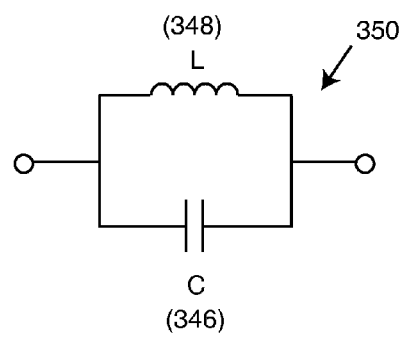
FIG. 70 is an electrical schematic illustrating that the chip inductor and capacitor mechanically disposed in series on the circuit board of FIG. 69 are electrically connected in parallel to form a bandstop filter.

FIG. 69 illustrates a multilayer flex cable 344 onto which capacitor 346 and monolithic ceramic chip inductor 348 are mounted. Internal circuit traces place the inductor 348 and the capacitor 346 in parallel forming the bandstop filter 350 as shown in the schematic diagram of FIG. 70. This forms an inline bandstop filter which is very suitable for placement within the distal electrode illustrated in FIGS. 67 and 68. In FIG. 69 one can see that the entire bandstop filter assembly is not hermetically sealed. This is particularly desirable to keep the French gauge size as small as possible. There are electrical connections 352-362, all of which are biocompatible and are formed of non-migratable materials in accordance with the present invention.

Figure 71:
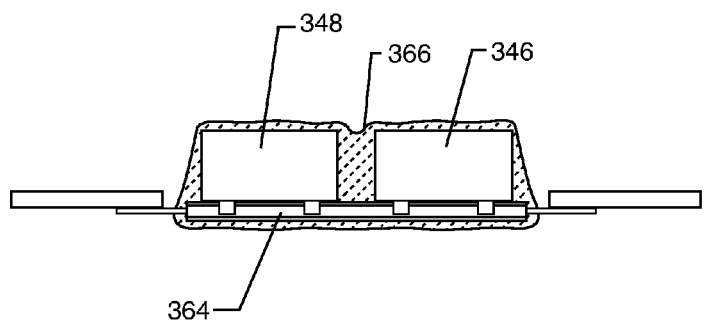
FIG. 71 is a cross-sectional view taken generally along the line 71-71 from FIG. 69.

FIG. 71 is a cross-sectional view taken generally from line 71-71 of FIG. 69, wherein one can see the cross-section of the inductor 348 and the capacitor 346 and also the circuit flexible substrate 364. There is an insulating material 366 which is generally a thermal setting non-conductive biocompatible polymer which provides protection and mechanical robustness to the overall package.

Figure 72:
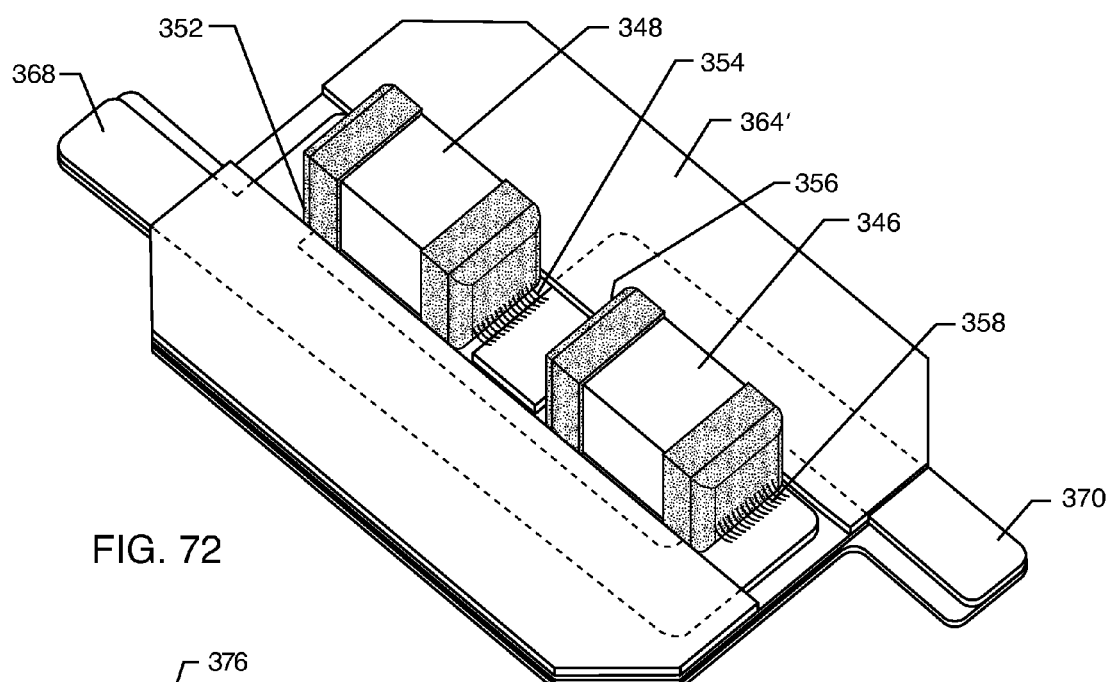
FIG. 72 is a perspective view of an alternative embodiment wherein the chip inductor and chip capacitor are mounted on a flexible circuit substrate.
Figure 73:
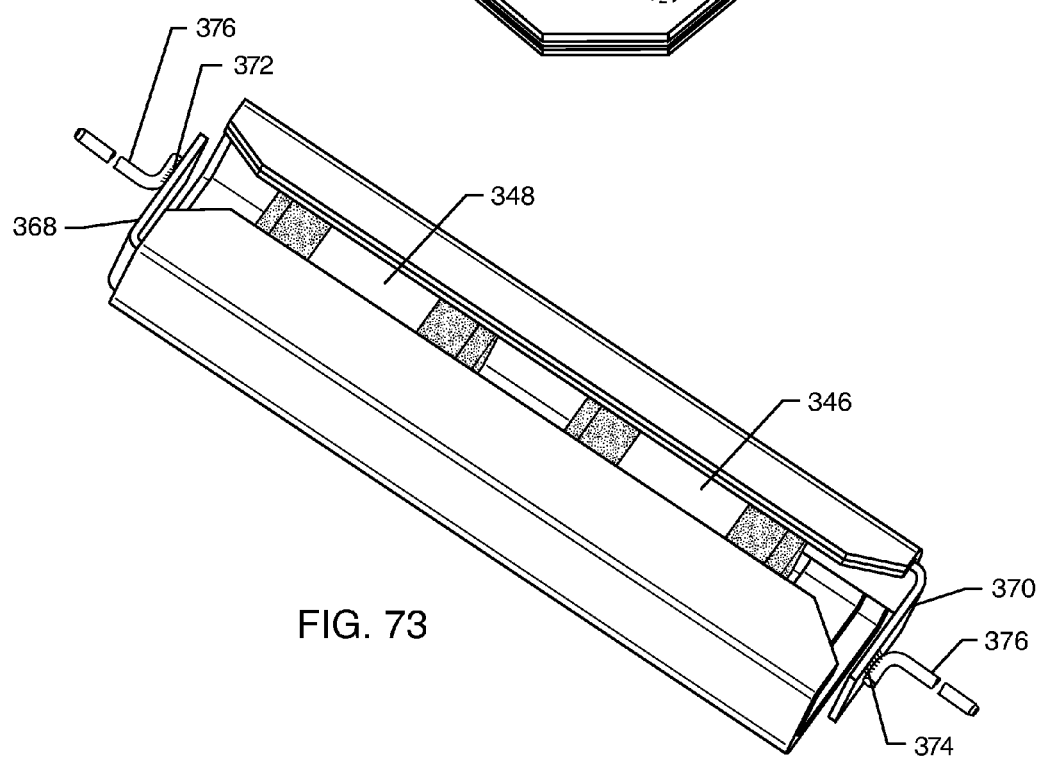
FIG. 73 is a view of the assembly of FIG. 72, wherein the circuit substrate is folded up for insertion into a hermetic cylinder.

FIG. 72 illustrates an alternative embodiment wherein a flexible circuit substrate 364' is shown. For robotic manufacturing, it is highly desirable that the circuit substrate be laying flat while the pick and place robots place the inductor and the capacitor components. As illustrated in FIG. 73, this is then folded up so that it will fit conveniently into a cylinder or other suitable protective housing. Referring once again to FIG. 72, one can see that there are electrical connections 352-358, which again are a biocompatible non-migratable material in accordance with the present invention. Also shown in FIG. 72 are conductive surfaces 368 and 370. As shown in FIG. 73, these can also be folded back. These conductive surfaces are convenient for attachment into the leadwire system as previously described in FIGS. 65, 67 and 68. Referring once again to FIG. 73, there are two laser welds 372 and 374 which are used to attach a typical NP35N alloy leadwire 316 to the bandstop filter structure. Laser welding of biocompatible materials meets all of the requirements of the present invention as to biocompatibility and non-migratable materials.

Figure 74:
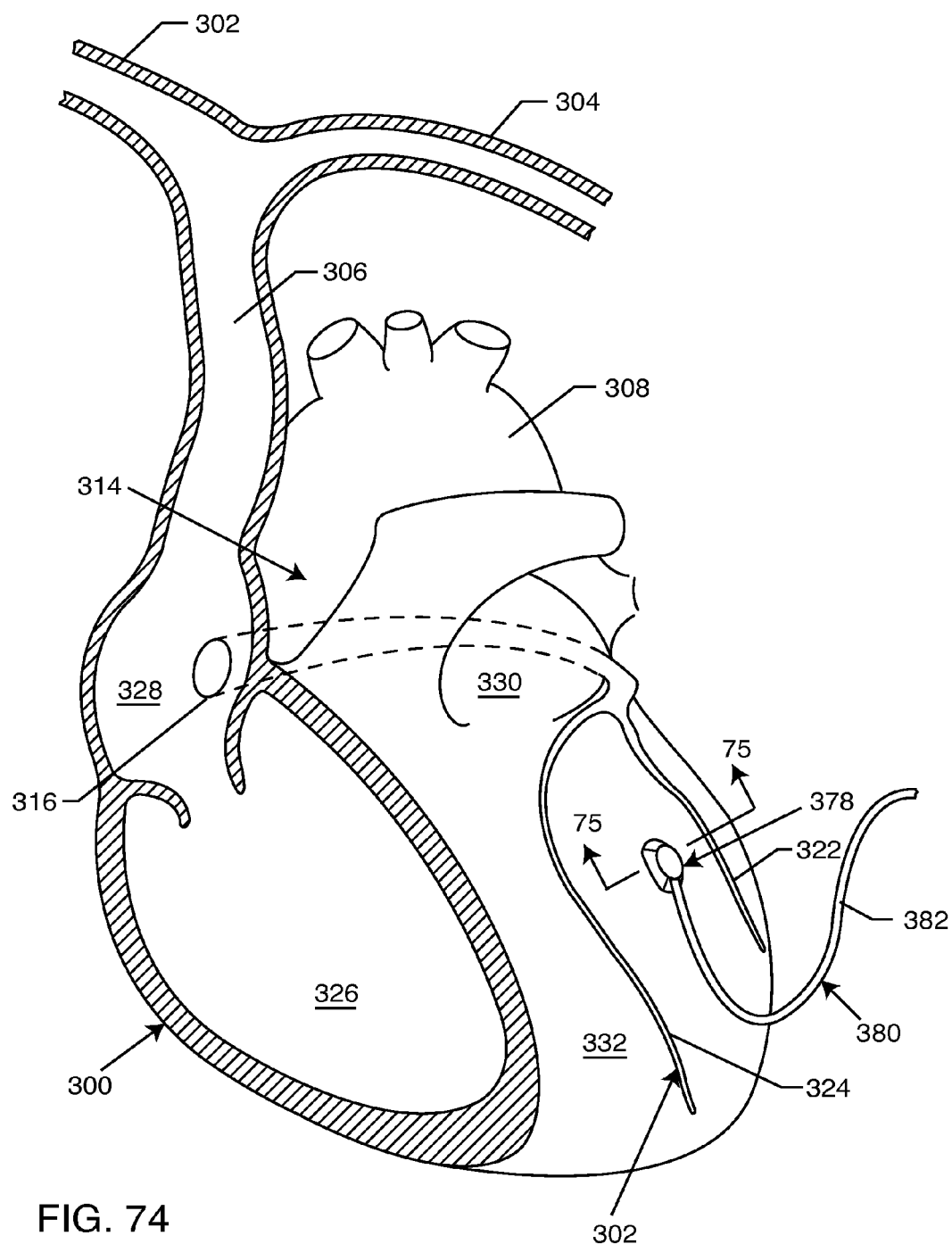
FIG. 74 is a diagrammatic representation of the human heart, showing epicardial leadwire attachment to the outside of the left ventricle.

FIG. 74 is a diagrammatic representation of the human heart similar to that illustrated in FIG. 65. However, in this case, external (epicardial) electrodes 378 are attached outside and to the left ventricle 332 by means of epicardial leads 380. A sutureless myocardial lead 380, 382 is shown affixed to the outside of the left ventricle 332. This methodology is well known and generally involves an insertion between the ribs outside of the heart and a screwdriver type feature to affix the sutureless epicardial lead tip electrode 378 in place. Epicardial leads may also have a suture feature which is also well known in the art, which can have a helical or other configuration type tip. The present invention can be extended to any type of external (epicardial) electrode 378 or satellite pacer affixed to the outside of the heart, particularly outside of the left ventricle.

Figure 75:
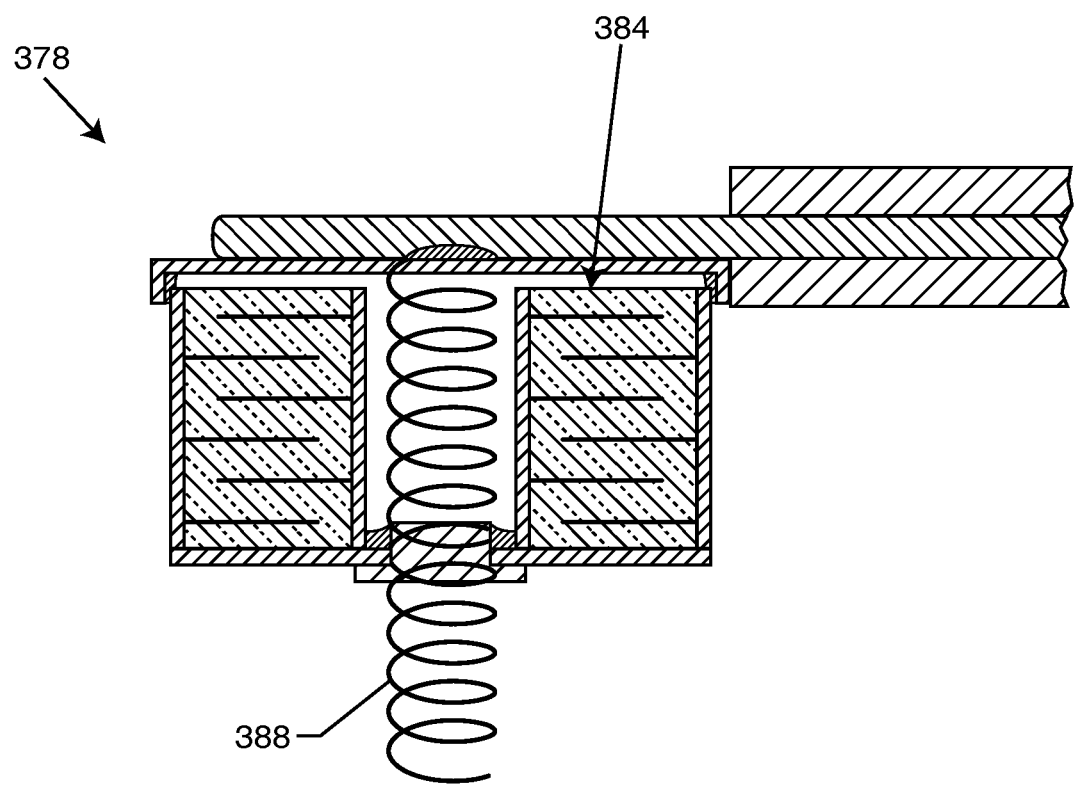
FIG. 75 is a cross-sectional view of an epicardial lead embodying a bandstop filter taken generally along the line 75-75 in FIG. 74.
Figure 76:
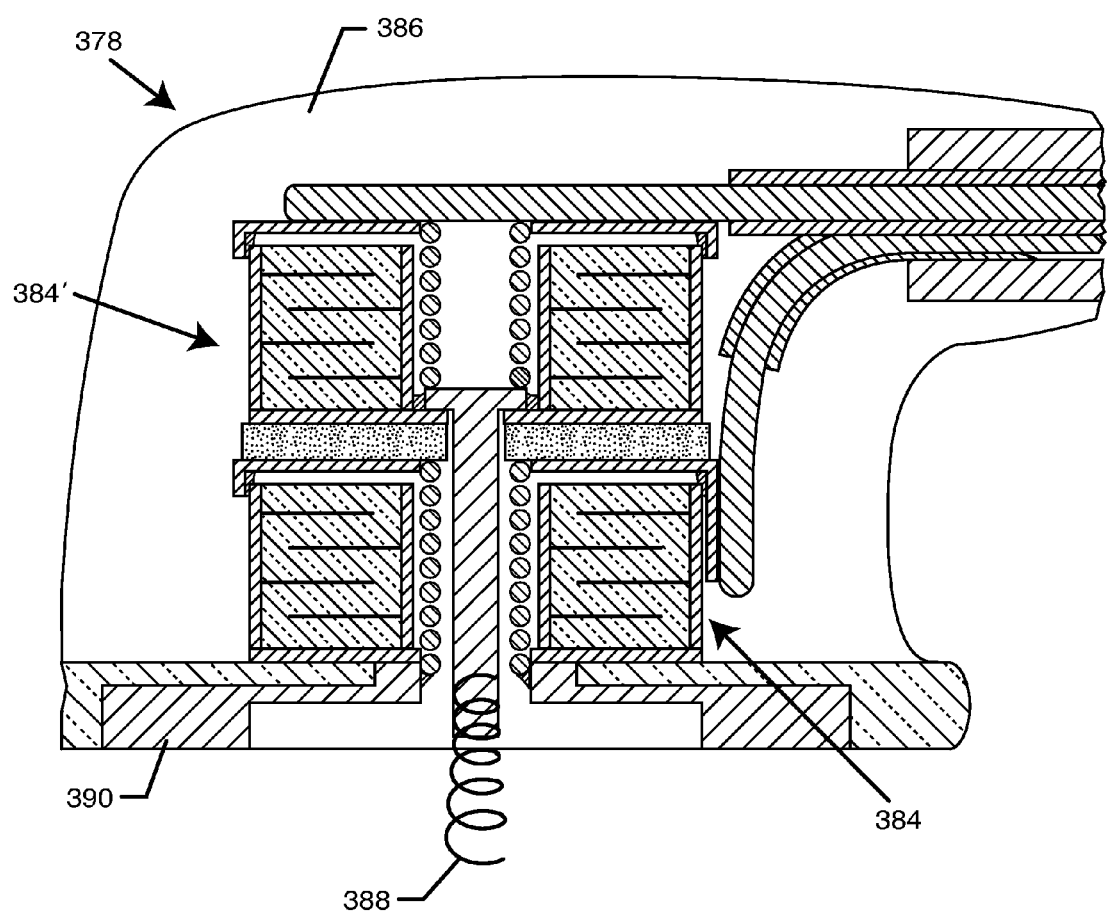
FIG. 76 is an alternative epicardial lead tip taken generally along the line 75-75 in FIG. 74.

FIG. 75 is a cross-sectional view taken generally along line 75-75 of FIG. 74, illustrating an epicardial lead electrode assembly 378 which includes a bandstop filter 384. In the prior art, the epicardial lead electrode assembly 378 is typically over-molded with silicone rubber 386 (FIG. 76). The assembly shown in FIG. 75 is self-affixing to the myocardial tissue by a helical electrode structure 388. Typically this electrode is affixed into the myocardium by 3½ mechanical turns and is made of platinum-iridium alloy or equivalent biocompatible material. The helical electrode tip 388 is affixed into the myocardial tissue by a screwdriver type turning surgical tool. The bandstop filter 384, as illustrated in FIG. 75, is taken generally from FIG. 42 of U.S. Patent Application Publication No. 2007/0112398, filed Nov. 9, 2006. Almost all of the other bandstop filter embodiments that are disclosed in U.S. Patent Application Publication No. 2007/0112398 can be incorporated into the epicardial lead 378 in FIG. 75. For example the bandstop filters shown in U.S. Patent Application Publication No. 2007-0112398, FIGS. 35, 37, 42, 58, 65, 69, 70, 80, 85, 87, 94, 115, 118, 128, 130, 132, 133, 141, 142, 149, 151, 156, 157, as well as any of the designs of U.S. Provisional Patent Application No. 60/968,662, are all readily adaptable into the bandstop filter 320 and 384.

FIG. 76 is very similar to the epicardial lead electrode assembly 318 shown in FIG. 75, except that it has a novel ring structure 390 associated with a bandstop filter chip 384. This epicardial bipolar electrode also has a bandstop filter 384' in series with its helical tip electrode 388. Not shown, but obvious to those skilled in the art, is that a screwdriver type head mechanism can be added for convenient adapting to prior art deployment instruments. Any of the cylindrical bandstop filters described in U.S. Provisional Patent Application No. 60/968,662, filed Aug. 29, 2007, can also readily adapted to any of the novel bandstop filter applications described herein.

Figure 77:
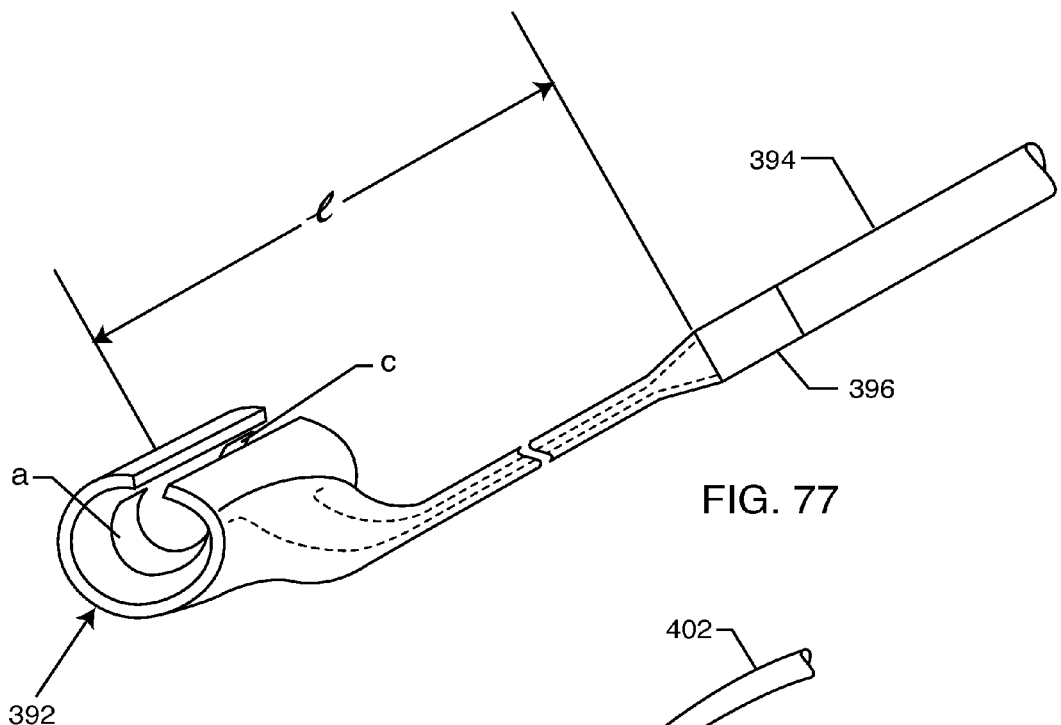
FIG. 77 illustrates a split cylinder cuff electrode designed to wrap around a nerve.

FIG. 77 illustrates a split cylinder cuff electrode 392 embodying two electrodes (Anode (a) and Cathode (c)). This is designed to be inserted by a physician around a nerve. It is a bipolar system typically consisting of a 6-8 French diameter lead body 394. A double bandstop filter chip 396 (two discrete bandstop filter chips in parallel) in accordance with the present invention is located as shown. In general, the cuff 392 is sized to match the diameter of the nerve which passes through its center. The lead body 394, after the double bandstop filter 346, is of a reduced diameter, generally in the 3-4 French range. Not shown is a closing suture which is typically used to draw the cuff together after it's installed.

Figure 78:
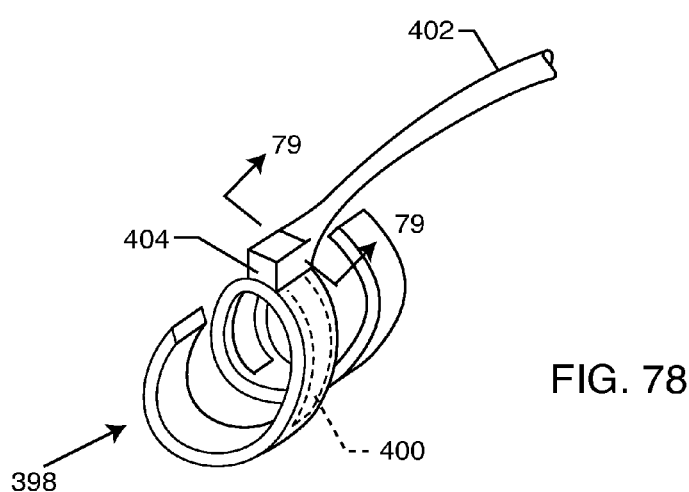
FIG. 78 illustrates a self-sizing helical cuff coil including the bandstop filter chip.

FIG. 78 illustrates helical nerve cuffs 398 which are self-sizing. These incorporate electrode foils 400 which are well known in the art. The lead body 402 is attached to a bandstop filter 404. This can be unipolar or bipolar as shown. The electrode foil 400 can either be etched or stamped and then the termination point where the conductor attaches to the foil is either prepared or fabricated. This is the location to where the bandstop filter 404 is electrically attached and incorporated. The conductors and the foil 400 on the bandstop filter 404 are laid into a split mold and assembled and then silicone is injected into the mold. FIG. 78 illustrates one leg of a bipolar or multipolar lead. Obviously, a bandstop filter 404 would be required for each electrode foil in the multipolar configuration.

Figure 79:
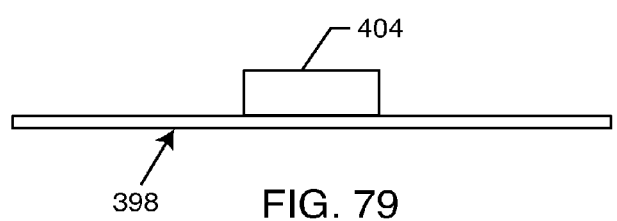
FIG. 79 is a sectional view taken generally along the line 79-79 in FIG. 78.

FIG. 79 is a sectional view taken generally along line 79-79 of FIG. 78.

Figure 80:
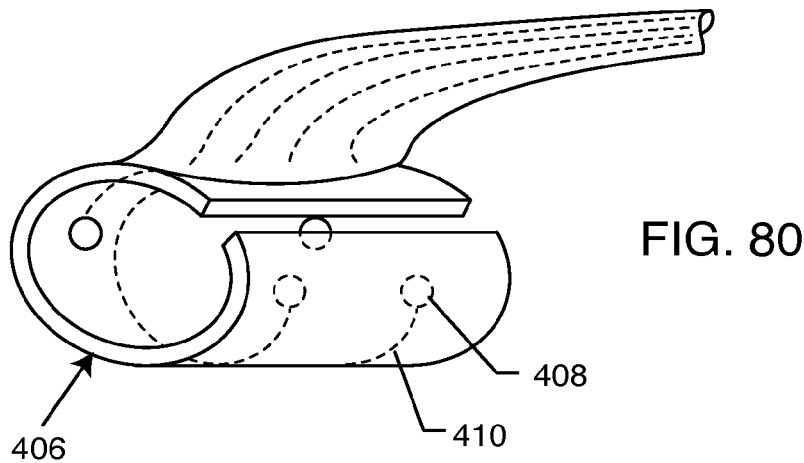
FIG. 80 illustrates a nerve cuff employing a multiplicity of electrodes and bandstop filter chips for a large nerve trunk.

FIG. 80 illustrates a larger multiple cuff nerve electrode 406 for current steering in a large nerve trunk. Various electrodes can be stimulated by trial and error to obtain the optimal result. For example, for pain control, one can try various electrodes and various types of electrical stimulation by trial and error until pain is minimized or eliminated. The multiple parallel filter electrodes 408, similar to that described in FIG. 75, can be placed in conjunction with each one of the conductors 410 as shown.

Figure 81:
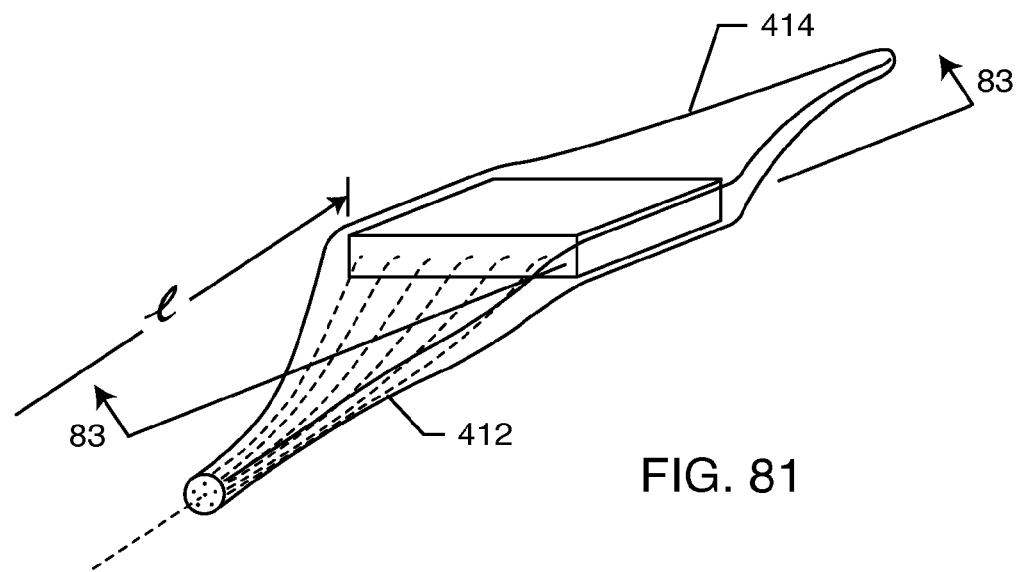
FIG. 81 illustrates one methodology of putting multiple bandstop filter chips in series with the lead wires of the multiple cuff electrode of FIG. 80.
Figure 82:
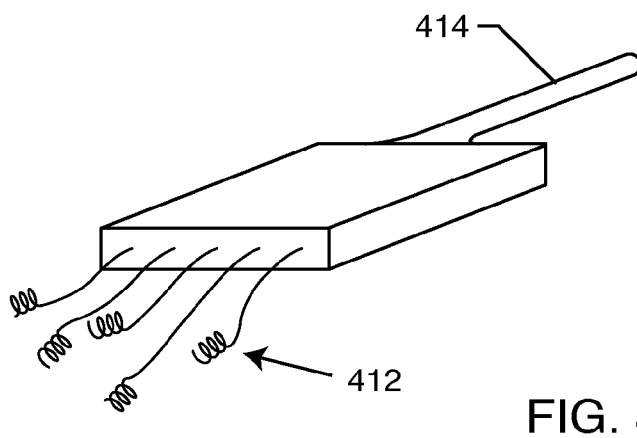
FIG. 82 illustrates a multi-conductor lead body connected to a multiple tank filter chip array that has multiple electrodes.

FIG. 81 illustrates an alternative in that a multiple bandstop filter array 412 is shown in series with the lead body 414. This can in turn be connected to the cuff electrode 406 of FIG. 80 or to the multiple cuff electrodes 392,398 illustrated in FIGS. 77 and 78. It can also be adapted to the multiple single electrodes illustrated in FIG. 82. The multiple bandstop chip as illustrated in FIGS. 81 and 82 can be made in a variety of ways utilizing the technology disclosed in U.S. Patent Application Publication No. 2007/0112398, and U.S. Provisional Patent Application No. 60/968,662, by putting the devices on a substrate next to each other on each lead wire. The structure shown in FIGS. 81 and 82 can be over-molded with silicone or the like to provide reliable mechanical attachment and additional protection from body fluids.

FIG. 83 is taken generally along the line 83-83 from FIG. 81, and illustrates one of many ways to form a multiple array 416 of bandstop filter chips. One can see that there is a thin substrate 418 which can be of alumina or any other biocompatible substrate material known in the prior art. A substrate could also be a flexible substrate, such as a polyimide flex cable. The various meanders on the bandstop filters are for illustration only. Any active or passive electronic network component or component network of the present invention can be similarly designed. Different types of bandstop filters 420a-f (MRI chips) are shown by way of illustrating that there are many ways to construct this multiple array 416. Referring to drawings from U.S. Patent Application Publication No. 2007/0112398, the MRI chips 420a-f are similar to FIGS. 80-85 and FIG. 136 (which is thick film deposited right on the substrate). Imbedded or MEMs components can also be used to form the multiple bandstop MRI filter array 416. In addition, multilayer substrates may be used to increase packaging density. Wirebond pads 422, leadwires 424 and 424' and electrical connections 426 (typically laser welds or gold wirebonds), are also shown. The bandstop filter chips 424a-f have end terminations 428 as shown. There are electrical connections from these end terminations 428 to the circuit traces 430. The entire assembly is desirably over coated, over molded (with silicone or the like), or glass encapsulated to enhance mechanical strength and biocompatibility. Every one of the active or passive electronic network component or component network electrical connections 426 must be done with a suitable biocompatible and non-migratable electrical connection material in accordance with the present invention. There is a similar electrical connection material that's made to each one of the leads. It is critical that this electrical connection material will also be of suitable biocompatible and non-migratable material in accordance with the present invention.

Figure 84:
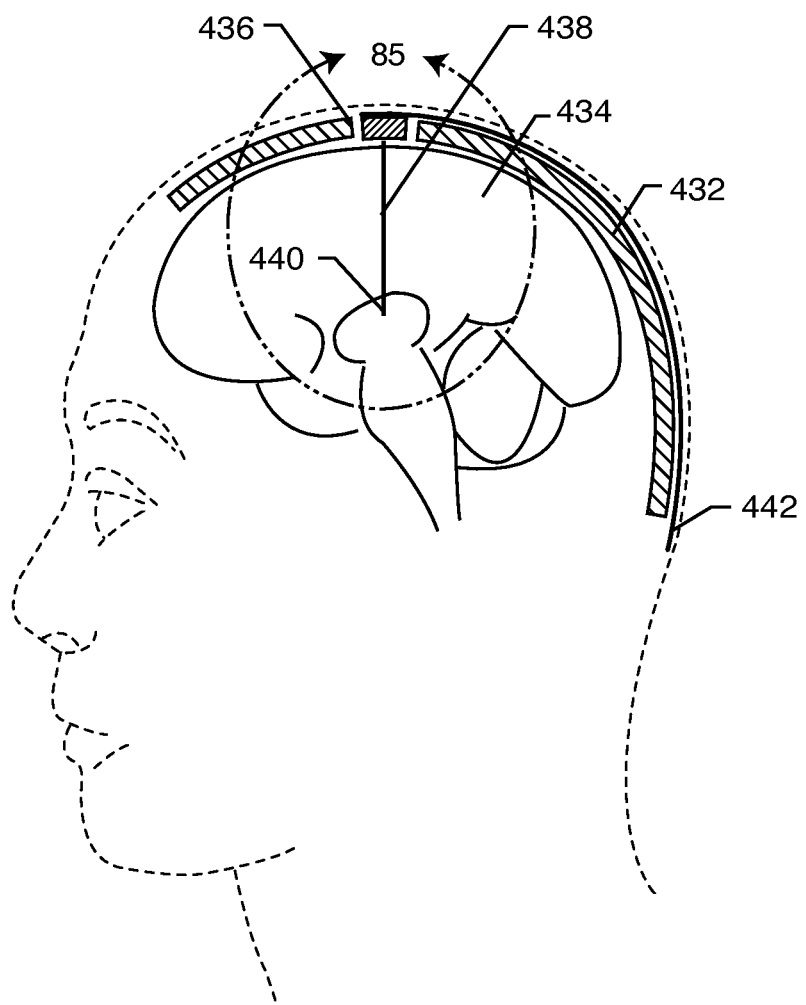
FIG. 84 is a diagrammatic, side cross-sectional view of the human head showing the placement of a deep brain probe and electrode embodying a bandstop filter.

FIG. 84 is a diagrammatic side cross-sectional view of the human head showing the skull 432 and the brain 434. A burr hole 436 is drilled through the skull 432 for placement of deep brain probe 438 with associated electrodes 440. One can see that there is a lead wire body 442 which has been tunneled up underneath the skin and attaches to the deep brain probe 438. One or more bandstop filter chips of the present invention are located inside of the skull burr hole 436. In a preferred embodiment, the top of the deep brain probe 438 and associated bandstop filter would be flush with the top of the skull 432. The lead wire 442 is generally connected to a pulse generator or transmitter which is either implanted or can sit outside the skin. There can also be a receiver which sits on the skin. The deep brain probe 438 can also have a nail head or nail shank.

Figure 85:
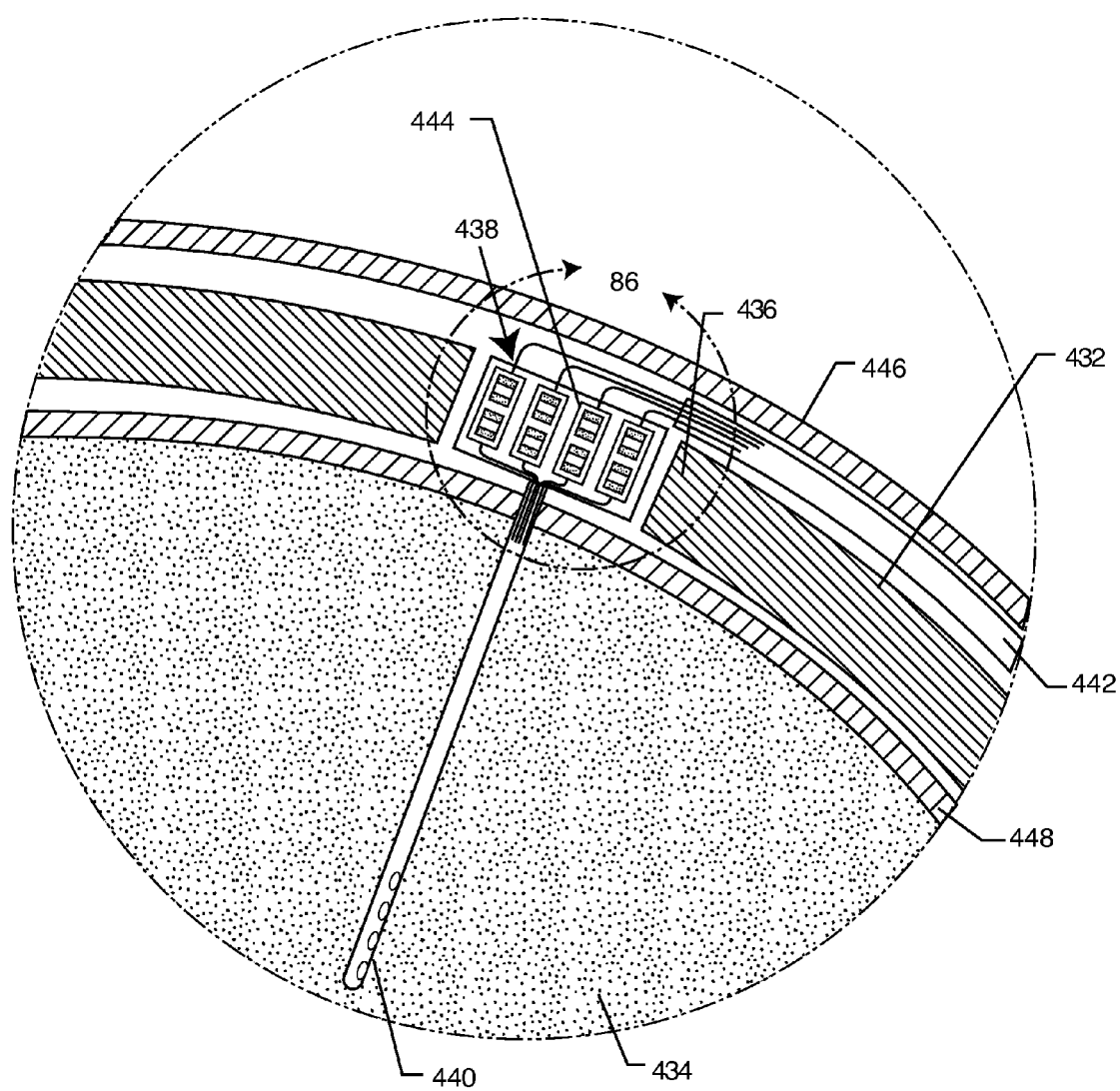
FIG. 85 is an enlarged sectional view taken generally of the area indicated by the line 85 in FIG. 84.

FIG. 85 is an enlarged sectional view of the area indicated by line 85 in FIG. 84, of the deep brain probe 438. Shown is the location of the bandstop filter 444, the skin 446 which covers the skull 432, the lead wire 442, the burr hole 436, dura layer 448 and the brain 434. At the end of the deep brain probe 438 are electrodes 440. Referring to the bandstop filter element 444 of FIG. 85, one can see that it's an inline bandstop filter constructed in a way that was described in connection with FIGS. 69 through 72. There are a number of electrical connections in FIG. 85 that are not shown, but one can see that each one of the leadwires has to be connected to either the component or conductive circuit or circuit trace and that each one of the inductor and capacitor elements must be in turn similarly connected. In addition, electrode leadwires 450 must be connected on the other end. All of these electrical connections are of suitable biocompatible and non-migratable materials in accordance with the present invention.

Figure 86:
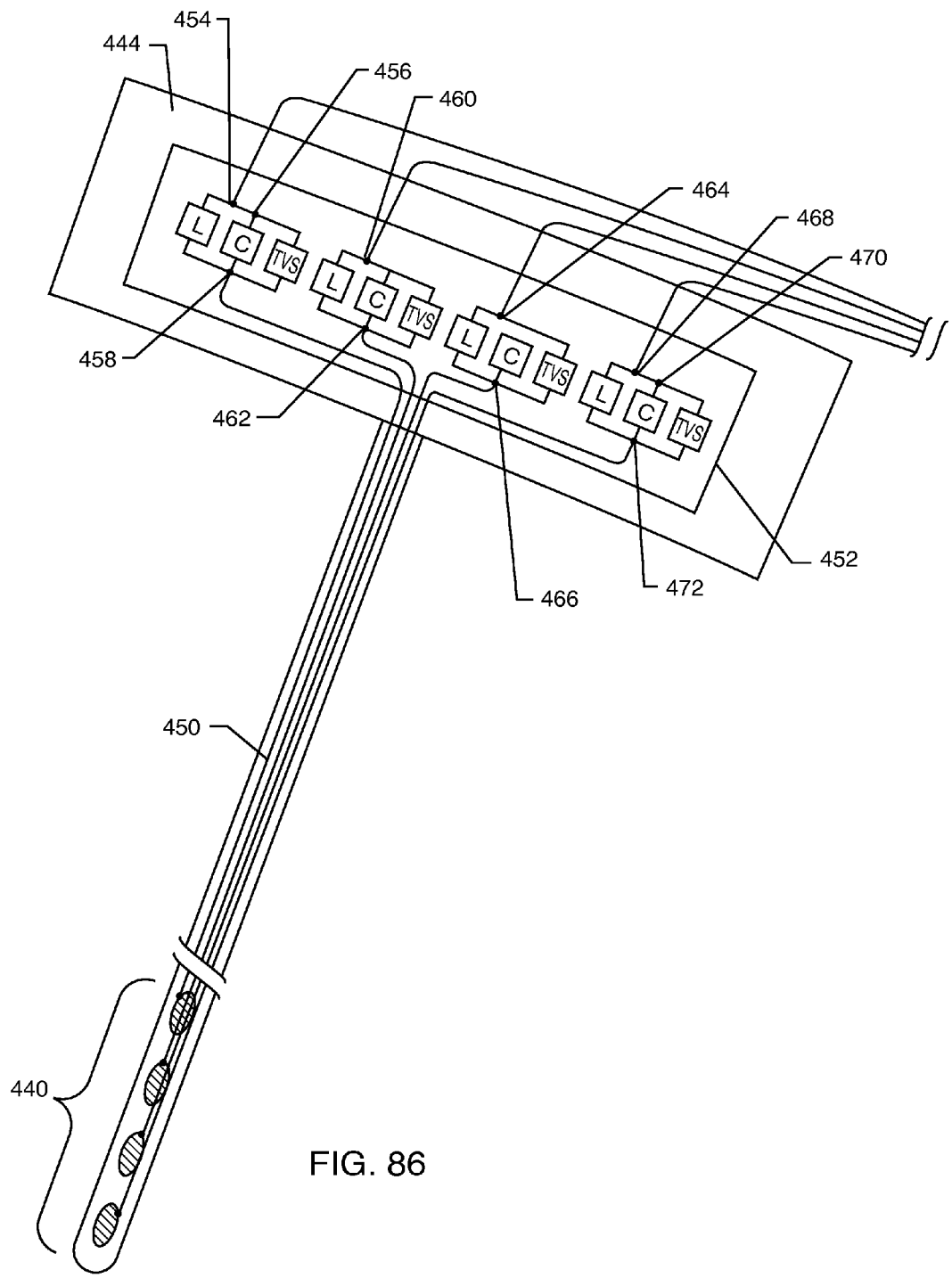
FIG. 86 is an enlarged view taken of the area indicated by line 86 in FIG. 85.

FIG. 86 is taken generally from section 86 of FIG. 85. Shown is an electronic circuit board 452 which is embedded within the electronics module 444. In this case, there are four bandstop filters consisting of an inductor L in parallel with a capacitor C. Also shown is a transient voltage suppressor TVS which is in parallel with each one of the bandstop filter circuits. As described in U.S. Provisional Patent Application No. 61/079,693, this provides protection against automatic external defibrillation (AED) events. In FIG. 86, all of the components are disposed upon circuit board or circuit flex cable 452. Also shown are some of the electrical connections 454-472 which are of course, biocompatible and non-migratable in accordance with the present invention. Internal and external electrical connections to each one of the circuit elements (not shown) are also required in accordance with the present invention. These would be the connections to, for example, the capacitor element metallization on each end. The TVS circuit would provide protection against all types of high voltage transients which could damage delicate electronic circuits. This would be particularly important if the L and C resonator elements were of delicate MEMS type structures.

Figure 87:
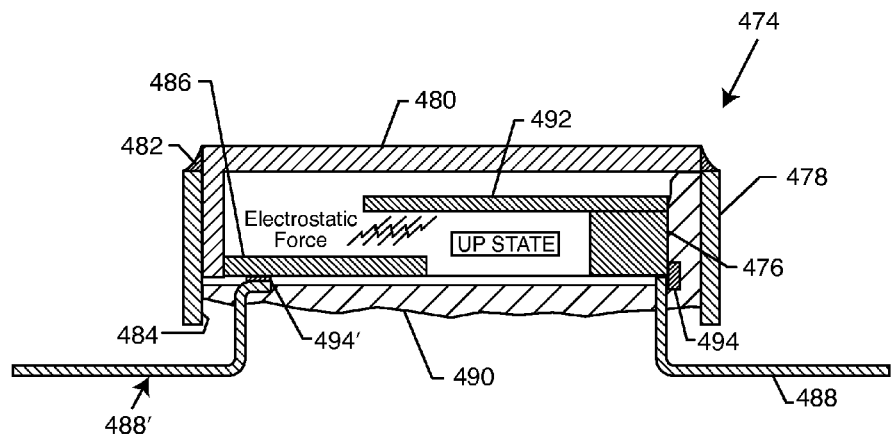
FIG. 87 is a sectional view of a distal electrode pad applicable to a wide variety of neurostimulator and neuromodulator applications, showing the embedded switch in the open position.

FIG. 87 is a cross-sectional view illustrating one form of the novel electronic switch 474 of the present invention. One can see that there is an electronic MEMS switch 416 located within the switch assembly housing 478. In this case, the distal TIP electrode pad 480 has a laser weld or equivalent biocompatible electrical attachment 482 to the surrounding metallization 484 of the ceramic insulator structure 480. The electrode pad 480 is electrically connected to the cathodic contact 486 of the MEMS switch 476. The cathodic contact 486 is rigid in this case and is not free to move. Lead wire 488 is then routed through the flexible neurostimulator pad insulation/encapsulant 490 and is electrically connected to the anodic MEMs contact cantilever 492 as shown. In FIG. 87, the MEMS switch 476 is shown in the up or open state wherein no currents can flow through it. This is the ideal position for MRI imaging or other procedures such as surgical electrocautery (Bovi knife for example) requiring high RF energy.

Figure 88:
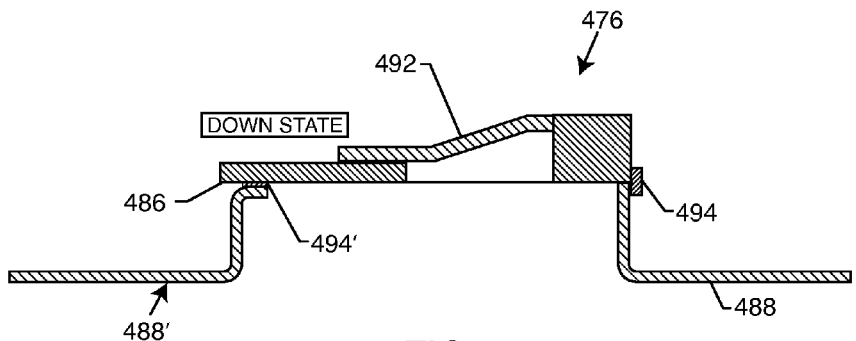
FIG. 88 is a view of the switch of FIG. 87 now shown in the closed position after application of electrostatic or external magnetic force.

FIG. 88 shows the MEMS switch 476 of FIG. 87 in the down or closed state. In this position, biological sensing and therapy signals freely pass through the switch 474. Referring to FIGS. 87 and 88, one can see that there is electrical connection material 494 and 494' which is required to attach leadwires 488 and 488' to the MEMs switch assembly. These electrical connection materials are of biocompatible and non-migratable material in accordance with the present invention.

Figure 89:
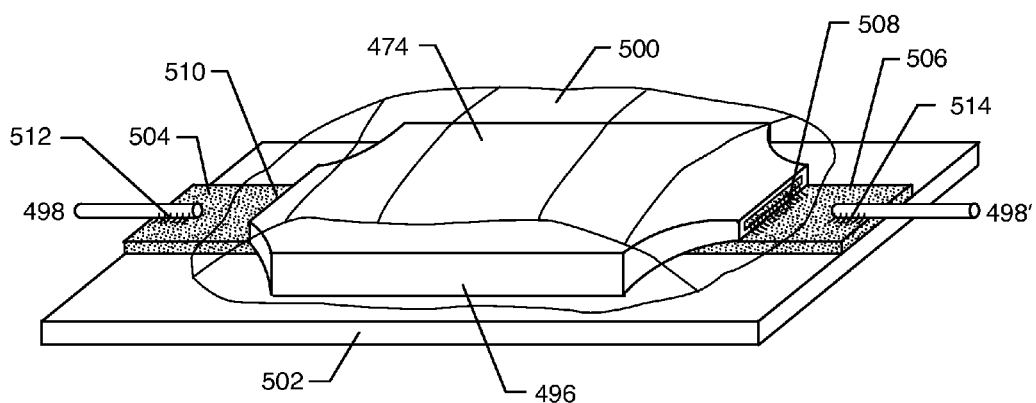
FIG. 89 is a perspective view of an electronic switch which has been embedded on a substrate with a hermetic seal or encapsulant for protection against body fluids.

FIG. 89 illustrates the novel electronic switch assembly 474 of the present invention shown in an encapsulated switch assembly or module 496 convenient for location anywhere in the lead wire 498 circuit. In this case, the entire module 496 has been overlaid with a suitable glass seal 500. This glass seal 500 can be deposited as a frit or molten and then sintered at high temperature. The glass 500 is designed to adhere to the substrate 502 and the wire bond pads 504 and 506 such that it forms an adjunct partial hermetic seal over the entire switching circuitry 496'. Material 500 can be any number of borosilicate or compression glasses or even polymer sealants such as silicone and the like. Electrical connections 508-514 are shown in accordance with the present invention.

FIG. 90 is an electrical schematic drawing of the MEMs switch assemblies previously illustrated in FIGS. 87, 88 and 89.

With reference to FIG. 91, in certain AIMD applications there can be as many as 6, 10, 12, 16 or more electrodes. There is largely a trial and error process after implantation as to which electrode pairs or which electrodes the physician will decide to use. For example, in a deep brain application, the physician will experiment using different electrodes until the desired patient response is achieved. In a cochlear implant application, which typically uses 16 electrodes, the Audiologist will experiment with various electrodes until optimal patient hearing is achieved. A downside of these AIMDs is that an electronic switch would be required in series with each one of those electrodes. FIG. 91 illustrates a novel electronic multiplexing circuit 516. By way of illustration, a single MEMS switch 476 is shown. After the physician determines which of the multiple mini electrodes 518 is the optimal one by using the multiplexing function 520, the physician or technician can switch in the electronic switch 476 in series with that particular circuit. This has the effect of greatly reducing the number of electronic switches required.

As an alternative, instead of switching in an electronic switch, one could utilize a band stop filter as previously described in United States Patent Application Publication Nos. US 2007/0112398 A1; US 2008/0132987 A1; US 2008/0049376 A1; US 2008/0116997 A1; and US 2006/0247684 A1, the contents of which are incorporated herein. By the use of a multiplexing network, the number of bandstop filters can be significantly reduced. If, for example, there were 16 electrodes, one might get away with only 4 electronic switches (or alternatively, bandstop filters consisting of a parallel inductor and capacitor element) to service selectively all 16 electrodes. The techniques as illustrated in FIG. 91 are applicable to any active or passive electronic network component or component network.

FIG. 92 illustrates a typical PNP transistor which could be used as part of the electronic switches as previously illustrated in FIG. 91. Biocompatible transistors can be made of biocompatible materials with suitable biocompatible and non-migratable electrical connections.

FIG. 93 illustrates an inductor chip 522 shown attached to circuit traces 524 and 524'. Referring to the inductor chip 522, one will see that it has metallization bands 526 and 528 as shown. In accordance with the present invention, these metallization bands would be of gold, platinum or other suitable noble or biocompatible or non-migratable material. In addition, there are electrical connections 530 and 532 which are also of biocompatible and non-migratable material in accordance with the present invention.

FIG. 94 is an exploded view of the inductor chip 522 in FIG. 93.

One can see that there are a number of biocompatible dielectric layers 534 used as cover sheets. These are placed on top and bottom to add rigidity and mechanical protection to the internal inductor traces 536 and 538. Inductor trace 536 is to be placed on substrate layer 540 and inductor trace 538 is disposed on layer 542. These are designed to be electrically in series by use of a conductively filled via hole which is continuous through 544 and 544'. The inductor trace material 536 and 538 must be of suitable biocompatible and non-migratable material in accordance with the present invention, such as platinum or gold or the like. Electrically conductive filler material which fills the via hole must also be of suitable biocompatible and non-migratable material in accordance with the present invention. This is a way of illustrating the importance that both the external electrical connections 530 and 532 as previously illustrated in FIG. 93, as well as the internal electrical connection, such as in via hole 544-544' are all equally important to achieve long term biocompatibility.

FIG. 95 is the electrical schematic of the inductor chip 522 illustrated in FIGS. 93 and 94.

Figure 96:
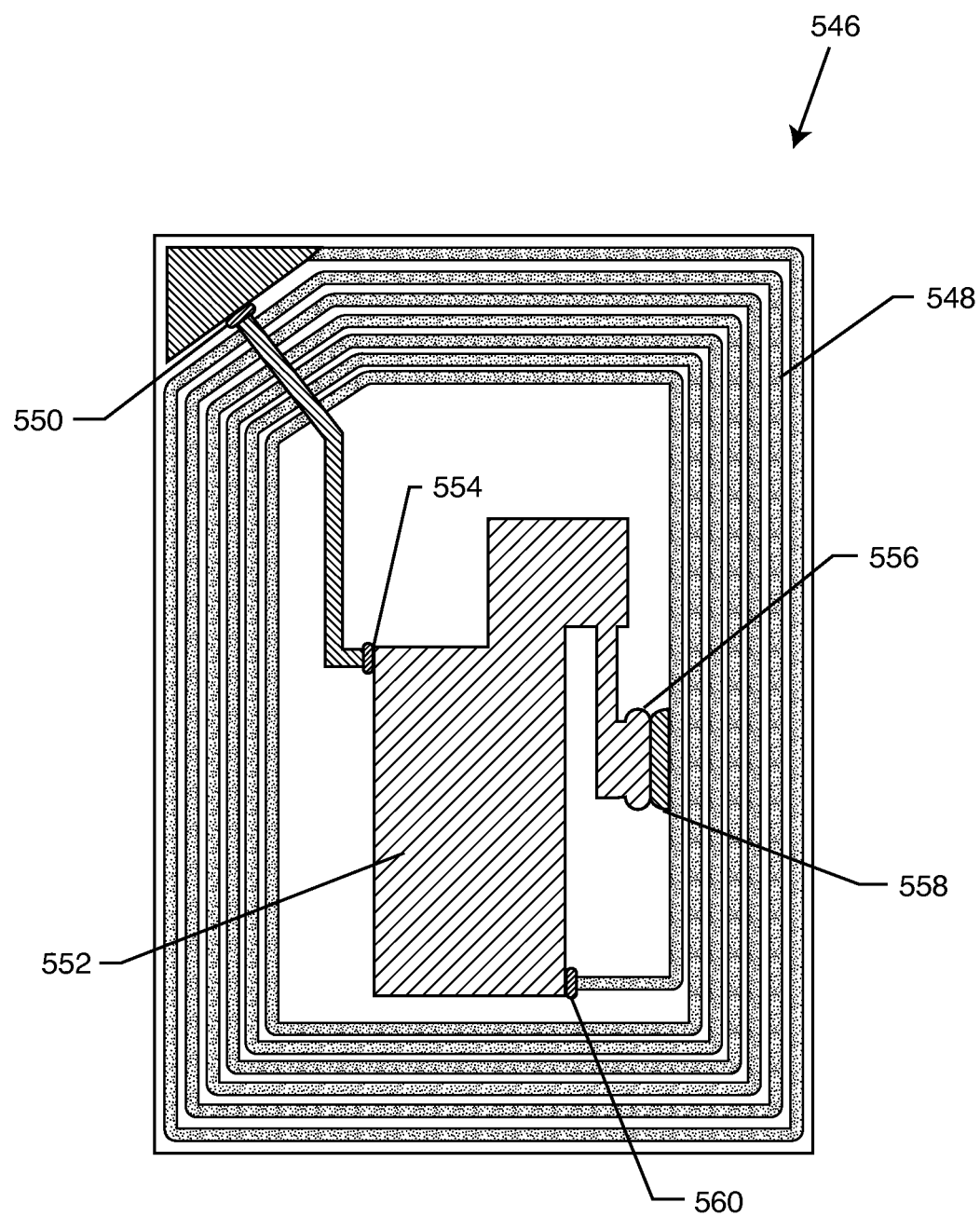
FIG. 96 is a diagrammatic illustration of an RFID chip and its associated antenna.

FIG. 96 is a diagrammatic view of an RFID chip or inlet 546 and its associated antenna 548. Shown is a Wheeler spiral antenna 548 which is terminated at electrical connection 550. It is also connected to the integrated circuit or microchip or integrated circuit (552) at location 554. There are also suitable electrical connections 556 and 558 which connect to the opposite end of the antenna trace. There is also a loop antenna connection which forms a dipole back at location 560. In accordance with the present invention, the microchip and the wiring of the antenna would be of suitable biocompatible and non-migratable materials. Equally important is that all of the electrical connections be also of biocompatible and non-migratable materials of the present invention.

In accordance with the present invention, all of the passive electrical network components, namely, the capacitors, inductors, resistors and bandstop filters illustrated in FIGS. 49-91 are adapted for direct body fluid exposure by including components such as the electrode plates, inductor traces and connection materials, which comprise non-migratable and biocompatible materials. Moreover, any components associated with the passive electrical network components shown must likewise comprise a non-migratable and biocompatible material at least where exposed to body fluid. Preferably, components such as the electrode plates, the inductor tracing, metallization surfaces, and other surfaces which may be directly exposed to body fluids, such as the outer surface of the terminal pin, preferably comprise a noble metal or a noble metal composition. For example, the structures may be comprised of gold, tantalum, niobium, platinum, a gold-based alloy or a platinum-based alloy. Where leadwire attachment is necessary, such wiring would also need to be of biocompatible and nonmigratable materials which include gold, platinum, MP-35N or equivalent. Such biocompatible and non-migratable materials avoid the harmful formation of dendrites as explained above. Other biocompatible metals and alloys that can be used for the capacitor metallization, electrodes, inductor traces, etc. include all of the metals and alloys of titanium, platinum, and platinum iridium alloys, tantalum, niobium, zirconium, hafnium, nitinol, Co—Cr—Ni alloys such as MP35N, HAVAR® and ELGILOY®, stainless steel and gold. There are also a number of conductive metal compounds that can be used, including ZrC, ZrN, TiN, NbO, TiC, TaC, and Indium Oxide/Indium Tin Oxide (Transparent Conductive Oxides).

Moreover, the connection materials used to connect the passive electrical network components to other components such as lead wires, terminal pins and the like, are typically thermal-setting, brazing, welding or soldering materials. So as to be non-migratable, these materials are selected from the group consisting of: gold, gold alloy, platinum, gold-filled-thermal-setting conductive material, platinum-filled-thermal-setting conductive material, gold-bearing glass frit, TiCuSil, CuSil, and gold-based braze.

Table 1 above shows a more comprehensive list of polymers that can also be filled with any of the biocompatible metals mentioned above. This list can include a variety of epoxies and polyimide materials in addition to polyethylene oxide with ionic additions such as NaCl or any of the other commonly used implantable polymers including polyurethane, silicone, polyesters, polycarbonate, polyethylene, polyvinyl chloride, polypropylene, methylacrylate, para-xylene, and polypyrrhol. As mentioned, any of these can be made conductive with a biocompatible material, for example, by adding a particulate filler such as platinum or gold powder. There are other materials that could be used including pyrolytic carbon and Tra-Duct 2902 conductive adhesive.

From the foregoing it will be appreciated that the present invention comprises an implantable passive or active electronic network component or component network is provided which is suitable for prolonged direct body fluid exposure and is attachable to a conductive surface, circuit trace, lead or electrode. The electronic network component or component network comprises (1) a non-conductive body of biocompatible and non-migratable material, (2) a conductive termination surface of biocompatible and non-migratable material associated with the body, and (3) a connection material of biocompatible and non-migratable material for conductively coupling the termination surface to the conductive surface, circuit trace, lead or electrode.

In preferred embodiments, the connection material comprises a thermal-setting adhesive such as a polymer selected from the group consisting of epoxies, polyimides, polyethylene oxide, polyurethane, silicone, polyesters, polycarbonate, polyethylene, polyvinyl chloride, polypropylene, methylacrylate, para-xylyene, and polypyrrhol. The adhesive preferably includes a biocompatible metal filler such as a noble metal filler such as titanium, platinum and platinum/iridium alloys, tantalum, niobium, zirconium, hafnium, nitinol, Co—Cr—Ni alloys such as MP35N, HAVAR® and ELGILOY®, stainless steel, gold, ZrC, ZrN, TiN, NbO, TiC, TaC, Indium Oxide/Indium Tin Oxide.

The termination surface comprises a noble metal or a noble metal composition, or other non-migratable and biocompatible material such as titanium, platinum and platinum/iridium alloys, tantalum, niobium, zirconium, hafnium, nitinol, Co—Cr—Ni alloys such as MP35N, HAVAR® and ELGILOY®, stainless steel, gold, ZrC, ZrN, TiN, NbO, TiC, TaC, Indium Oxide/Indium Tin Oxide.

The biocompatible connection material comprises a brazing, welding or soldering material selected from the group consisting of: titanium, platinum and platinum/iridium alloys, tantalum, niobium, zirconium, hafnium, nitinol, Co—Cr—Ni alloys such as MP35N, HAVAR® and ELGILOY®, stainless steel, gold, ZrC, ZrN, TiN, NbO, TiC, TaC, Indium Oxide/Indium Tin Oxide (Transparent Conductive Oxides), gold-bearing glass frit, TiCuSiI, CuSiI, and gold-based braze. The adhesive may adhere at least a portion of the electronic network component or component network to the conductive surface, circuit trace, lead or electrode The electronic network component may comprise a capacitor, a resistor, an inductor, a diode, a transistor, an electronic switch, a MEMs device, or a microchip.

The electronic network component or component network may include a plurality of conductive circuit traces within the non-conductive body. Such conductive circuit traces preferably comprise a biocompatible and non-migratable material such as gold, platinum, a gold-based alloy or a platinum-based alloy. An adhesive of biocompatible and non-migratable material is preferably utilized for conductively coupling at least two of the plurality of the conductive circuit traces together such as, for example, a multilayer conductor.

Although several embodiments of the present invention have been described in detail for purposes of illustration, various modifications of each may be made without departing from the spirit and scope of the invention. Accordingly, the invention is not to be limited, except as by the appended claims.

What is claimed is:

1. An implantable electronic component network, comprising:
   a) a capacitor, comprising:
      i) a non-conductive body of biocompatible and non-migratable material;
      ii) first and second sets of biocompatible and non-migratable electrode plates embedded within the body; and
      iii) a first conductive termination surface electrically connected to the first set of electrode plates and a second conductive termination surface electrically connected to the second set of electrode plates, wherein at least one of the first and second termination surfaces is of a biocompatible and non-migratable material; and
   b) a connection material of biocompatible and non-migratable material conductively coupling at least one of the first and second termination surfaces to at least one of the group consisting of a conductive surface, a circuit trace, a lead, and an electrode.

2. The electronic component network of claim 1, wherein the connection material comprises an adhesive.

3. The electronic component network of claim 2, wherein the adhesive comprises a thermal-setting adhesive.

4. The electronic component network of claim 3, wherein the adhesive comprises a polymer selected from the group consisting of epoxies, polyimides, polyethylene oxide, polyurethane, silicone, polyesters, polycarbonate, polyethylene, polyvinyl chloride, polypropylene, methylacrylate, para-xylylene, and polypyrrhol.

5. The electronic component network of claim 2, wherein the adhesive includes a biocompatible metal filler.

6. The electronic component network of claim 5, wherein the metal filler comprises a noble metal filler.

7. The electronic component network of claim 3, wherein the thermal-setting material includes a non-migratable and biocompatible conductive filler selected from the group consisting of titanium, platinum and platinum/iridium alloys, tantalum, niobium, zirconium, hafnium, nitinol, Co—Cr—Ni alloys such as MP35N, HAVAR® and ELGILOY®, stainless steel, gold, ZrC, ZrN, TiN, NbO, TiC, TaC, Indium Oxide/Indium Tin Oxide.

8. The electronic component network of claim 1, wherein at least one of the first and second termination surfaces comprises a noble metal or a noble metal composition.

9. The electronic component network of claim 1, wherein at least one of the first and second termination surfaces comprises a non-migratable and biocompatible material selected from the group consisting of titanium, platinum and platinum/iridium alloys, tantalum, niobium, zirconium, hafnium, nitinol, Co—Cr—Ni alloys such as MP35N, HAVAR® and ELGILOY®, stainless steel, gold, ZrC, ZrN, TiN, NbO, TiC, TaC, Indium Oxide/Indium Tin Oxide.

10. The electronic component network of claim 2, wherein the adhesive adheres at least a portion of one of the first and second termination surfaces to the conductive surface, the circuit trace, the lead, and the electrode.

11. The electronic component network of claim 1, wherein the biocompatible connection material comprises a brazing, welding or soldering material selected from the group consisting of: titanium, platinum and platinum/iridium alloys, tantalum, niobium, zirconium, hafnium, nitinol, Co—Cr—Ni alloys such as MP35N, Havar® and Elgiloy®, stainless steel, gold, ZrC, ZrN, TiN, NbO, TiC, TaC, Indium Oxide/Indium Tin Oxide (Transparent Conductive Oxides), gold-bearing glass frit, TiCuSiI, CuSiI, and gold-based braze.

12. The electronic component network of claim 1, wherein the electronic network component further comprises at least one of the group consisting of a resistor, an inductor, a diode, a transistor, an electronic switch, a MEMs device, and a microchip.

13. The electronic component network of claim 1 wherein the first and second sets of electrode plates comprise a noble metal or noble metal composition.

14. The electronic component network of claim 1 wherein the first and second sets of electrode plates are of a material selected from the group consisting of gold, platinum, a gold based alloy, and a platinum based alloy.

15. The electronic component network of claim 12, wherein the inductor comprises at least one biocompatible and non-migratable circuit trace on a surface of the body, and wherein the circuit trace extends from the first biocompatible and non-migratable termination surface to the second biocompatible and non-migratable termination surface.

16. The electronic component network of claim 15, wherein the inductor circuit trace comprises a noble metal or a noble metal composition.

17. The electronic component network of claim 15 wherein the inductor circuit trace is of a material selected from the group consisting of gold, platinum, a gold based alloy, and a platinum based alloy.

18. The electronic component network of claim 12, wherein the inductor comprises at least one biocompatible and non-migratable inductor circuit trace embedded within the body and extending from the first biocompatible and non-migratable termination surface to the second biocompatible and non-migratable termination surface.

19. The electronic component network of claim 18, wherein the inductor circuit trace comprises a noble metal or a noble metal composition.

20. The electronic component network of claim 19, wherein the inductor circuit trace is selected from the group consisting of gold, platinum, a gold based alloy, and a platinum based alloy.

21. The electronic component network of claim 18, wherein the capacitor in parallel with the inductor form a bandstop filter.

22. The electronic component network of claim 12, wherein the resistor comprises a biocompatible and non-migratable circuit trace on a surface of the body, and wherein the circuit trace extends from the first biocompatible and non-migratable termination surface to the second biocompatible and non-migratable termination surface.

23. The electronic component network of claim 22, wherein the resistor circuit trace comprises a noble metal or a noble metal composition.

24. The electronic component network of claim 22 wherein the resistor circuit trace is of a material selected from the group consisting of gold, platinum, a gold based alloy, and a platinum based alloy.

25. The electronic component network of claim 12, wherein the resistor comprises at least one biocompatible and non-migratable resistor circuit trace embedded within the body and extending from the first biocompatible and non-migratable termination surface to the second biocompatible and non-migratable termination surface.

26. The electronic component network of claim 25, wherein the resistor circuit trace comprises a noble metal or a noble metal composition.

27. The electronic component network of claim 26, wherein the resistor circuit trace is selected from the group consisting of gold, platinum, a gold based alloy, and a platinum based alloy.

28. The electronic component network of claim 12, wherein the diode comprises at least one biocompatible and non-migratable circuit trace embedded within the body and extending from the first biocompatible and non-migratable termination surface to the second biocompatible and non-migratable termination surface.

29. The electronic component network of claim 12 wherein the diode circuit trace comprises a noble metal or a noble metal composition.

30. The electronic component network of claim 12 wherein the diode circuit trace is selected from the group consisting of gold, platinum, a gold based alloy and a platinum based alloy.

31. The electronic component network of claim 12, wherein the electronic switch comprises at least one biocompatible and non-migratable conductor embedded within the body and extending from the first biocompatible and non-migratable termination surface to the second biocompatible and non-migratable termination surface.

32. The electronic component network of claim 31, wherein the electronic switch conductor comprises a noble metal or a noble metal composition.

33. The electronic component network of claim 32, wherein the electronic switch conductor is of a material selected from the group consisting of gold, platinum, a gold based alloy, and a platinum based alloy.

34. The electronic component network of claim 12, wherein the MEMs device comprises at least one MEMs conductor embedded within the body and extending from the first biocompatible and non-migratable termination surface to the second biocompatible and non-migratable termination surface.

35. The electronic component network of claim 34, wherein the MEMs conductor comprises a noble metal or a noble metal composition.

36. The electronic component network of claim 35, wherein the MEMs conductor is of a material selected from the group consisting of gold, platinum, a gold based alloy, and a platinum based alloy.

37. The electronic component network of claim 12, wherein the transistor comprises at least one biocompatible and non-migratable transistor circuit trace embedded within the body and extending from the first biocompatible and non-migratable termination surface to the second biocompatible and non-migratable termination surface.

38. The electronic component network of claim 37, wherein the transistor circuit trace comprises a noble metal or a noble metal composition.

39. The electronic component network of claim 38, wherein the transistor circuit trace is of a material selected from the group consisting of gold, platinum, a gold based alloy, and a platinum based alloy.

40. The electronic component network of claim 12, wherein the microchip comprises at least one biocompatible and non-migratable microchip circuit trace embedded within the body and extending from the first biocompatible and non-migratable termination surface to the second biocompatible and non-migratable termination surface.

41. The electronic component network of claim 40, wherein the microchip circuit trace comprises a noble metal or a noble metal composition.

42. The electronic component network of claim 40, wherein the microchip circuit trace is of a material selected from the group consisting of gold, platinum, a gold based alloy, and a platinum based alloy.

43. The electronic component network of claim 1, including a plurality of conductive circuit traces within the non-conductive body.

44. The electronic component network of claim 43, wherein the conductive circuit traces comprise a biocompatible and non-migratable material.

45. The electronic component network of claim 44, wherein the conductive circuit traces comprise a noble metal or a noble metal composition.

46. The electronic component network of claim 45, wherein the conductive circuit traces is of a material selected from the group consisting of gold, platinum, a gold based alloy, and a platinum based alloy.

47. The electronic component network of claim 43, including an adhesive of biocompatible and non-migratable material conductively coupling at least two of the plurality of the conductive circuit traces together.

48. The electronic component network of claim 47, wherein the electronic network component comprises an inductor.

49. The electronic component network of claim 12, wherein the microchip comprises an RFID inlet.

50. The electronic component network of claim 49, including an adhesive of biocompatible and non-migratable material conductively coupling the RFID inlet to an RFID antenna.

* * * * *